(12) United States Patent
McDonough et al.

(10) Patent No.: US 9,192,419 B2
(45) Date of Patent: Nov. 24, 2015

(54) ZERO-PROFILE INTERBODY SPACER AND COUPLED PLATE ASSEMBLY

(75) Inventors: William P. McDonough, Collegeville, PA (US); William L. Strausbaugh, Newmanstown, PA (US); Christopher Bonner, Downingtown, PA (US); Thomas Pepe, Turnersville, NJ (US); Ralph Meili, Muttenz (CH); Markus Hunziker, Aarau (CH); Michael Jeger, Thuernen (CH); Thomas Kueenzi, Downingtown, PA (US); David Koch, Bubendorf (CH); Rainer Ponzer, Himmelried (CH); Joern Richter, Kandern (DE); Roger Berger, Bueren (CH)

(73) Assignee: DePuy Synthes Products, Inc., Raynham, MA (US)

( * ) Notice: Subject to any disclaimer, the term of this patent is extended or adjusted under 35 U.S.C. 154(b) by 572 days.

(21) Appl. No.: 12/613,866

(22) Filed: Nov. 6, 2009

(65) Prior Publication Data

US 2010/0145459 A1 Jun. 10, 2010

Related U.S. Application Data

(60) Provisional application No. 61/112,441, filed on Nov. 7, 2008, provisional application No. 61/139,920, filed on Dec. 22, 2008.

(51) Int. Cl.
*A61F 2/44* (2006.01)
*A61B 17/88* (2006.01)
(Continued)

(52) U.S. Cl.
CPC .............. *A61B 17/88* (2013.01); *A61B 17/1757* (2013.01); *A61B 17/8033* (2013.01);
(Continued)

(58) Field of Classification Search
USPC .................... 606/289–296; 623/17.11–17.16
See application file for complete search history.

(56) References Cited

U.S. PATENT DOCUMENTS

| 424,836 A | 4/1890 | Thompson |
| 1,105,105 A | 7/1914 | Sherman |

(Continued)

FOREIGN PATENT DOCUMENTS

| AU | 2004/232317 | 11/2010 |
| CA | 2317791 A1 | 8/1999 |

(Continued)

OTHER PUBLICATIONS

PCT: International Search Report & Written Opinion.
(Continued)

*Primary Examiner* — David Isabella
*Assistant Examiner* — Christine Nelson
(74) *Attorney, Agent, or Firm* — Baker & Hostetler LLP

(57) ABSTRACT

An implant for insertion into a disc space between vertebrae, wherein the implant includes a spacer portion, a plate portion coupled to the spacer portion, two bone fixation elements for engaging the vertebrae and a retention mechanism for preventing the bone fixation elements from postoperatively backing-out of the plate portion. The retention mechanism may be in the form of a spring biased snapper element that is biased into communication with the bone fixation elements so that once the bone fixation element advances past the snapper element, the snapper element is biased back to its initial position in which the snapper element interfaces with the bone fixation elements. Alternatively, the retention mechanism may be in the form of a propeller rotatable between a first position in which the bone fixation elements are insertable to a second position where the bone fixation elements are prevented from backing-out.

31 Claims, 25 Drawing Sheets

(51) Int. Cl.
*A61B 17/80* (2006.01)
*A61F 2/46* (2006.01)
*A61B 17/17* (2006.01)
*A61B 17/86* (2006.01)
*A61F 2/30* (2006.01)

(52) U.S. Cl.
CPC ......... *A61B17/8042* (2013.01); *A61B 17/8052* (2013.01); *A61F 2/4465* (2013.01); *A61F 2/4611* (2013.01); *A61B 17/1728* (2013.01); *A61B 17/8057* (2013.01); *A61B 17/86* (2013.01); *A61F 2/30965* (2013.01); *A61F 2002/305* (2013.01); *A61F 2002/30387* (2013.01); *A61F 2002/30505* (2013.01); *A61F 2002/30507* (2013.01); *A61F 2002/30517* (2013.01); *A61F 2002/30576* (2013.01); *A61F 2002/30604* (2013.01); *A61F 2002/30787* (2013.01); *A61F 2002/30794* (2013.01); *A61F 2002/30841* (2013.01); *A61F 2002/4475* (2013.01); *A61F 2220/0025* (2013.01); *A61F 2310/00017* (2013.01); *A61F 2310/00023* (2013.01); *A61F 2310/00029* (2013.01); *A61F 2310/00131* (2013.01); *A61F 2310/00407* (2013.01); *A61F 2310/00796* (2013.01)

(56) References Cited

U.S. PATENT DOCUMENTS

| | | |
|---|---|---|
| 1,200,797 A | 10/1916 | Barbe |
| 2,151,919 A | 3/1939 | Jacobson |
| 2,372,888 A | 4/1945 | Edward |
| 2,621,145 A | 12/1952 | Sano |
| 2,782,827 A | 2/1957 | Joseph |
| 2,906,311 A | 9/1959 | Boyd |
| 2,972,367 A | 2/1961 | Wootton |
| 3,062,253 A | 11/1962 | Melvin |
| 3,272,249 A | 9/1966 | Houston |
| 3,350,103 A | 10/1967 | Ahlstone |
| 3,561,075 A | 2/1971 | Selinko |
| 3,579,831 A | 5/1971 | Stevens et al. |
| 3,707,303 A | 12/1972 | Petri |
| 3,810,703 A | 5/1974 | Pasbrig |
| 3,899,897 A | 8/1975 | Boerger et al. |
| 3,945,671 A | 3/1976 | Gerlach |
| 4,017,946 A | 4/1977 | Soja |
| 4,056,301 A | 11/1977 | Norden |
| 4,123,132 A | 10/1978 | Hardy |
| 4,135,506 A | 1/1979 | Ulrich |
| 4,278,120 A | 7/1981 | Hart et al. |
| 4,280,875 A | 7/1981 | Werres |
| 4,285,377 A | 8/1981 | Hart |
| 4,288,902 A | 9/1981 | Franz |
| 4,297,063 A | 10/1981 | Hart |
| 4,299,902 A | 11/1981 | Soma et al. |
| 4,388,921 A | 6/1983 | Sutter et al. |
| 4,484,570 A | 11/1984 | Sutter et al. |
| 4,488,543 A | 12/1984 | Tornier |
| 4,501,269 A | 2/1985 | Bagby |
| 4,503,848 A | 3/1985 | Caspar et al. |
| 4,512,038 A | 4/1985 | Alexander et al. |
| 4,553,890 A | 11/1985 | Gulistan |
| 4,599,086 A | 7/1986 | Doty |
| 4,627,853 A | 12/1986 | Campbell et al. |
| 4,640,524 A | 2/1987 | Sedlmair |
| 4,648,768 A | 3/1987 | Hambric |
| 4,678,470 A | 7/1987 | Nashef et al. |
| 4,708,377 A | 11/1987 | Hunting |
| 4,711,760 A | 12/1987 | Blaushild |
| 4,717,115 A | 1/1988 | Schmitz |
| 4,793,335 A | 12/1988 | Frey et al. |
| 4,804,290 A | 2/1989 | Balsells |
| 4,812,094 A | 3/1989 | Grube |
| 4,858,603 A | 8/1989 | Clemow et al. |
| 4,904,261 A | 2/1990 | Dove et al. |
| 4,936,851 A | 6/1990 | Fox et al. |
| 4,950,296 A | 8/1990 | McIntyre |
| 4,955,908 A | 9/1990 | Frey et al. |
| 4,961,740 A | 10/1990 | Ray et al. |
| 4,976,576 A | 12/1990 | Mahaney |
| 4,978,350 A | 12/1990 | Wagenknecht |
| 4,994,084 A | 2/1991 | Brennan |
| 5,010,783 A | 4/1991 | Sparks et al. |
| 5,017,069 A | 5/1991 | Stencel |
| 5,020,949 A | 6/1991 | Davidson et al. |
| 5,026,373 A | 6/1991 | Ray et al. |
| 5,030,220 A | 7/1991 | Howland |
| 5,053,049 A | 10/1991 | Campbell |
| 5,062,850 A | 11/1991 | MacMillan et al. |
| 5,071,437 A | 12/1991 | Steffee |
| 5,084,051 A | 1/1992 | Törmälä et al. |
| 5,085,660 A | 2/1992 | Lin |
| 5,096,150 A | 3/1992 | Westwood |
| 5,108,438 A | 4/1992 | Stone et al. |
| 5,112,354 A | 5/1992 | Sires |
| 5,118,235 A | 6/1992 | Dill |
| 5,139,424 A | 8/1992 | Yli-Urpo |
| 5,147,404 A | 9/1992 | Downey |
| 5,180,381 A | 1/1993 | Aust et al. |
| 5,192,327 A | 3/1993 | Brantigan |
| 5,207,543 A | 5/1993 | Kirma |
| 5,211,664 A | 5/1993 | Tepic et al. |
| 5,235,034 A | 8/1993 | Bobsein et al. |
| 5,238,342 A | 8/1993 | Stencel |
| 5,275,601 A | 1/1994 | Gogolewski et al. |
| 5,281,226 A | 1/1994 | Davydov et al. |
| 5,284,655 A | 2/1994 | Bogdansky et al. |
| 5,290,312 A | 3/1994 | Kojimoto et al. |
| 5,298,254 A | 3/1994 | Prewett et al. |
| 5,304,021 A | 4/1994 | Oliver et al. |
| 5,314,476 A | 5/1994 | Prewett et al. |
| 5,314,477 A | 5/1994 | Marnay |
| 5,330,535 A | 7/1994 | Moser et al. |
| 5,348,788 A | 9/1994 | White |
| 5,368,593 A | 11/1994 | Stark |
| 5,380,323 A | 1/1995 | Howland |
| 5,385,583 A | 1/1995 | Cotrel |
| 5,397,364 A | 3/1995 | Kozak et al. |
| 5,405,391 A | 4/1995 | Hednerson et al. |
| 5,411,348 A | 5/1995 | Balsells |
| 5,423,817 A | 6/1995 | Lin |
| 5,425,772 A | 6/1995 | Brantigan |
| 5,439,684 A | 8/1995 | Prewett et al. |
| 5,458,638 A | 10/1995 | Kuslich et al. |
| 5,458,641 A | 10/1995 | Ramirez |
| 5,458,643 A | 10/1995 | Oka et al. |
| 5,478,342 A | 12/1995 | Kohrs |
| 5,487,744 A | 1/1996 | Howland |
| 5,489,308 A | 2/1996 | Kuslich et al. |
| 5,507,818 A | 4/1996 | McLaughlin |
| 5,514,180 A | 5/1996 | Heggeness et al. |
| 5,520,690 A | 5/1996 | Errico et al. |
| 5,522,899 A | 6/1996 | Michelson |
| 5,531,746 A | 7/1996 | Errico et al. |
| 5,534,030 A | 7/1996 | Navarro et al. |
| 5,534,031 A | 7/1996 | Matsuzaki et al. |
| 5,534,032 A | 7/1996 | Hodorek |
| 5,545,842 A | 8/1996 | Balsells |
| 5,549,612 A | 8/1996 | Yapp et al. |
| 5,549,679 A | 8/1996 | Kuslich |
| 5,554,191 A | 9/1996 | Lahille et al. |
| 5,556,430 A | 9/1996 | Gendler |
| 5,569,308 A | 10/1996 | Sottosanti |
| 5,570,983 A | 11/1996 | Hollander |
| 5,571,190 A | 11/1996 | Ulrich et al. |
| 5,571,192 A | 11/1996 | Schönhöffer |
| 5,578,034 A | 11/1996 | Estes |
| 5,593,409 A | 1/1997 | Michelson |
| 5,597,278 A | 1/1997 | Peterkort |
| 5,601,553 A | 2/1997 | Trebing et al. |
| 5,601,554 A | 2/1997 | Howland et al. |
| 5,607,428 A | 3/1997 | Lin |
| 5,607,474 A | 3/1997 | Athanasiou et al. |

(56) References Cited

U.S. PATENT DOCUMENTS

| | | |
|---|---|---|
| 5,609,635 A | 3/1997 | Michelson |
| 5,609,636 A | 3/1997 | Kohrs et al. |
| 5,609,637 A | 3/1997 | Biedermann et al. |
| 5,616,144 A | 4/1997 | Yapp et al. |
| 5,642,960 A | 7/1997 | Salice |
| 5,645,606 A | 7/1997 | Oehy et al. |
| 5,653,708 A | 8/1997 | Howland |
| 5,676,666 A | 10/1997 | Oxland |
| 5,676,699 A | 10/1997 | Gogolewski |
| 5,681,311 A | 10/1997 | Foley et al. |
| 5,683,216 A | 11/1997 | Erbes |
| 5,683,394 A | 11/1997 | Rinner |
| 5,683,463 A | 11/1997 | Godefroy et al. |
| 5,702,449 A | 12/1997 | McKay |
| 5,702,451 A | 12/1997 | Biedermann et al. |
| 5,702,453 A | 12/1997 | Rabbe et al. |
| 5,702,455 A | 12/1997 | Saggar |
| 5,713,899 A | 2/1998 | Marnay et al. |
| 5,713,900 A | 2/1998 | Benzel et al. |
| 5,725,588 A | 3/1998 | Errico et al. |
| 5,728,159 A | 3/1998 | Stroever et al. |
| 5,735,853 A | 4/1998 | Olerud |
| 5,735,905 A | 4/1998 | Parr |
| 5,755,796 A | 5/1998 | Ibo et al. |
| 5,766,253 A | 6/1998 | Brosnahan, III |
| 5,776,194 A | 7/1998 | Mikol et al. |
| 5,776,196 A | 7/1998 | Matsuzaki et al. |
| 5,776,197 A | 7/1998 | Rabbe et al. |
| 5,776,198 A | 7/1998 | Rabbe et al. |
| 5,776,199 A | 7/1998 | Michelson |
| 5,778,804 A | 7/1998 | Read |
| 5,782,915 A | 7/1998 | Stone |
| 5,785,710 A | 7/1998 | Michelson |
| 5,800,433 A | 9/1998 | Benzel et al. |
| 5,861,041 A | 1/1999 | Tienboon |
| 5,865,845 A | 2/1999 | Thalgott |
| 5,865,849 A | 2/1999 | Stone |
| 5,876,402 A | 3/1999 | Errico et al. |
| 5,876,452 A | 3/1999 | Athanasiou et al. |
| 5,879,389 A | 3/1999 | Koshino |
| 5,885,299 A | 3/1999 | Winslow et al. |
| 5,888,222 A | 3/1999 | Coates et al. |
| 5,888,223 A | 3/1999 | Bray, Jr. |
| 5,888,224 A | 3/1999 | Beckers et al. |
| 5,888,227 A | 3/1999 | Cottle |
| 5,895,426 A | 4/1999 | Scarborough et al. |
| 5,899,939 A | 5/1999 | Boyce et al. |
| 5,902,303 A | 5/1999 | Eckhof et al. |
| 5,902,338 A | 5/1999 | Stone |
| 5,904,683 A | 5/1999 | Pohndorf et al. |
| 5,904,719 A | 5/1999 | Errico et al. |
| 5,910,315 A | 6/1999 | Stevenson et al. |
| 5,911,758 A | 6/1999 | Oehy et al. |
| 5,920,312 A | 7/1999 | Wagner et al. |
| 5,922,027 A | 7/1999 | Stone |
| 5,931,838 A | 8/1999 | Vito |
| 5,944,755 A | 8/1999 | Stone |
| 5,951,558 A | 9/1999 | Fiz |
| 5,954,722 A | 9/1999 | Bono |
| 5,968,098 A | 10/1999 | Winslow |
| 5,972,368 A | 10/1999 | McKay |
| 5,976,141 A | 11/1999 | Haag et al. |
| 5,976,187 A | 11/1999 | Richelsoph |
| 5,980,522 A | 11/1999 | Koros et al. |
| 5,981,828 A | 11/1999 | Nelson et al. |
| 5,984,967 A | 11/1999 | Zdeblick et al. |
| 5,989,289 A | 11/1999 | Coates et al. |
| 6,013,853 A | 1/2000 | Athanasiou et al. |
| 6,017,345 A | 1/2000 | Richelsoph |
| 6,025,538 A | 2/2000 | Yaccarino, III |
| 6,033,405 A | 3/2000 | Winslow et al. |
| 6,033,438 A | 3/2000 | Bianchi et al. |
| 6,039,762 A | 3/2000 | McKay |
| 6,045,579 A | 4/2000 | Hochshuler et al. |
| 6,045,580 A | 4/2000 | Scarborough et al. |
| 6,056,749 A | 5/2000 | Kuslich |
| 6,066,175 A | 5/2000 | Henderson et al. |
| 6,080,158 A | 6/2000 | Lin |
| 6,080,193 A | 6/2000 | Hochshuler et al. |
| 6,086,593 A | 7/2000 | Bonutti |
| 6,086,614 A | 7/2000 | Mumme |
| 6,090,998 A | 7/2000 | Grooms et al. |
| 6,096,080 A | 8/2000 | Nicholson et al. |
| 6,096,081 A | 8/2000 | Grivas et al. |
| 6,099,531 A | 8/2000 | Bonutti |
| 6,110,482 A | 8/2000 | Khouri et al. |
| 6,113,637 A | 9/2000 | Gill et al. |
| 6,113,638 A | 9/2000 | Williams et al. |
| 6,120,503 A | 9/2000 | Michelson |
| 6,123,731 A | 9/2000 | Boyce et al. |
| 6,129,763 A | 10/2000 | Chauvin et al. |
| 6,136,001 A | 10/2000 | Michelson |
| 6,139,550 A | 10/2000 | Michelson |
| 6,143,030 A | 11/2000 | Schroder |
| 6,143,033 A | 11/2000 | Paul et al. |
| 6,156,070 A | 12/2000 | Incavo et al. |
| 6,193,721 B1 | 2/2001 | Michelson |
| 6,193,756 B1 | 2/2001 | Studer et al. |
| 6,193,757 B1 | 2/2001 | Foley et al. |
| 6,200,347 B1 | 3/2001 | Anderson et al. |
| 6,206,922 B1 | 3/2001 | Zdeblick et al. |
| 6,224,602 B1 | 5/2001 | Hayes |
| 6,231,610 B1 | 5/2001 | Geisler |
| 6,235,033 B1 | 5/2001 | Brace et al. |
| 6,235,034 B1 | 5/2001 | Bray |
| 6,235,059 B1 | 5/2001 | Benezech et al. |
| 6,241,731 B1 | 6/2001 | Fiz |
| 6,241,769 B1 | 6/2001 | Nicholson et al. |
| 6,245,108 B1 | 6/2001 | Biscup |
| 6,258,089 B1 | 7/2001 | Campbell et al. |
| 6,258,125 B1 | 7/2001 | Paul et al. |
| 6,261,291 B1 | 7/2001 | Talaber et al. |
| 6,261,586 B1 | 7/2001 | McKay |
| 6,264,695 B1 | 7/2001 | Stoy |
| 6,270,528 B1 | 8/2001 | McKay |
| 6,306,139 B1 | 10/2001 | Fuentes |
| 6,322,562 B1 | 11/2001 | Wolter |
| 6,331,179 B1 | 12/2001 | Freid et al. |
| 6,342,074 B1 | 1/2002 | Simpson |
| 6,364,880 B1 | 4/2002 | Michelson |
| 6,371,986 B1 | 4/2002 | Bagby |
| 6,371,988 B1 | 4/2002 | Pafford et al. |
| 6,371,989 B1 | 4/2002 | Chauvin et al. |
| 6,375,681 B1 | 4/2002 | Truscott |
| 6,383,186 B1 | 5/2002 | Michelson |
| 6,387,130 B1 | 5/2002 | Stone et al. |
| 6,395,031 B1 | 5/2002 | Foley et al. |
| 6,413,259 B1 | 7/2002 | Lyons et al. |
| 6,423,063 B1 | 7/2002 | Bonutti |
| 6,432,106 B1 | 8/2002 | Fraser |
| 6,447,512 B1 | 9/2002 | Landry et al. |
| 6,447,546 B1 | 9/2002 | Bramlet et al. |
| 6,454,771 B1 | 9/2002 | Michelson |
| 6,458,158 B1 | 10/2002 | Anderson et al. |
| 6,461,359 B1 | 10/2002 | Tribus et al. |
| 6,468,311 B2 | 10/2002 | Boyd et al. |
| 6,471,724 B2 | 10/2002 | Zdeblick et al. |
| 6,503,250 B2 | 1/2003 | Paul |
| 6,524,312 B2 | 2/2003 | Landry et al. |
| 6,558,387 B2 | 5/2003 | Errico et al. |
| 6,558,423 B1 | 5/2003 | Michelson |
| 6,558,424 B2 | 5/2003 | Thalgott |
| 6,562,073 B2 | 5/2003 | Foley |
| 6,569,201 B2 | 5/2003 | Moumene et al. |
| 6,575,975 B2 | 6/2003 | Brace et al. |
| 6,576,017 B2 | 6/2003 | Foley et al. |
| 6,579,290 B1 | 6/2003 | Hardcastle et al. |
| 6,592,624 B1 | 7/2003 | Fraser et al. |
| 6,602,291 B1 | 8/2003 | Ray et al. |
| 6,605,090 B1 | 8/2003 | Trieu et al. |
| 6,616,671 B2 | 9/2003 | Landry et al. |
| 6,620,163 B1 | 9/2003 | Michelson |
| 6,623,486 B1 | 9/2003 | Weaver et al. |
| 6,629,998 B1 | 10/2003 | Lin |

(56) References Cited

U.S. PATENT DOCUMENTS

| | | |
|---|---|---|
| 6,638,310 B2 | 10/2003 | Lin et al. |
| 6,645,212 B2 | 11/2003 | Goldhahn et al. |
| 6,652,525 B1 | 11/2003 | Assaker et al. |
| 6,656,181 B2 | 12/2003 | Dixon et al. |
| 6,679,887 B2 | 1/2004 | Nicholson et al. |
| 6,682,561 B2 | 1/2004 | Songer et al. |
| 6,682,563 B2 | 1/2004 | Scharf |
| 6,695,846 B2 | 2/2004 | Richelsoph et al. |
| 6,695,851 B2 | 2/2004 | Zdeblick et al. |
| 6,706,067 B2 | 3/2004 | Shimp et al. |
| 6,709,456 B2 | 3/2004 | Langberg et al. |
| 6,712,818 B1 | 3/2004 | Michelson |
| 6,730,127 B2 | 5/2004 | Michelson |
| 6,736,850 B2 | 5/2004 | Davis |
| 6,761,739 B2 | 7/2004 | Shepard |
| 6,770,096 B2 | 8/2004 | Bolger et al. |
| 6,786,909 B1 | 9/2004 | Dransfeld |
| 6,800,092 B1 | 10/2004 | Williams et al. |
| 6,805,714 B2 | 10/2004 | Sutcliffe |
| 6,808,537 B2 | 10/2004 | Michelson |
| 6,824,564 B2 | 11/2004 | Crozet |
| 6,833,006 B2 | 12/2004 | Foley et al. |
| 6,837,905 B1 | 1/2005 | Lieberman |
| 6,849,093 B2 | 2/2005 | Michelson |
| 6,855,168 B2 | 2/2005 | Crozet |
| 6,863,673 B2 | 3/2005 | Gerbec et al. |
| 6,872,915 B2 | 3/2005 | Koga et al. |
| 6,884,242 B2 | 4/2005 | LeHuec et al. |
| 6,890,334 B2 | 5/2005 | Brace et al. |
| 6,899,735 B2 | 5/2005 | Coates et al. |
| 6,902,578 B1 | 6/2005 | Anderson et al. |
| 6,916,320 B2 | 7/2005 | Michelson |
| 6,923,756 B2 | 8/2005 | Sudakov et al. |
| 6,953,477 B2 | 10/2005 | Berry |
| 6,962,606 B2 | 11/2005 | Michelson |
| 6,964,664 B2 | 11/2005 | Freid et al. |
| 6,964,687 B1 | 11/2005 | Bernard et al. |
| 6,972,019 B2 | 12/2005 | Michelson |
| 6,972,035 B2 | 12/2005 | Michelson |
| 6,974,479 B2 | 12/2005 | Trieu |
| 6,984,234 B2 | 1/2006 | Bray |
| 7,001,385 B2 | 2/2006 | Bonutti |
| 7,001,432 B2 | 2/2006 | Keller et al. |
| 7,018,416 B2 | 3/2006 | Hanson et al. |
| 7,033,394 B2 | 4/2006 | Michelson |
| 7,041,135 B2 | 5/2006 | Michelson |
| 7,044,968 B1 | 5/2006 | Yaccarino et al. |
| 7,044,972 B2 | 5/2006 | Mathys et al. |
| 7,060,097 B2 | 6/2006 | Fraser et al. |
| 7,066,961 B2 | 6/2006 | Michelson |
| 7,077,864 B2 | 7/2006 | Byrd, III et al. |
| 7,112,222 B2 | 9/2006 | Fraser et al. |
| 7,112,223 B2 | 9/2006 | Davis |
| 7,135,024 B2 | 11/2006 | Cook et al. |
| 7,135,043 B2 | 11/2006 | Nakahara et al. |
| 7,137,984 B2 | 11/2006 | Michelson |
| 7,147,665 B1 | 12/2006 | Bryan et al. |
| 7,163,561 B2 | 1/2007 | Michelson |
| 7,172,627 B2 | 2/2007 | Fiere et al. |
| 7,226,452 B2 | 6/2007 | Zubok |
| 7,226,482 B2 | 6/2007 | Messerli et al. |
| 7,232,463 B2 | 6/2007 | Falahee |
| 7,232,464 B2 | 6/2007 | Mathieu et al. |
| 7,238,203 B2 | 7/2007 | Bagga et al. |
| 7,255,698 B2 | 8/2007 | Michelson |
| 7,276,082 B2 | 10/2007 | Zdeblick et al. |
| 7,320,708 B1 | 1/2008 | Bernstein |
| 7,323,011 B2 | 1/2008 | Shepard et al. |
| 7,442,209 B2 | 10/2008 | Michelson |
| 7,491,237 B2 | 2/2009 | Randall et al. |
| 7,534,265 B1 | 5/2009 | Boyd et al. |
| 7,594,932 B2 | 9/2009 | Aferzon et al. |
| 7,601,173 B2 | 10/2009 | Messerli et al. |
| 7,608,107 B2 | 10/2009 | Michelson |
| 7,618,456 B2 | 11/2009 | Mathieu et al. |
| 7,625,380 B2 | 12/2009 | Drewry et al. |
| 7,637,951 B2 | 12/2009 | Michelson |
| 7,655,042 B2 | 2/2010 | Foley et al. |
| 7,704,279 B2 | 4/2010 | Moskowitz et al. |
| 7,846,188 B2 | 12/2010 | Moskowitz et al. |
| 7,846,207 B2 | 12/2010 | Lechmann et al. |
| 7,862,616 B2 | 1/2011 | Lechmann |
| 7,875,076 B2 | 1/2011 | Mathieu et al. |
| 7,942,903 B2 | 5/2011 | Moskowitz et al. |
| 7,993,403 B2 | 8/2011 | Foley et al. |
| 8,062,303 B2 | 11/2011 | Berry et al. |
| 8,128,700 B2 | 3/2012 | Delurio et al. |
| 8,182,532 B2 | 5/2012 | Anderson et al. |
| 8,211,148 B2 | 7/2012 | Zhang et al. |
| 8,273,127 B2 | 9/2012 | Jones et al. |
| 8,308,804 B2 | 11/2012 | Kureger |
| 8,328,872 B2 | 12/2012 | Duffield et al. |
| 8,343,222 B2 | 1/2013 | Cope |
| 8,353,913 B2 | 1/2013 | Moskowitz et al. |
| 8,382,768 B2 | 2/2013 | Berry et al. |
| 8,425,607 B2 | 4/2013 | Waugh et al. |
| 8,465,546 B2 | 6/2013 | Jodaitis et al. |
| 8,540,774 B2 | 9/2013 | Kueenzi et al. |
| 8,545,567 B1 | 10/2013 | Krueger |
| 8,641,743 B2 | 2/2014 | Michelson |
| 8,641,768 B2 | 2/2014 | Duffield et al. |
| 8,764,831 B2 | 7/2014 | Lechmann et al. |
| 9,005,295 B2 | 4/2015 | Kueenzi et al. |
| 2001/0001129 A1 | 5/2001 | McKay et al. |
| 2001/0005796 A1 | 6/2001 | Zdeblick et al. |
| 2001/0010021 A1 | 7/2001 | Boyd et al. |
| 2001/0016777 A1 | 8/2001 | Biscup |
| 2001/0020186 A1 | 9/2001 | Boyee et al. |
| 2001/0031254 A1 | 10/2001 | Bianchi et al. |
| 2001/0039456 A1 | 11/2001 | Boyer, II et al. |
| 2001/0041941 A1 | 11/2001 | Boyer, II et al. |
| 2002/0004683 A1 | 1/2002 | Michelson et al. |
| 2002/0010511 A1 | 1/2002 | Michelson |
| 2002/0016595 A1 | 2/2002 | Michelson |
| 2002/0022843 A1 | 2/2002 | Michelson |
| 2002/0029084 A1 | 3/2002 | Paul et al. |
| 2002/0065517 A1 | 5/2002 | Paul |
| 2002/0082597 A1 | 6/2002 | Fraser |
| 2002/0082603 A1 | 6/2002 | Dixon et al. |
| 2002/0091447 A1 | 7/2002 | Shimp et al. |
| 2002/0095155 A1 | 7/2002 | Michelson |
| 2002/0099376 A1 | 7/2002 | Michelson |
| 2002/0099378 A1 | 7/2002 | Michelson |
| 2002/0106393 A1 | 8/2002 | Bianchi et al. |
| 2002/0111680 A1 | 8/2002 | Michelson |
| 2002/0128712 A1 | 9/2002 | Michelson |
| 2002/0128717 A1 | 9/2002 | Alfaro et al. |
| 2002/0147450 A1 | 10/2002 | LeHuec et al. |
| 2002/0169508 A1 | 11/2002 | Songer et al. |
| 2002/0193880 A1 | 12/2002 | Fraser |
| 2003/0045939 A1 | 3/2003 | Casutt |
| 2003/0078666 A1 | 4/2003 | Michelson |
| 2003/0078668 A1 | 4/2003 | Michelson |
| 2003/0125739 A1 | 7/2003 | Bagga et al. |
| 2003/0135277 A1 | 7/2003 | Bryan et al. |
| 2003/0153975 A1 | 8/2003 | Byrd |
| 2003/0167092 A1 | 9/2003 | Foley |
| 2003/0195626 A1 | 10/2003 | Huppert |
| 2003/0195632 A1 | 10/2003 | Foley et al. |
| 2003/0199983 A1 | 10/2003 | Michelson |
| 2004/0078078 A1 | 4/2004 | Shepard |
| 2004/0078081 A1 | 4/2004 | Ferree |
| 2004/0092929 A1 | 5/2004 | Zindrick |
| 2004/0093084 A1 | 5/2004 | Michelson |
| 2004/0102848 A1 | 5/2004 | Michelson |
| 2004/0126407 A1 | 7/2004 | Falahee |
| 2004/0133278 A1 | 7/2004 | Marino et al. |
| 2004/0143270 A1 | 7/2004 | Zucherman et al. |
| 2004/0176853 A1 | 9/2004 | Sennett et al. |
| 2004/0199254 A1 | 10/2004 | Louis et al. |
| 2004/0210219 A1 | 10/2004 | Bray |
| 2004/0210310 A1 | 10/2004 | Trieu |
| 2004/0210314 A1 | 10/2004 | Michelson |
| 2004/0249377 A1 | 12/2004 | Kaes et al. |

(56) References Cited

U.S. PATENT DOCUMENTS

| | | |
|---|---|---|
| 2004/0254644 A1 | 12/2004 | Taylor |
| 2005/0015149 A1 | 1/2005 | Michelson |
| 2005/0021143 A1 | 1/2005 | Keller |
| 2005/0033433 A1 | 2/2005 | Michelson |
| 2005/0049593 A1 | 3/2005 | Duong et al. |
| 2005/0049595 A1 | 3/2005 | Suh et al. |
| 2005/0065605 A1 | 3/2005 | Jackson |
| 2005/0065607 A1 | 3/2005 | Gross |
| 2005/0065608 A1 | 3/2005 | Michelson |
| 2005/0071008 A1 | 3/2005 | Kirschman |
| 2005/0085913 A1 | 4/2005 | Fraser et al. |
| 2005/0101960 A1 | 5/2005 | Fiere et al. |
| 2005/0149193 A1 | 7/2005 | Zucherman et al. |
| 2005/0154391 A1 | 7/2005 | Doherty et al. |
| 2005/0159813 A1 | 7/2005 | Molz |
| 2005/0159818 A1 | 7/2005 | Blain |
| 2005/0159819 A1 | 7/2005 | McCormick et al. |
| 2005/0171607 A1 | 8/2005 | Michelson |
| 2005/0177236 A1 | 8/2005 | Mathieu et al. |
| 2005/0240267 A1 | 10/2005 | Randall et al. |
| 2005/0240271 A1 | 10/2005 | Zubock et al. |
| 2005/0261767 A1 | 11/2005 | Anderson et al. |
| 2006/0020342 A1 | 1/2006 | Ferree et al. |
| 2006/0030851 A1 | 2/2006 | Bray et al. |
| 2006/0079901 A1 | 4/2006 | Ryan et al. |
| 2006/0079961 A1 | 4/2006 | Michelson |
| 2006/0085071 A1 | 4/2006 | Lechmann et al. ........ 623/17.11 |
| 2006/0089717 A1 | 4/2006 | Krishna |
| 2006/0129240 A1 | 6/2006 | Lessar et al. |
| 2006/0136063 A1 | 6/2006 | Zeegers |
| 2006/0142765 A9 | 6/2006 | Dixon et al. |
| 2006/0195189 A1 | 8/2006 | Link et al. |
| 2006/0206208 A1 | 9/2006 | Michelson |
| 2006/0229725 A1 | 10/2006 | Lechmann et al. |
| 2007/0088441 A1 | 4/2007 | Duggal et al. |
| 2007/0093819 A1 | 4/2007 | Albert |
| 2007/0106384 A1 | 5/2007 | Bray et al. |
| 2007/0118125 A1* | 5/2007 | Orbay et al. ................ 606/69 |
| 2007/0123987 A1 | 5/2007 | Bernstein |
| 2007/0162130 A1 | 7/2007 | Rashbaum et al. |
| 2007/0168032 A1 | 7/2007 | Muhanna et al. |
| 2007/0219635 A1 | 9/2007 | Mathieu et al. |
| 2007/0225806 A1 | 9/2007 | Squires et al. |
| 2007/0225812 A1 | 9/2007 | Gill |
| 2007/0250167 A1 | 10/2007 | Bray et al. |
| 2007/0270961 A1 | 11/2007 | Ferguson |
| 2008/0033440 A1 | 2/2008 | Moskowitz et al. |
| 2008/0051890 A1 | 2/2008 | Waugh et al. |
| 2008/0082169 A1 | 4/2008 | Gittings |
| 2008/0119933 A1 | 5/2008 | Aebi et al. |
| 2008/0133013 A1 | 6/2008 | Duggal et al. |
| 2008/0161925 A1 | 7/2008 | Brittan et al. |
| 2008/0177307 A1 | 7/2008 | Moskowitz et al. |
| 2008/0200984 A1 | 8/2008 | Jodaitis et al. |
| 2008/0249569 A1 | 10/2008 | Waugh et al. |
| 2008/0249575 A1 | 10/2008 | Waugh et al. ................ 606/305 |
| 2008/0249625 A1* | 10/2008 | Waugh et al. ............. 623/17.16 |
| 2008/0269806 A1 | 10/2008 | Zhang et al. |
| 2008/0275455 A1 | 11/2008 | Berry et al. |
| 2008/0306596 A1 | 12/2008 | Jones et al. |
| 2009/0076608 A1 | 3/2009 | Gordon et al. |
| 2009/0105830 A1 | 4/2009 | Jones et al. |
| 2009/0192613 A1 | 7/2009 | Wing et al. |
| 2009/0210062 A1 | 8/2009 | Thalgott et al. |
| 2009/0210064 A1 | 8/2009 | Lechmann et al. |
| 2009/0234455 A1 | 9/2009 | Moskowitz et al. |
| 2009/0326580 A1 | 12/2009 | Anderson et al. |
| 2010/0016901 A1 | 1/2010 | Robinson ..................... 606/289 |
| 2010/0125334 A1 | 5/2010 | Krueger |
| 2010/0145459 A1 | 6/2010 | McDonough et al. |
| 2010/0145460 A1 | 6/2010 | McDonough et al. |
| 2011/0118843 A1 | 5/2011 | Mathieu et al. |
| 2011/0295371 A1 | 12/2011 | Moskowitz et al. |
| 2012/0101581 A1 | 4/2012 | Mathieu et al. |
| 2012/0109309 A1 | 5/2012 | Mathieu et al. |
| 2012/0109311 A1 | 5/2012 | Mathieu et al. |
| 2012/0109312 A1 | 5/2012 | Mathieu et al. |
| 2012/0109313 A1 | 5/2012 | Mathieu et al. |
| 2012/0179259 A1 | 7/2012 | McDonough et al. |
| 2013/0073046 A1 | 3/2013 | Zaveloff et al. |
| 2013/0073047 A1 | 3/2013 | Laskowitz et al. |
| 2013/0166032 A1 | 6/2013 | McDonough et al. |
| 2013/0268008 A1 | 10/2013 | McDonough et al. |
| 2014/0025168 A1 | 1/2014 | Klimek et al. |
| 2014/0121777 A1 | 5/2014 | Rosen et al. |
| 2014/0180422 A1 | 6/2014 | Klimek et al. |
| 2014/0257487 A1 | 9/2014 | Lawson et al. |

FOREIGN PATENT DOCUMENTS

| | | |
|---|---|---|
| DE | 2821678 A | 11/1979 |
| DE | 30 42 003 A1 | 7/1982 |
| DE | 39 33 459 A1 | 4/1991 |
| DE | 42 42 889 A1 | 6/1994 |
| DE | 44 09 392 A1 | 9/1995 |
| DE | 4423257 | 1/1996 |
| DE | 195 04 867 C1 | 2/1996 |
| DE | 19504867 CI | 2/1996 |
| DE | 299 13 200 U1 | 9/1999 |
| DE | 202004020209 | 5/2006 |
| EP | 0179695 | 4/1986 |
| EP | 0505634 A1 | 9/1992 |
| EP | 0517030 A2 | 12/1992 |
| EP | 0517030 A3 | 4/1993 |
| EP | 0577178 A1 | 1/1994 |
| EP | 0639351 A2 | 2/1995 |
| EP | 0639351 A3 | 3/1995 |
| EP | 504346 B1 | 5/1995 |
| EP | 0517030 B1 | 9/1996 |
| EP | 0505634 B1 | 8/1997 |
| EP | 897697 A1 | 2/1999 |
| EP | 0966930 | 12/1999 |
| EP | 0968692 A1 | 1/2000 |
| EP | 0974319 A2 | 1/2000 |
| EP | 1033941 | 9/2000 |
| EP | 1051133 | 11/2000 |
| EP | 1103236 | 5/2001 |
| EP | 0906065 B1 | 1/2004 |
| EP | 1402836 | 3/2004 |
| EP | 1124512 | 9/2004 |
| EP | 1459711 | 7/2007 |
| EP | 1194087 | 8/2008 |
| FR | 2552659 | 4/1985 |
| FR | 2 697 996 | 5/1994 |
| FR | 2 700 947 | 8/1994 |
| FR | 2727003 | 5/1996 |
| FR | 2747034 A1 | 10/1997 |
| FR | 2 753 368 | 3/1998 |
| GB | 157668 A | 1/1921 |
| GB | 265592 A | 8/1927 |
| GB | 2 148 122 A | 5/1985 |
| GB | 2207607 | 2/1989 |
| GB | 2239482 A | 7/1991 |
| GB | 2266246 A | 10/1993 |
| JP | 3505416 | 11/1991 |
| JP | 9-280219 | 10/1997 |
| JP | 2006-513752 | 4/2006 |
| RU | 2229271 | 5/2004 |
| RU | 2244527 | 1/2005 |
| RU | 2307625 | 10/2007 |
| SU | 1465040 A1 | 3/1989 |
| WO | WO 88/03417 | 5/1988 |
| WO | WO 88/10100 | 12/1988 |
| WO | WO 90/00037 | 1/1990 |
| WO | WO 92/01428 | 2/1992 |
| WO | WO 92/06005 | 4/1992 |
| WO | WO 95/21053 | 8/1995 |
| WO | WO 96/39988 | 12/1996 |
| WO | WO 97/20526 | 6/1997 |
| WO | WO 97/23175 A | 7/1997 |
| WO | WO 97/25941 | 7/1997 |
| WO | WO 97/25945 | 7/1997 |
| WO | WO 97/39693 | 10/1997 |
| WO | WO 98/17209 | 4/1998 |

(56) References Cited

FOREIGN PATENT DOCUMENTS

| WO | WO 98/55052 | 12/1998 |
|---|---|---|
| WO | WO 98/56319 | 12/1998 |
| WO | WO 98/56433 | 12/1998 |
| WO | WO 99/009903 | 3/1999 |
| WO | WO 99/09903 | 3/1999 |
| WO | WO 99/27864 | 6/1999 |
| WO | WO 99/29271 | 6/1999 |
| WO | WO 99/32055 | 7/1999 |
| WO | WO 99/38461 | 8/1999 |
| WO | WO 99/38463 | 8/1999 |
| WO | WO 99/56675 | 11/1999 |
| WO | WO 99/63914 | 12/1999 |
| WO | WO 00/07527 | 2/2000 |
| WO | WO 00/07528 | 2/2000 |
| WO | WO 00/25706 | 5/2000 |
| WO | WO 00/30568 | 6/2000 |
| WO | WO 00/40177 | 7/2000 |
| WO | WO 00/41654 | 7/2000 |
| WO | WO 00/59412 | 10/2000 |
| WO | WO 00/66044 A1 | 11/2000 |
| WO | WO 00/66045 A1 | 11/2000 |
| WO | WO 00/74607 A1 | 12/2000 |
| WO | WO 01/08611 | 2/2001 |
| WO | WO 01/56497 A2 | 8/2001 |
| WO | WO 01/62190 A1 | 8/2001 |
| WO | WO 01/80785 | 11/2001 |
| WO | WO 01/56497 A3 | 12/2001 |
| WO | WO 01/93742 A2 | 12/2001 |
| WO | WO 01/95837 A1 | 12/2001 |
| WO | WO 01/56497 B1 | 3/2002 |
| WO | WO 01/93742 A3 | 9/2002 |
| WO | WO 2004/069106 | 8/2004 |
| WO | WO 2005/007040 A | 1/2005 |
| WO | WO 2005/020861 | 3/2005 |
| WO | WO 2006/138500 | 12/2006 |
| WO | WO 2007/098288 A2 | 8/2007 |
| WO | 2008/014258 | 1/2008 |
| WO | WO 2008/082473 | 7/2008 |
| WO | WO 2008/124355 | 10/2008 |
| WO | WO 2008/154326 | 12/2008 |
| WO | WO 2009/064644 | 5/2009 |
| WO | WO 2010/054181 | 5/2010 |
| WO | WO 2010/054208 | 5/2010 |
| WO | WO 2012/088238 | 6/2012 |

OTHER PUBLICATIONS

U.S. Appl. No. 11/199,599: Preliminary Amendment dated Jan. 9, 2008, 11 pages.
U.S. Appl. No. 11/199,599: Non-Final Office Action dated Apr. 1, 2009, 20 pages.
U.S. Appl. No. 11/199,599: Interview Summary including Draft Claim Amendments dated Sep. 24, 2009, 16 pages.
U.S. Appl. No. 11/199,599: Amendment dated Sep. 29, 2009, 30 pages.
U.S. Appl. No. 11/199,599: Final Office Action dated Dec. 24, 2009, 21 pages.
U.S. Appl. No. 11/199,599: Appeal Brief dated Apr. 15, 2010, 51 pages.
Chadwick et al., "Radiolucent Structural Materials for Medical Application", www.mddionline.com/print/238, Jun. 2001, accessed Jul. 31, 2012, 9 pages.
"Jury Trial Demanded", In The United States District Court for The District of Delaware, Case No. 1:11-cv-00652-LPSm filed Jul. 22, 2011, 8 pages.
*Appendix 1 to Joint Claim Construction Brief; Synthes' Exhibits A-9*, In The United States District Court for the District of Delaware Civil Action No. 1:11-cv-00652-LPS, Jun. 8, 2012, 192 pages.
*Appendix 2 to Joint Claim Construction Brief; Globus' Exhibits A-F,* In The United States District Court for the District of Delaware Civil Action No. 1:11-cv-00652-LPS, Jun. 8, 2012, 146 pages.
*Appendix 3 to Joint Claim Construction Brief; Exhibits A-C,* In The United States District Court for the District of Delaware Civil Action No. 1:11-cv-00652-LPS, Jun. 8, 2012, 38 pages.

Chadwick et al., "Radiolucent Structural Materials for Medical Applications," www.mddionline.com/print/238, Jun. 1, 2001, accsessed date Jul. 31, 2012, 9 pages.
*Expert Report of Dr. Domagoj Carie Regarding the Invalidity of U.S. Patent Nos. 7,846,207, 7,862,616 and 7,875,076,* In The United States District Court for the District of Delaware, Civil Action No. 1:11-cv-00652-LPS, Nov. 5, 2012, 149 pages.
*Expert Report of John F. Hall, M.D.,* United States District Court for the District of Delaware, Civil Action No. 1:11-cv-00652-LPS, Dec. 14, 2012, 27 pages.
*Expert Report of Paul Ducheyne, Ph.D. Concerning Patent Validity,* United States District Court District of Delaware, Civil Action No. 1:11-cv-00652-LPS, Dec. 13, 2012, 155 pages.
*Expert Report of Richard J. Gering, Ph.D., CLP* In The United States District Court for the District of Delaware, Civil Action No. 1:11-cv-00652-LPS, Dec. 14, 2012, 39 pages.
International Patent Application No. PCT/CH2003/00089, International Search Report dated Dec. 2, 2003, 3 pgs.
International Search Report, completed Aug. 16, 2007 for International Application No. PCT/US2007/005098, filed Feb. 27, 2007.
*Joint Claim Construction Brief,* In the United States District Court for the District of Delaware, Civil Action No. 1:11-cv-00652-LPS, Jun. 14, 2012, 97 pages.
Jonbergen et al., "Anterior CervicalInterbody fusion with a titanium box cage: Early radiological assessment of fusion and subsidence", The Spine Journal Jul. 5, 2005, 645-649.
Jury Verdict Form, United States District Court District of Delaware, Civil Action No. 1:11- cv-00652-LPS, Jun. 14, 2013, 20 pages.
Marcolongo et al., "Trends in Materials for Spine Surgery", Biomaterials and Clinical Use, 6, 2011, 21 pages.
*Memorandum Opinion,* United States District Court District of Delaware, Civil Action No. 1:11-cv-00652-LPS, May 7, 2013, 33 pages.
*Order,* United States District Court District of Delaware, Civil Action No. 1:11-cv-00652-LPS, May 15, 2013, 4 pages.
*Order,* United States District Court District of Delaware, Civil Action No. 1:11-cv-00652-LPS, May 7, 2013, 7 pages.
Parlov et al., Anterior Lumbar Interbody Fusion with Threaded Fusion Cages and Autologous Grafts, Eur. Spine J., 2000, 9, 224-229.
*Plaintiffs' Responses and Objections to Defendant Globus Medical, Inc.'s First Set of Interrogatories (Nos. 1-11),* United States District Court for the District of Delaware, Civil Action No. 1:11-cv-00652-LPS, Nov. 14, 2011, 18 pages.
*Plaintiffs' Supplemental Responses and Objections to Defendant Globus Medical Inc.'s Interrogatories Nos. 6-10 and Second Supplemental Responses and Objections to Interrogatory No. 5,* United States District Court for the District of Delaware, Civil Action No. 11-cv-652-LPS, Sep. 1, 2012, 12 pages.
Redacted version of "Defendant Globus Medical, Inc.'s Answering Brief in Opposition to Plaintiff's Motion for Summary Judgment of No Anticipation by the Kozak and Michelson References", Mar. 12, 2013, 233 pages.
Redacted version of "Opening Brief in Support of Plaintiffs' Motion for Summary Judgment of No Anticipation by the Kozak and Michelson References", United States District Court District of Delaware, Civil Action No. 1:11-cv-00652-LPS, Feb. 13, 2013, 66 pages.
Redacted version of "Plaintiff's Reply Brief in Support of Plaintiff's Motion for Summary Judgment of No Anticipation by the Kozak and Michelson References", Mar. 21, 2013, 11 pages.
*Reply Report of Dr. Domagoj Carie Regarding the Invalidity of U.S. Patent Nos. 7,846,207, 7,862,616 and 7,875,076,* In the United States District Court for the District of Delaware, Civil Action No. 1:11-cv-00652-LPS, Jan. 4, 2013, 81 pages.
Schleicher et al., "Biomechanical Comparison of Two Different Concepts for Stand alone anterior lumbar interbody fusion", Eur. Spine J., Sep. 2008, 17, 1757-1765.
Scholz et al., "A New Stand-Alone Cervical Anterior Interbody Fusion Device", Spine, Jan. 2009, 34(2), 6 pages.
*Second Expert Report of Wilson C. Hayes, Ph.D.,* United States District Court for the District of Delaware, Civil Action No. 1:11-cv-00652-LPS, Dec. 14, 2012, 22 pages.
Spruit et al., The in Vitro Stabilising Effect of Polyether-etherketone Cages Versus a Titanium Cage of similar design for anterior lumbar interbody fusion, Eur. Spine J., Aug. 2005, 14 752-758.

(56) References Cited

OTHER PUBLICATIONS

Trial Transcript, United States District Court District of Delaware, Civil Action No. 1:11-cv-00652-LPS, Jun. 10, 2013, 114 pages.
Trial Transcript, United States District Court District of Delaware, Civil Action No. 1:11-cv-00652-LPS, Jun. 11, 2013, 98 pages.
Trial Transcript, United States District Court District of Delaware, Civil Action No. 1:11-cv-00652-LPS, Jun. 12, 2013, 75 pages.
Trial Transcript, United States District Court District of Delaware, Civil Action No. 1:11-cv-00652-LPS, Jun. 13, 2013, 94 pages.
Trial Transcript, United States District Court District of Delaware, Civil Action No. 1:11-cv-00652-LPS, Jun. 14, 2013, 26 pages.
Trial Transcript, United States District Court District of Delaware, Civil Action No. 1:11-cv-00652-LPS, Jun. 3, 2013, 98 pages.
Trial Transcript, United States District Court District of Delaware, Civil Action No. 1:11-cv-00652-LPS, Jun. 4, 2013, 110 pages.
Trial Transcript, United States District Court District of Delaware, Civil Action No. 1:11-cv-00652-LPS, Jun. 5, 2013, 99 pages.
Trial Transcript, United States District Court District of Delaware, Civil Action No. 1:11-cv-00652-LPS, Jun. 6, 2013, 80 pages.
Trial Transcript, United States District Court District of Delaware, Civil Action No. 1:11-cv-00652-LPS, Jun. 7, 2013, 97 pages.
Japanese Patent Application No. 2011-534926: Office Action dated Oct. 30, 2013, 7 pages.
Japanese Patent Application No. 2011-534928: Office Action dated Sep. 30, 2013, 11 pages.
Russian Patent Application No. 2011-1122797: Decision to Grant dated Oct. 9, 2013, 20 pages.
U.S. Appl. No. 60/988,661, filed Nov. 16, 2007, Kueenzi et al.
U.S. Appl. No. 61/535,726, filed Sep. 16, 2011, Zaveloff.
Synthes Spine, "SynFix-LR System. Instruments and Implants for Stand-Alone Anterior Lumbar Interbody Fusion (ALIF)", Technique Guide dated 2008, pp. 2-40, Published by Synthes Spine (USA).
Synthes Spine, "Zero-P Instruments and Implants. Zero-Profile Anterior Cervical Interbody Fusion (ACIF) device", Technique Guide dated 2008, pp. 2-32, Published by Synthes Spine (USA).
Bray, "InterPlate Spine Fusion Device: Subsidence Control Without Stress Shielding", Orthopaedic Product News, Sep.-Oct. 2006, pp. 22-25.
International Search Report, Mailed Mar. 20, 2009, for PCT International Application No. PCT/US08/82473, filed Nov. 5, 2008.
Written Opinion, Mailed Mar. 20, 2009, for PCT International Application No. PCT/US08/82473, filed Nov. 5, 2008.
Synthes Spine, "CorticoCancellous ACF Spacer. An allograft space or anterior fusion of the cervical spine," brochure, Musculoskeletal Transplant Foundationm, 2003, 6 pages.
International Patent Application PCT/US2011/066421, International Search Report dated Jun. 14, 2012, 31 pages.

\* cited by examiner

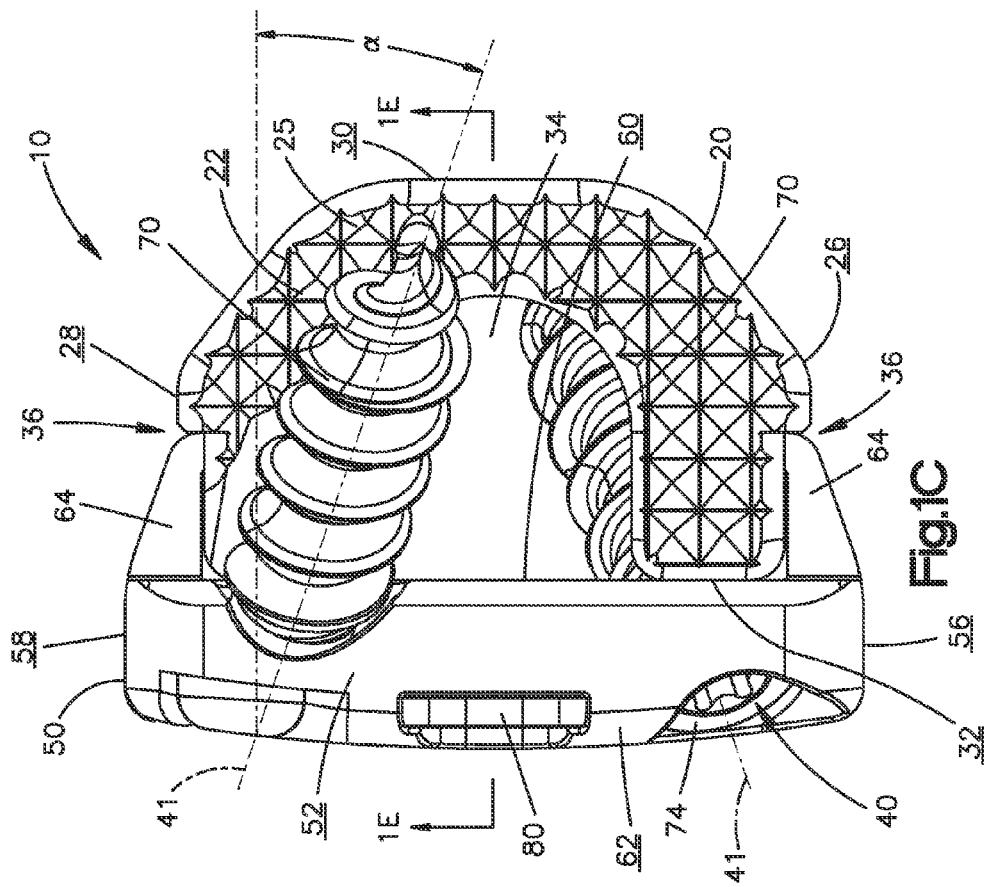
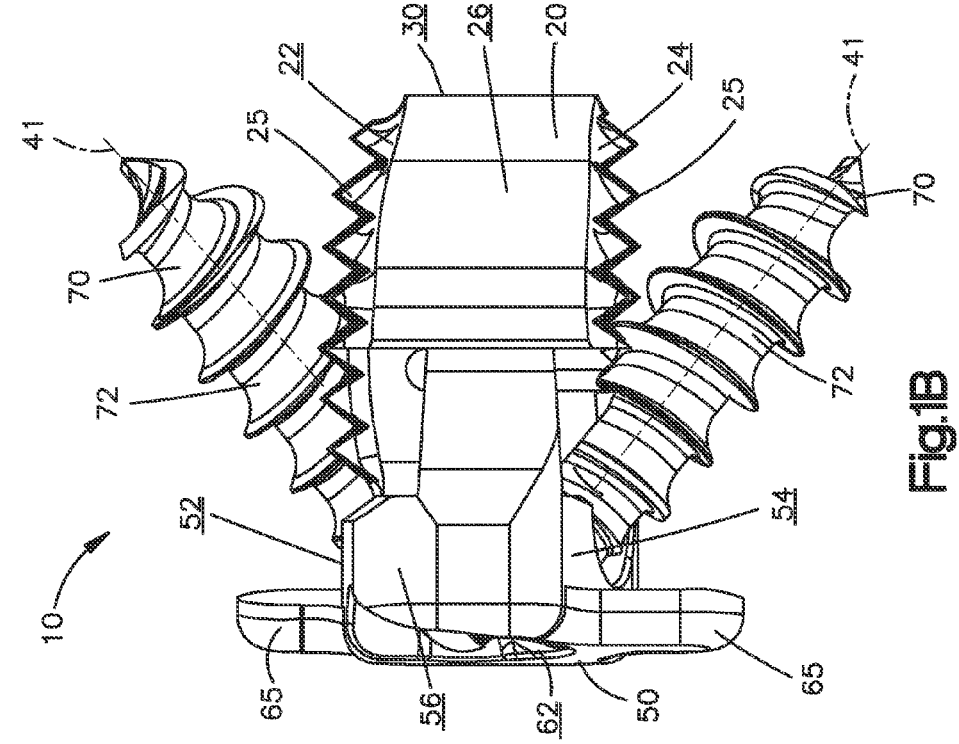

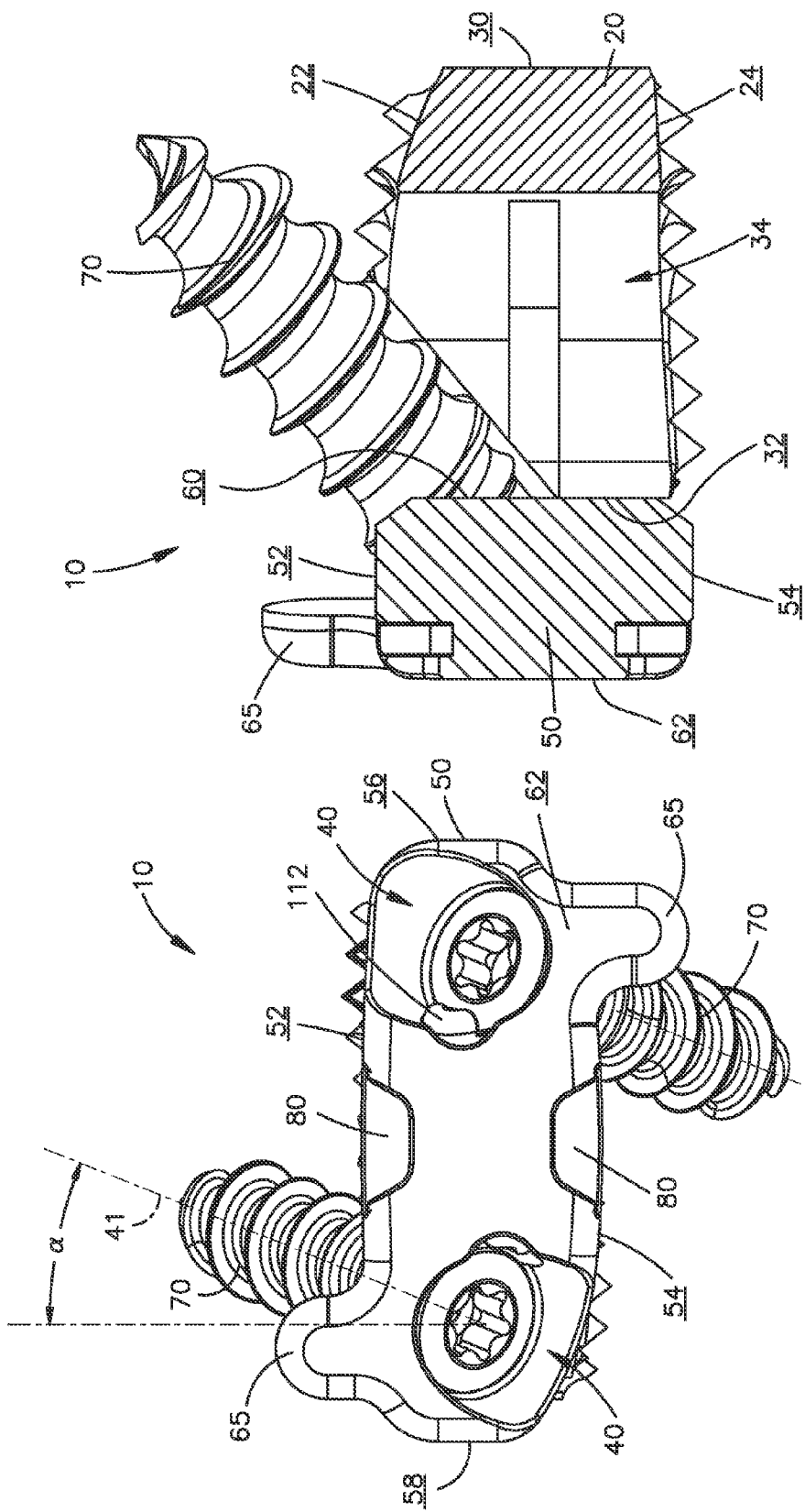

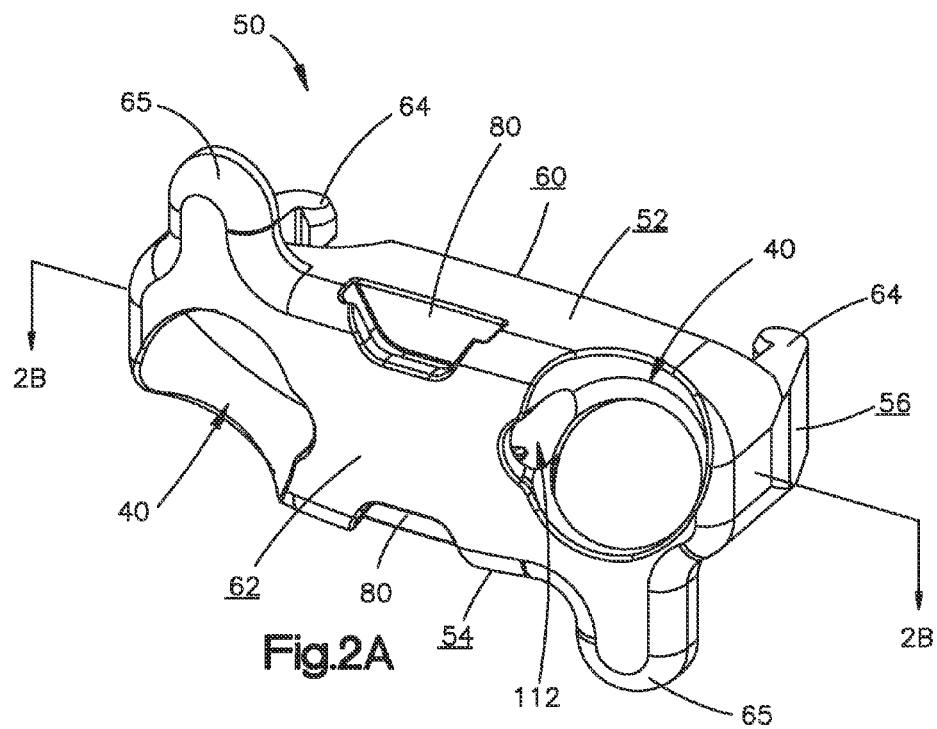
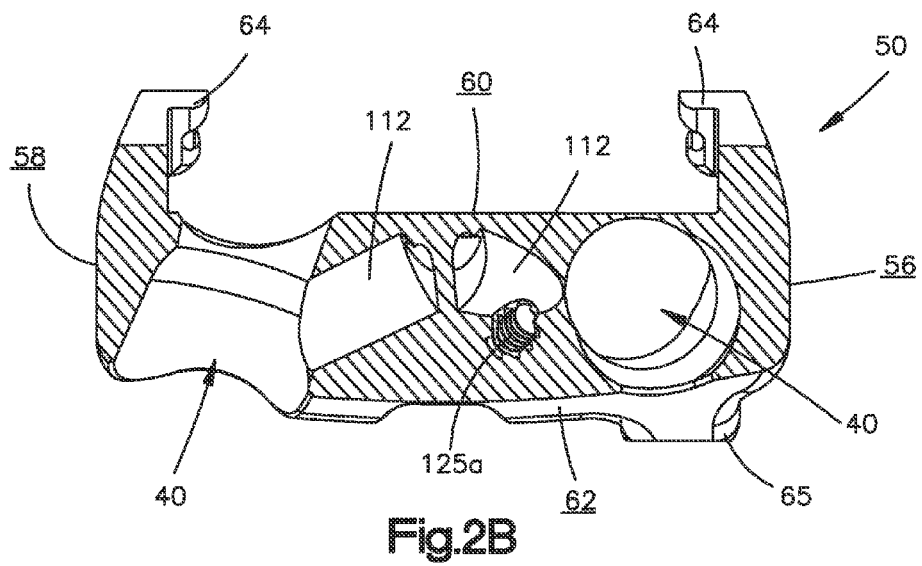

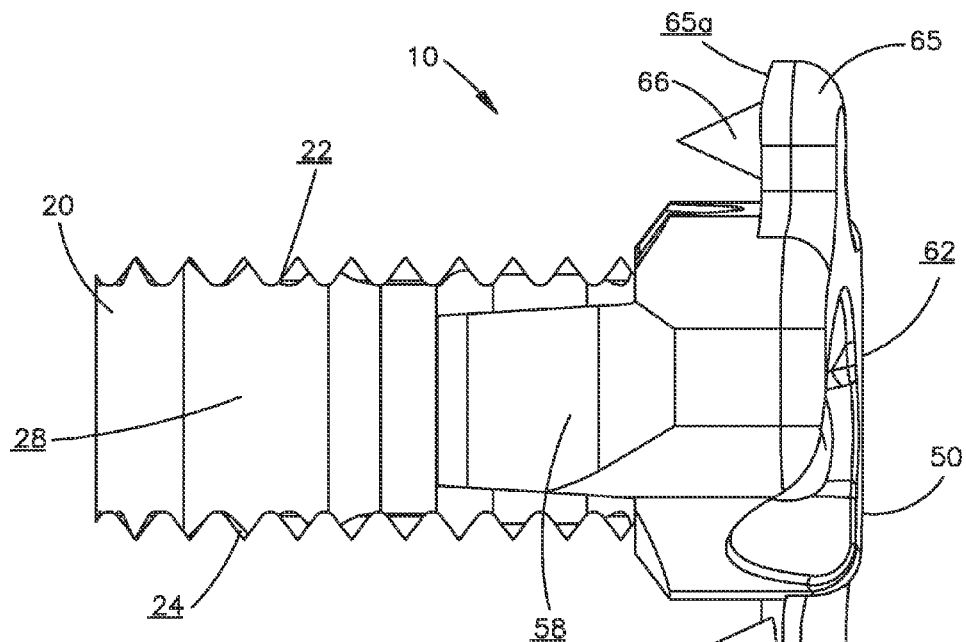
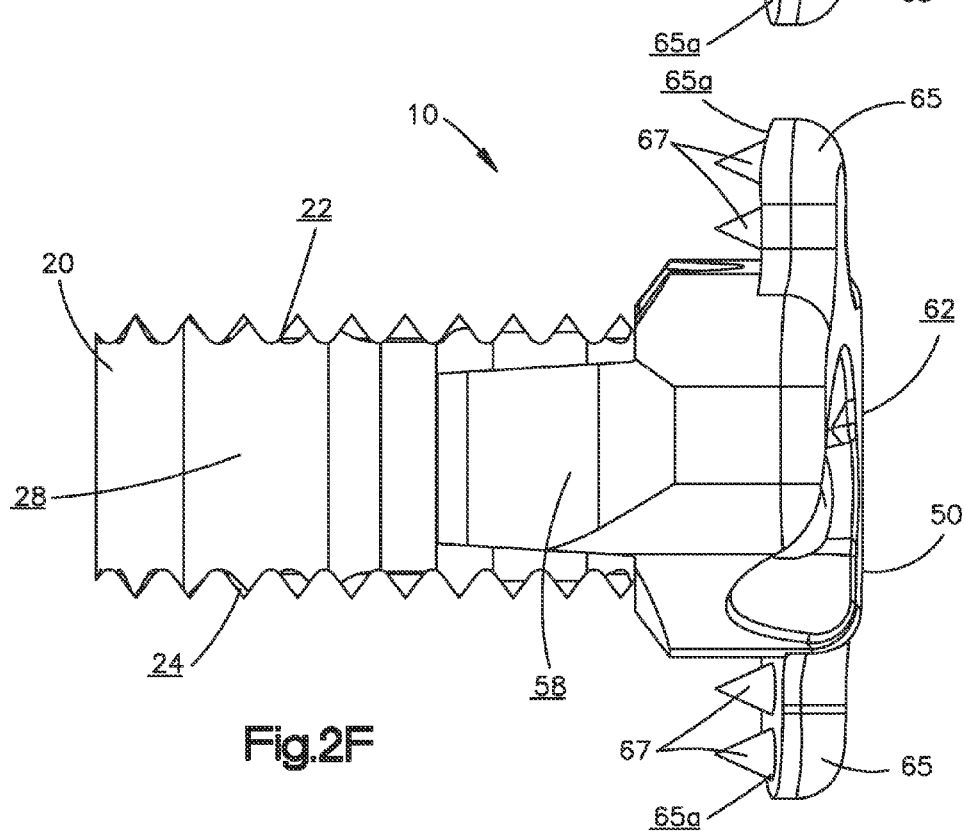

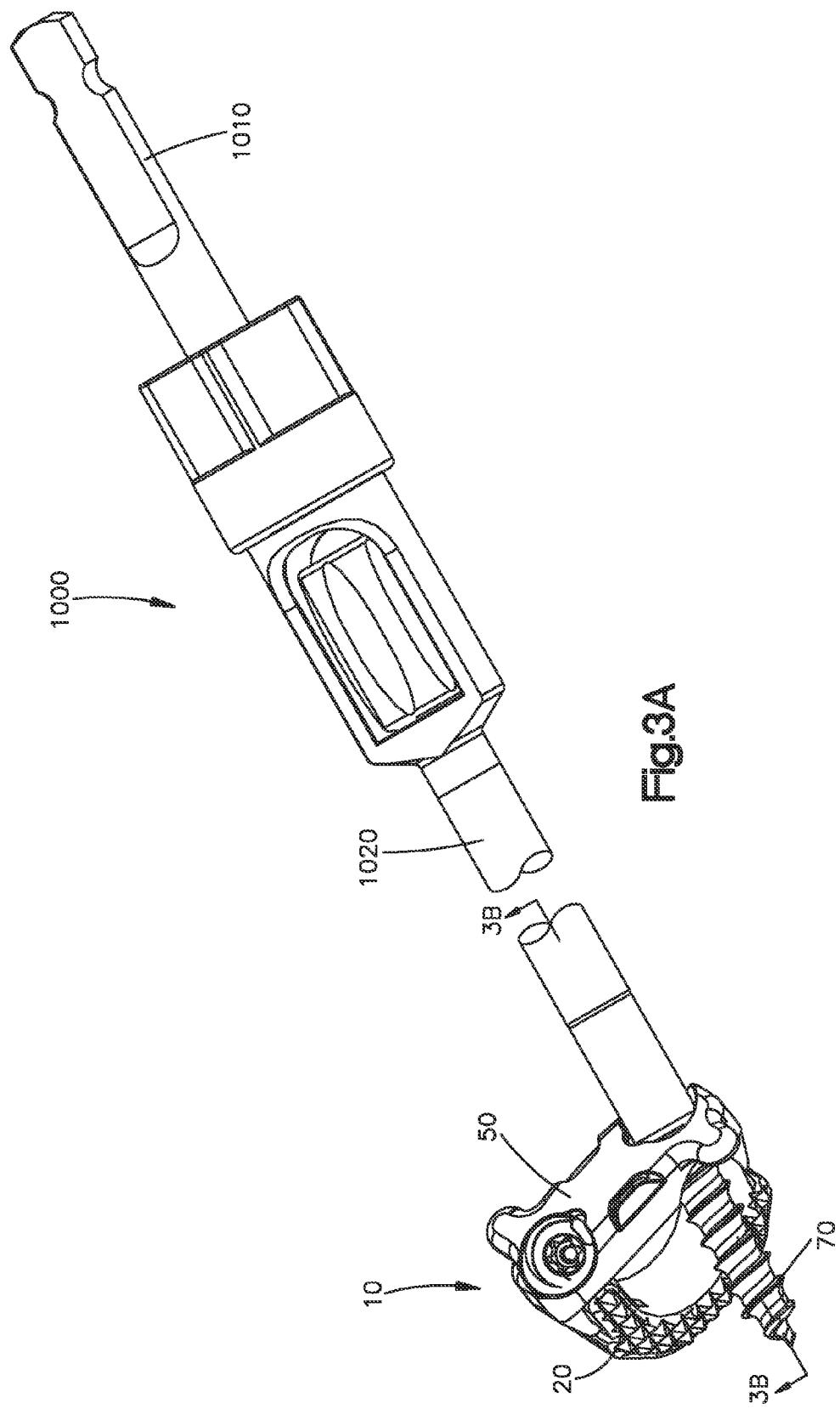

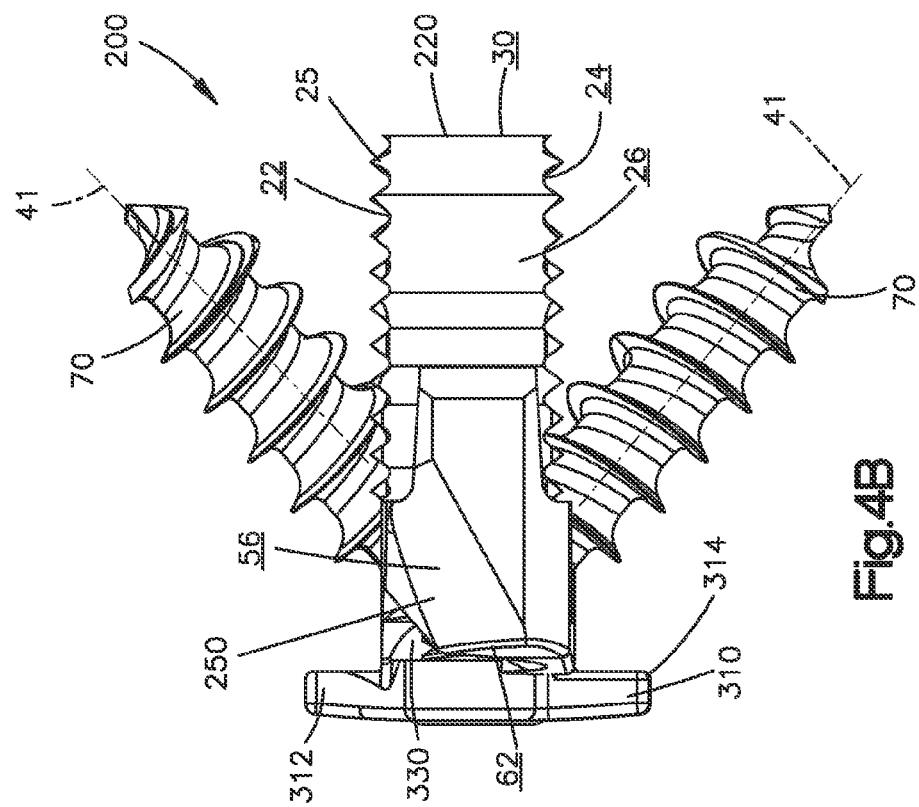
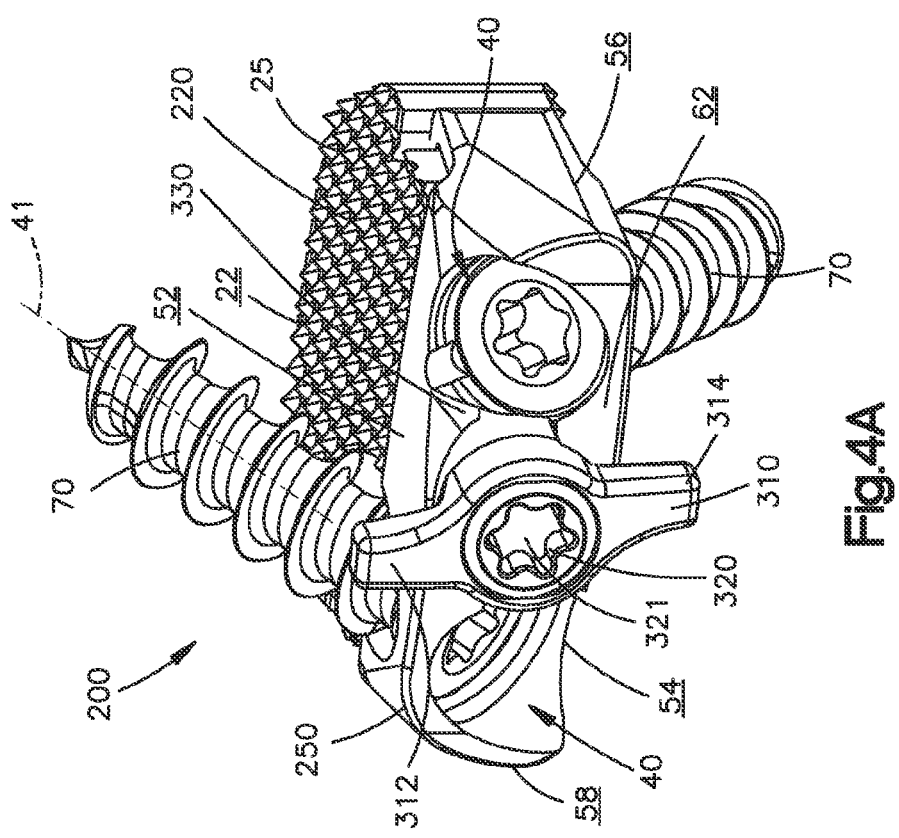

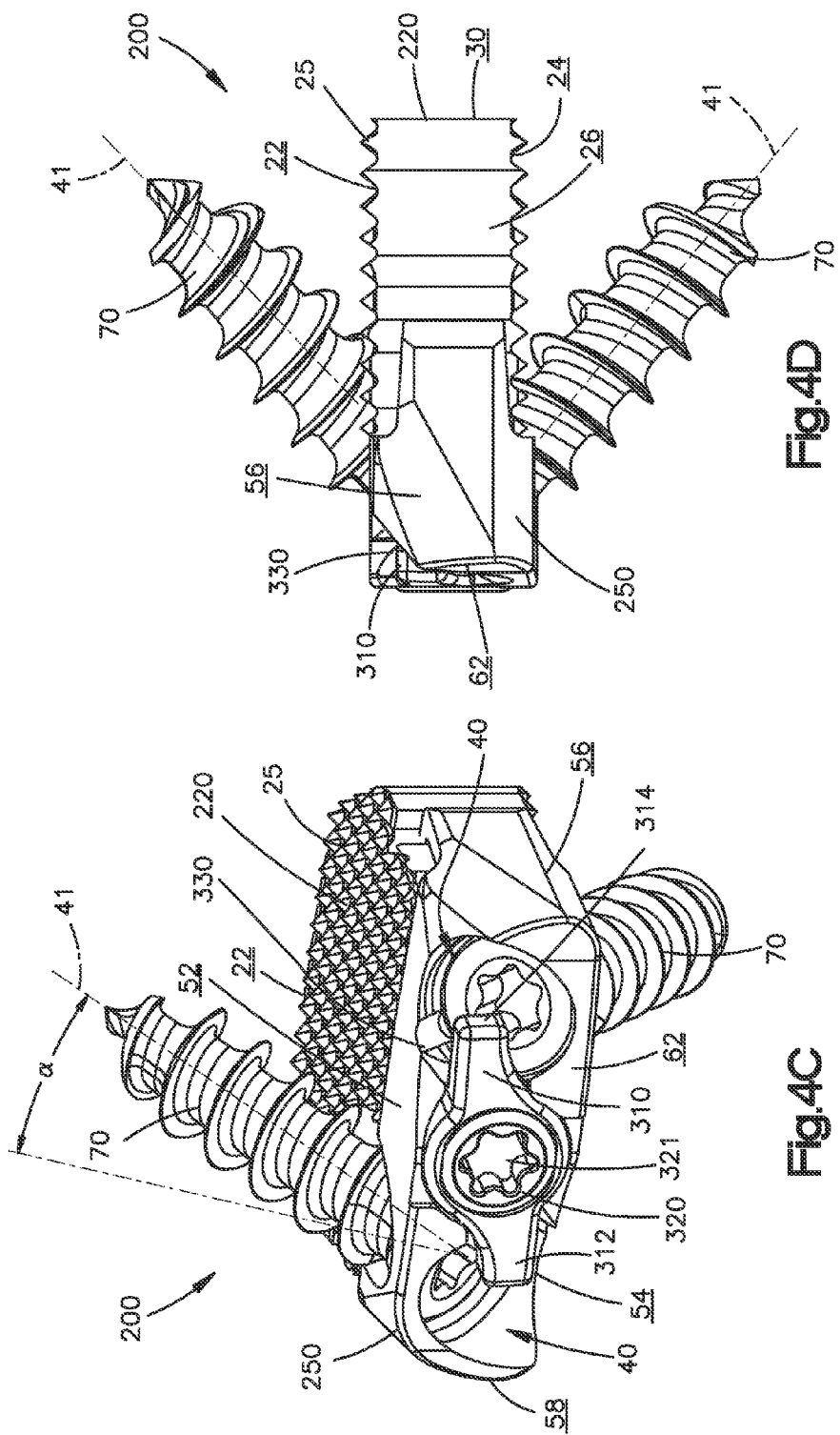

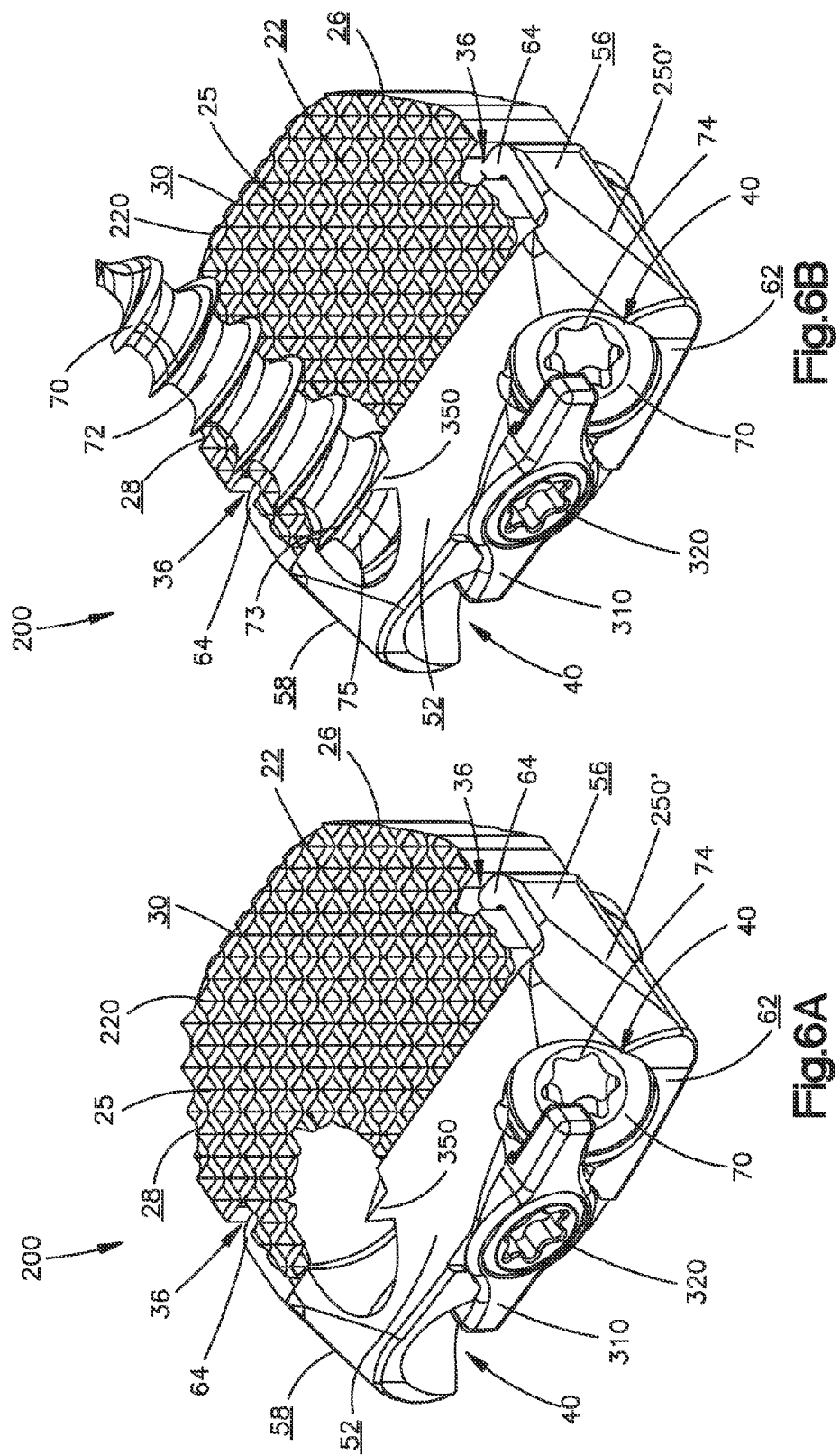

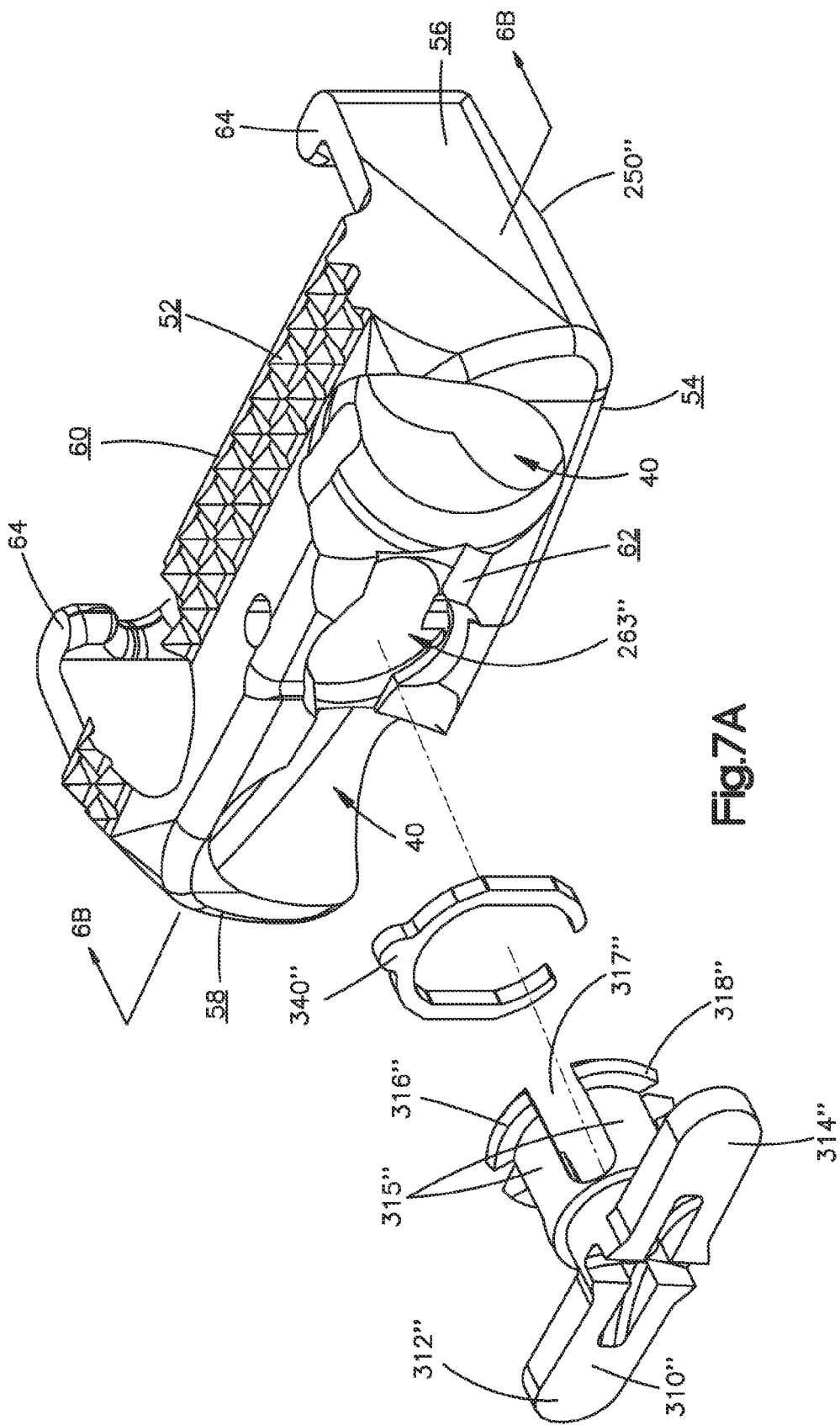

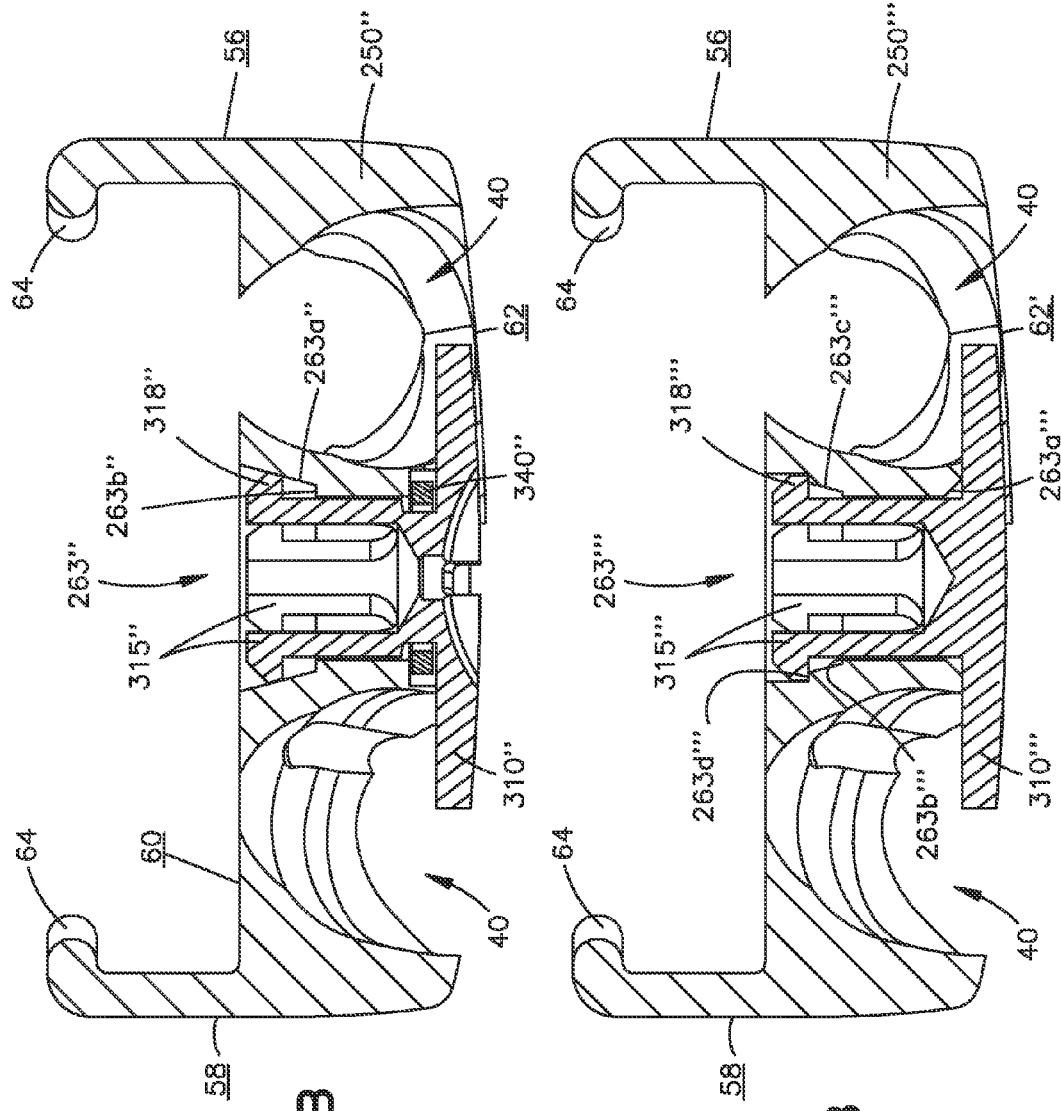

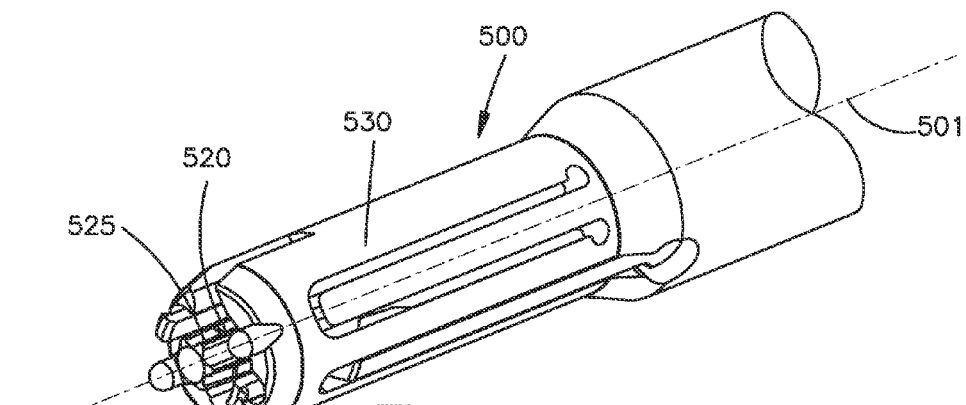
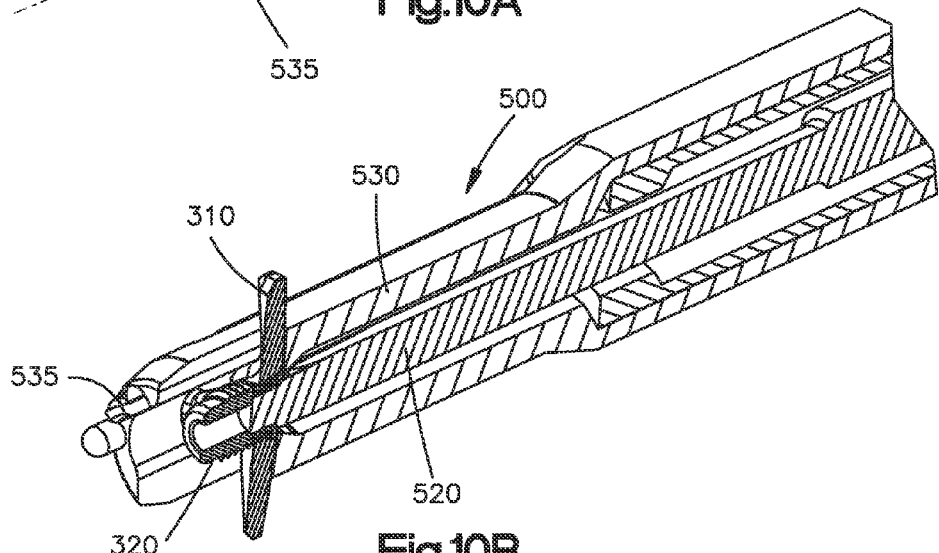
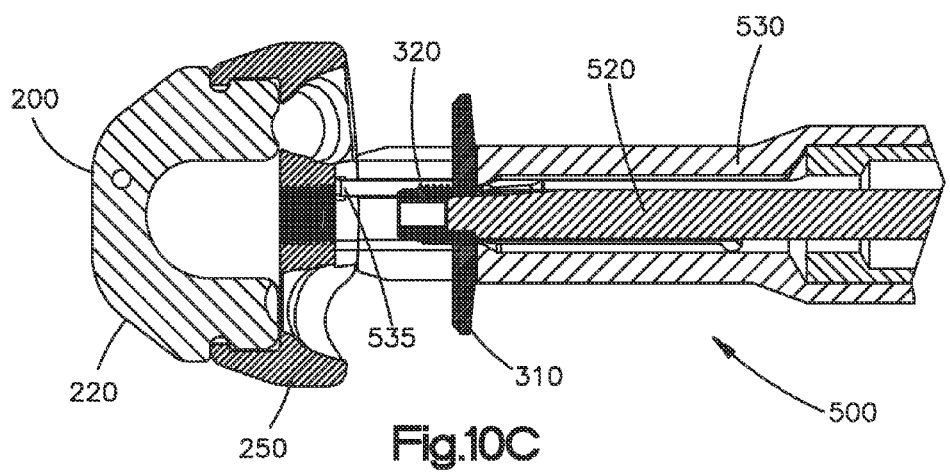

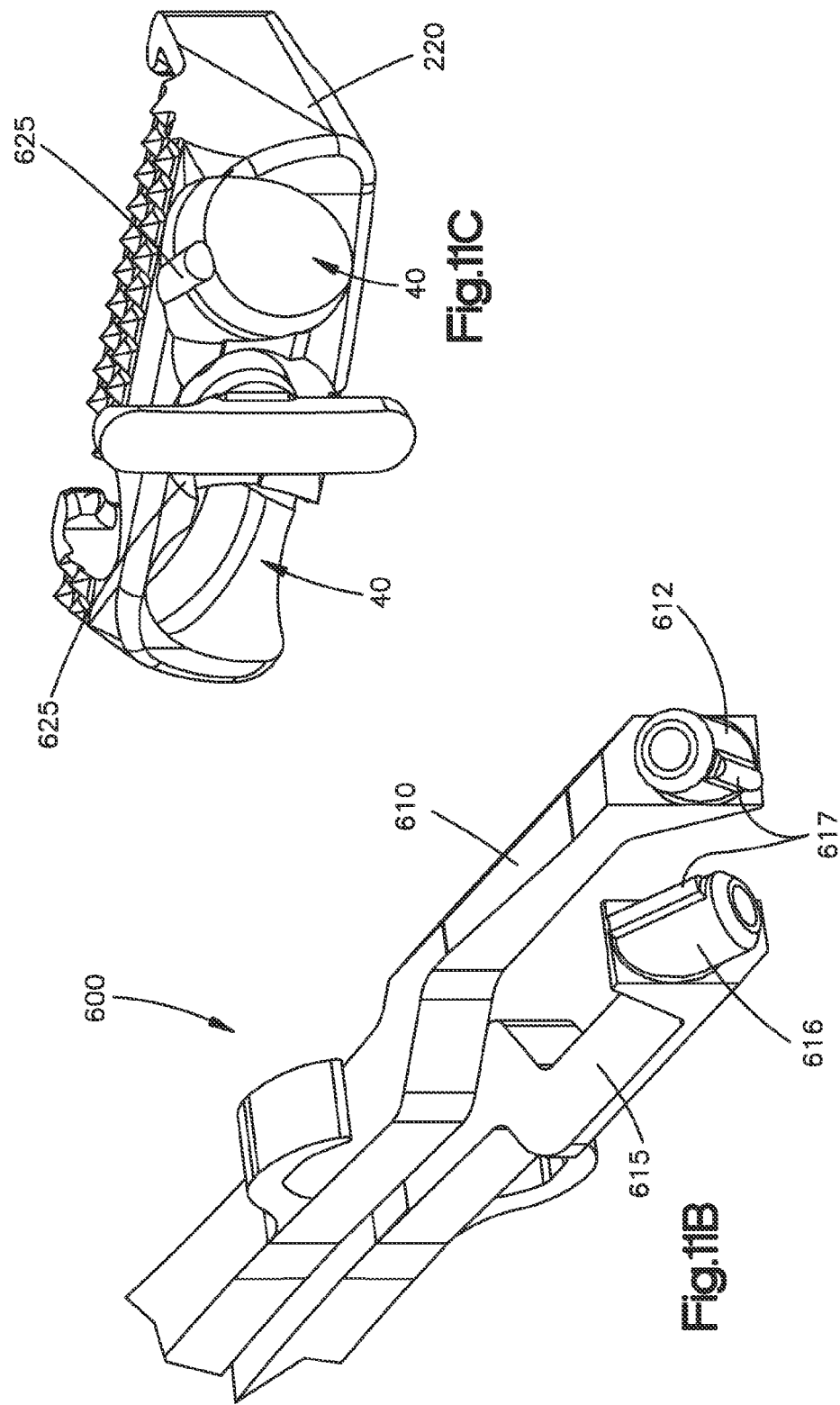

ZERO-PROFILE INTERBODY SPACER AND COUPLED PLATE ASSEMBLY

CROSS REFERENCE TO RELATED APPLICATIONS

This application claims priority to U.S. Provisional Patent Application No. 61/112,441, filed Nov. 7, 2008, entitled "Zero-Profile Interbody Spacer and Coupled Plate Assembly" and U.S. Provisional Patent Application No. 61/139,920, filed Dec. 22, 2008, entitled "Screw and Plate Locking Mechanisms for Smaller Bone Plates", the contents of which are hereby incorporated by reference in their entirety.

BACKGROUND OF THE INVENTION

Intervertebral implants including interbody spacer portions and mechanically coupled plate portions are known in the art for restoring disc height, allowing fusion to occur between the adjacent vertebral bodies, and for providing stable fixation during healing.

It is desirable to construct a zero-profile implant wherein bone fixation elements that secure the implant to the vertebral bodies are blocked from backing-out of the bone and/or plate.

Additionally, it is desirable to construct a zero-profile implant that includes polyaxial bone fixation element couplings and features that prevent the implant from being implanted too deeply into a prepared disc space. Both screw back-out and over-insertion of the implant into a prepared disc space can have an adverse impact on the performance of the implant.

BRIEF SUMMARY OF THE INVENTION

The present invention relates generally to a spinal implant. More specifically, the present invention relates to a zero profile interbody spacer and coupled plate assembly for insertion into a disc space between adjacent superior and inferior vertebral bodies. The implant preferably includes a spacer portion, a plate portion coupled to the spacer portion, a plurality of bone fixation elements for engaging the vertebral bodies and a retention mechanism for preventing the bone fixation elements from postoperatively uncoupling from the implant.

In one exemplary embodiment, the implant includes first and second bone fixation elements, a spacer portion, a plate portion coupled to the spacer portion, and first and second spring-biased snapper elements for preventing the first and second bone fixation elements from backing-out of bone fixation holes formed in the plate portion (e.g., from postoperatively uncoupling from the implant). The spacer portion preferably includes a top surface for contacting the superior vertebral body, a bottom surface for contacting the inferior vertebral body, a first side surface, a second side surface, a leading surface and a trailing surface.

The plate portion includes a top surface, a bottom surface, a first side surface, a second side surface, a leading surface, a trailing surface, first and second bone fixation holes and first and second boreholes. The first and second bone fixation holes are sized and adapted for receiving the first and second bone fixation elements, respectively. The first bone fixation hole is angled so that the first bone fixation element engages the superior vertebral body while the second bone fixation hole is angled so that the second bone fixation element engages the inferior vertebral body. The first borehole is in communication with the first bone fixation hole and the second borehole is in communication with the second bone fixation hole.

The first and second spring-biased snapper elements are located in the first and second boreholes, respectively. The first and second spring biased snapper elements are moveable from a first position to a second position. In the first position, at least a portion of the first and second snapper elements protrude into the first and second bone fixation holes, respectively, so that once the first and second bone fixation elements have been inserted into the first and second bone fixation holes, respectively, the first and second snapper elements at least partially cover the first and second bone fixation elements, respectively, to prevent backing-out. The first and second spring biased snapper elements are preferably biased to the first position.

Preferably, insertion of the first and second bone fixation elements causes a head portion of the first and second bone fixation elements to contact the first and second spring biased snapper elements, respectively, to cause the first and second spring biased snapper elements to recoil from their first positions to the their second positions. Thereafter, further insertion of the first and second bone fixation elements causes the head portions of the first and second bone fixation elements to move distally of the first and second spring biased snapper elements resulting in the first and second snapper elements automatically moving from their second position to their first position.

The implant preferably further includes first and second stops to prevent over-insertion of the implant during implantation and to assist in securing a position of the implant during insertion of the first and second bone fixation elements. The first stop preferably extends superiorly of the top surface of the plate portion for contacting the superior vertebral body while the second stop extends inferiorly of the bottom surface of the plate portion for contacting the inferior vertebral body. The first and second stops are preferably integrally formed with the plate portion.

In another exemplary embodiment, the implant preferably includes first and second bone fixation elements, a spacer portion, a plate portion coupled to the spacer portion and a propeller element for preventing the first and second bone fixation elements from backing-out and over-insertion of the plate portion. The spacer portion includes a top surface for contacting the superior vertebral body, a bottom surface for contacting the inferior vertebral body, a first side surface, a second side surface, a leading surface and a trailing surface.

The plate portion includes a top surface, a bottom surface, a first side surface, a second side surface, a leading surface, a trailing surface, and first and second bone fixation holes. The first and second bone fixation holes are sized and adapted for receiving the first and second bone fixation elements, respectively. The first bone fixation hole is angled so that the first bone fixation element engages the superior vertebral body while the second bone fixation hole is angled so that the second bone fixation element engages the inferior vertebral body.

The propeller preferably includes a longitudinal axis extending between a first end and a second end. The propeller is coupled to the plate portion in-between the first and second bone fixation holes. In use, the propeller is rotatable between a first position wherein the propeller does not interfere with first and second bone fixation holes so that the first and second bone fixation elements can be inserted into the first and second bone fixation holes, respectively, to a second position wherein the first end of the propeller at least partially covers at least a portion of the first bone fixation hole and the second end of the propeller at least partially covers at least a portion of the second bone fixation hole to prevent backing-out of the first and second bone fixation elements once implanted. The propeller is preferably rotated through a range of about ninety degrees (90°) from the first position to the second position. The propeller preferably includes a threaded screw for engaging a threaded borehole formed in the plate portion. In use, in the first position, the longitudinal axis of the propeller is preferably oriented generally parallel to an axis of the implant and parallel to a cranial-caudal axis of the vertebral bodies so that the first end of the propeller extends superiorly of the top surface of the plate portion and the second end of the propeller extends inferiorly of the bottom surface of the plate portion so that the propeller acts as a stop during implantation of the implant to prevent over-insertion and to assist in securing a position of the implant during insertion of the first and second bone fixation elements.

In another exemplary embodiment, the implant sized and adapted for insertion into an intervertebral disc space between superior and inferior vertebral bodies includes: (a) first and second bone fixation elements; (b) a spacer portion including a top surface for contacting the superior vertebral body, a bottom surface for contacting the inferior vertebral body, a first side surface, a second side surface, a leading surface and a trailing surface; and (c) a plate portion coupled to the spacer portion. The plate portion including a top surface, a bottom surface, a first side surface, a second side surface, a leading surface and a trailing surface. The plate portion further including first and second bone fixation holes and first and second boreholes, the first and second bone fixation holes sized and adapted for receiving the first and second bone fixation elements, respectively. The first bone fixation hole is angled so that the first bone fixation element engages the superior vertebral body while the second bone fixation hole is angled so that the second bone fixation element engages the inferior vertebral body. The first borehole is in communication with the first bone fixation hole and the second borehole is in communication with the second bone fixation hole. The implant further including first and second spring-biased snapper elements for preventing the first and second bone fixation elements, respectively, from backing out. The first spring biased snapper element is located in the first borehole and the second spring biased snapper element is located in the second borehole. The first and second spring biased snapper elements are moveable from a first position to a second position, in the first position, at least a portion of the first and second snapper elements protrude into the first and second bone fixation holes, respectively, so that once the first and second bone fixation elements have been inserted into the first and second bone fixation holes, respectively, the first and second snapper elements at least partially cover the first and second bone fixation elements, respectively, to prevent backing-out, the first and second spring biased snapper elements being biased to the first position.

The height of the plate portion is preferably substantially equal to a height of the spacer portion and a width of the plate portion is preferably substantially equal to a width of the spacer portion. The spacer portion preferably includes first and second recesses formed in the first and second side surfaces thereof, respectively, and the plate portion preferably includes first and second projections extending from the plate portion for engaging the first and second recesses.

Each of the first and second spring biased snapper elements preferably includes a spring and a snapper element. The snapper element preferably including a tapered first end that protrudes into the first and second bone fixation holes for interacting with the first and second bone fixation elements, respectively, and a second end for interacting with the spring. The first and second spring biased snapper elements are preferably secured within the first and second boreholes, respectively, via first and second pins, respectively.

In use, insertion of the first and second bone fixation elements preferably causes the first and second spring biased snapper elements to move from their respective first position to their respective second positions. Insertion of the first and second bone fixation elements preferably causes a head portion of the first and second bone fixation elements to contact the first and second spring biased snapper elements, respectively, to cause the first and second spring biased snapper elements to recoil from their first positions to the their second positions. Further insertion of the first and second bone fixation elements preferably causes the head portions of the first and second bone fixation elements to move distally of the first and second spring biased snapper elements resulting in the first and second snapper elements automatically moving from their second position to their first positions.

The implant preferably also includes first and second stops to prevent over insertion of the implant during implantation and to assist in securing a position of the implant during insertion of the first and second bone fixation elements, the first stop extending superiorly of the top surface of the plate portion for contacting the superior vertebral body, the second stop extending inferiorly of the bottom surface of the plate portion for contacting the inferior vertebral body. The first and second stops are preferably integrally formed with the plate portion.

In another exemplary embodiment, the implant sized and adapted for insertion into an intervertebral disc space between superior and inferior vertebral bodies includes (a) first and second bone fixation elements; (b) a spacer portion including a top surface for contacting the superior vertebral body, a bottom surface for contacting the inferior vertebral body, a first side surface, a second side surface, a leading surface and a trailing surface; and (c) a plate portion coupled to the spacer portion. The plate portion includes a top surface, a bottom surface, a first side surface, a second side surface, a leading surface, a trailing surface, and first and second bone fixation holes. The first and second bone fixation holes sized and adapted for receiving the first and second bone fixation elements, respectively. The first bone fixation hole is angled so that the first bone fixation element engages the superior vertebral body and the second bone fixation hole is angled so that the second bone fixation element engages the inferior vertebral body. The implant further including (d) a propeller element having a longitudinal axis extending between a first end and a second end. The propeller element being coupled to the plate portion in-between the first and second bone fixation holes. The propeller being rotatable between a first position wherein the propeller does not interfere with first and second bone fixation holes so that the first and second bone fixation elements can be inserted into the first and second bone fixation holes, respectively, to a second position wherein the first end of the propeller at least partially covers at least a portion of the first bone fixation hole and the second end of the propeller at least partially covers at least a portion of the second bone fixation hole to prevent backing out of the first and second bone fixation elements once implanted. In the first position, the longitudinal axis of the propeller is preferably oriented generally parallel to an axis of the implant so that the first end of the propeller extends superiorly of the top surface of the plate portion and the second end of the propeller extends inferiorly of the bottom surface of the plate portion so that the propeller acts as a stop during implantation of the implant to prevent over insertion of the implant and to assist in securing a position of the implant during insertion of the first and second bone fixation elements.

The propeller is preferably rotated through a range of about ninety degrees (90°) from the first position to the second position. The propeller preferably includes a threaded screw for engaging a threaded borehole formed in the plate portion. The trailing surface of the plate portion preferably includes tapered recesses that form guide ramps for the first and second ends of the propeller as the propeller is being rotated from the first position to the second position and so that in the second position, the propeller lies flush with the trailing surface of the plate portion.

BRIEF DESCRIPTION OF THE SEVERAL VIEWS OF THE DRAWINGS

The foregoing summary, as well as the following detailed description of preferred embodiments of the application, will be better understood when read in conjunction with the appended drawings. For the purposes of illustrating the implant of the present application, there is shown in the drawings preferred embodiments. It should be understood, however, that the application is not limited to the precise arrangements and instrumentalities shown. In the drawings:

FIG. 1B illustrates a side elevational view of the implant of FIG. 1A;

FIG. 1C illustrates a top plan view of the implant of FIG. 1A;

FIG. 1D illustrates an anterior elevational view of the implant of FIG. 1A;

FIG. 1E illustrates a cross-sectional view of the implant of FIG. 1A, taken along line 1E-1E of FIG. 1C;

FIG. 2A illustrates an anterior perspective view of a plate portion of the implant of FIG. 1A;

FIG. 2B illustrates a cross-sectional view of the plate portion of FIG. 2A, taken along line 2B-2B of FIG. 2A;

FIGS. 2E-2J illustrate various alternate views of the implant shown in FIG. 1A incorporating various alternate designs of a stop member configured for embedding at least partially into the vertebral bodies during impaction;

FIG. 3A illustrates a top plan view of an exemplary removal instrument for contacting and recoiling the retention mechanism of FIG. 2D to enable removal of the bone fixation elements from the implant;

FIG. 4A illustrates an anterior perspective view of an implant according to a second preferred embodiment of the present application, the retention mechanism being in a first position;

FIG. 4B illustrates a side elevational view of the implant shown in FIG. 4A, the retention mechanism being in the first position;

FIG. 4C illustrates an anterior perspective view of the implant shown in FIG. 4A, the retention mechanism being in a second position;

FIG. 4D illustrates a side elevational view of the implant shown in FIG. 4A, the retention mechanism being in the second position;

FIG. 6A illustrates a top perspective view of the implant shown in FIG. 4A, the plate portion incorporating an optional thread blocking mechanism;

FIG. 6B illustrates an alternate top perspective view of the implant shown in FIG. 6A illustrating the optional thread blocking mechanism in contact with an implanted bone fixation element;

FIG. 7A illustrates an anterior exploded perspective view of the plate portion used in connection with the implant of FIG. 4A, the retention mechanism incorporating a second exemplary coupling mechanism for engaging the plate portion;

FIG. 7B illustrates a cross-section view of the plate portion and retention mechanism shown in FIG. 7A, taken along line 7B-7B of FIG. 7A;

FIG. 8 illustrates a partial cross-sectional view of a plate portion used in connection with the implant of FIG. 4A, the retention mechanism incorporating a third exemplary coupling mechanism for engaging the plate portion;

FIGS. 10A-10E illustrate various views of an exemplary insertion instrument and method for inserting the implant of FIG. 4A; and FIGS. 11A-11C illustrate various views of an exemplary inserter and drill guide instrument for inserting an implant.

DETAILED DESCRIPTION OF THE INVENTION

Figure 1A:
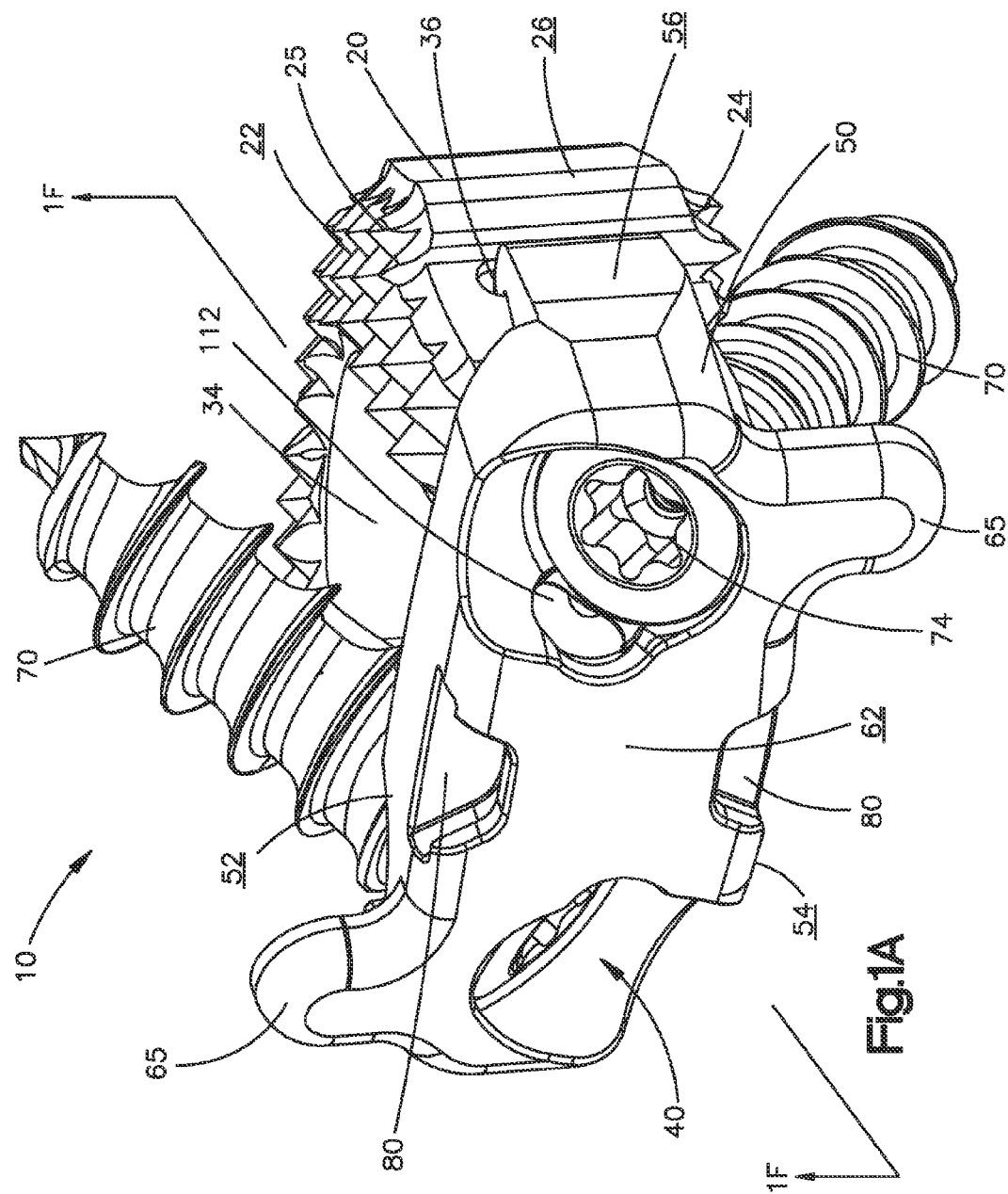
FIG. 1A illustrates an anterior perspective view of an implant according to a first preferred embodiment of the present application.
Figure 1F:
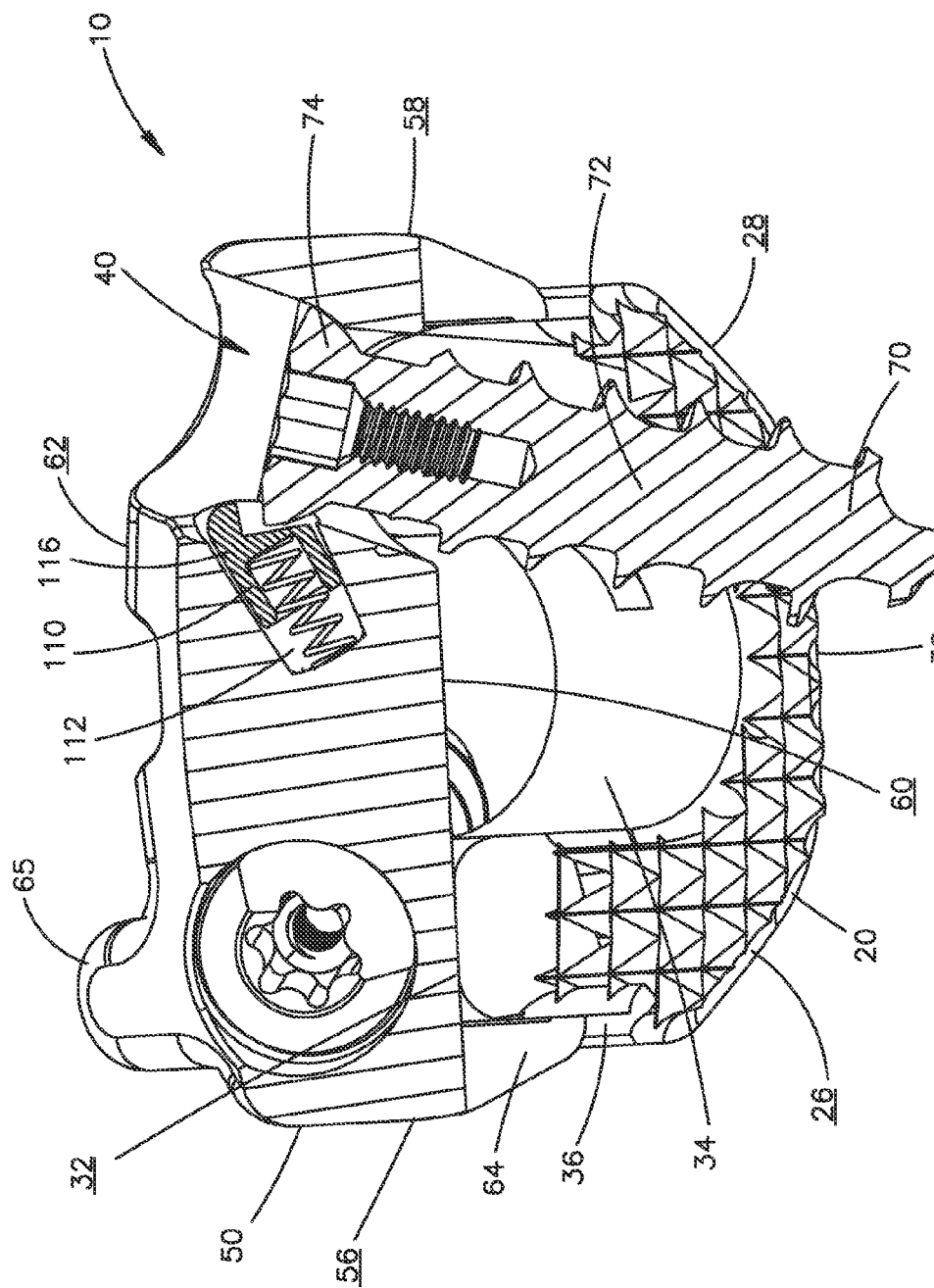
FIG. 1F illustrates a cross-sectional view of the implant of FIG. 1A, taken along line 1F-1F of FIG. 1A.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the implant and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

Similar reference numerals will be utilized throughout the application to describe similar or the same components of each of the preferred embodiments of the implant described herein and the descriptions will focus on the specific features of the individual embodiments that distinguish the particular embodiment from the others.

Preferred embodiments of the present application are directed to an implant 10, 200 ("10-200"). It should be understood that while the various embodiments of the implant 10-200 will be described in connection with spinal surgery, those skilled in the art will appreciate that the implant 10-200, as well as the components thereof, may be used for implantation into other parts of the body, including, for example, long bones or bones in knee, hip, shoulder, or other joint replacement or for bone augmentation.

The various embodiments of the implant 10-200 are preferably sized and configured to be implanted between adjacent vertebral bodies V. The implant 10-200 may be sized and configured to replace all or substantially all of an intervertebral disc space D between adjacent vertebral bodies V or only part of the intervertebral disc space D. In addition, the preferred implant 10-200 may be configured to replace an entire vertebral body V and related disc spaces D or multiple disc spaces D in a patient's spine, as would be apparent to one having ordinary skill in the art based upon a review of the present application. The implant 10-200 may be adapted for use in the anterior, antero-lateral, direct lateral, extra-foraminal, transforaminal, and posterior approaches for insertion into the spine.

The implant 10-200 of each of the preferred embodiments includes an interbody spacer portion 20, 220, 220' ("20-220") and a plate portion 50, 250, 250', 250", 250''' ("50-250"). The spacer portion 20-220 is preferably sized and configured for implantation into the intervertebral disc space D between adjacent vertebral bodies V. The spacer portion 20-220 of each of the preferred embodiments includes a top surface 22, a bottom surface 24, a first side surface 26, a second side surface 28, a leading surface 30 and a trailing surface 32. The top and bottom surfaces 22, 24 are suitable for contacting and are adapted for being secured relative to the end plates of adjacent vertebral bodies V. The spacer portion 20-220 is preferably sized and configured to maintain and/or restore a desired intervertebral disc height between the adjacent vertebral bodies V. Accordingly, the top and bottom surfaces 22, 24 may include a series of teeth, ridges, spikes or other similar projections 25 to aid in securing the implant 10-200 to the endplates of the adjacent vertebral bodies V.

The top and bottom surfaces 22, 24 may also include a curved or a tapered surface to help provide an anatomical shape for mating with the patient's spine or to orient the endplates of the adjacent vertebral bodies V in a desired manner. The particular surface shape and curvature, taper or alternate surface feature in the anterior-posterior direction, as well as the particular surface shape and curvature, taper or alternate surface feature in the medial-lateral direction will depend upon the location where the implant 10-200 is intended to be implanted and/or surgeon preferences or whether the implant 10-200 is utilized in another area in the body.

The spacer portion 20-220 may also include one or more spacer boreholes, openings, windows or channels 34 for receiving bone graft material. For example, the implant 10-200 may include one or more vertical openings, windows or channels extending through the spacer portion 20-220 from the top surface 22 to the bottom surface 24 for insertion of bone graft material, such that bone growth is promoted through the vertical openings, windows or channels 34 following implantation of the implant 10-200. One or more spacer boreholes, openings, windows or channels 34 is especially preferred if the spacer portion 20-220 is constructed of a non-allograft or non-bone-growth material, such as Polyetheretherketone ("PEEK").

The plate portion 50-250 is preferably coupled to the spacer portion 20-220 to provide increased implant stability during healing as well as to optimally orient the trajectory of bone fixation elements 70 during implantation.

The plate portion 50-250 of each of the preferred embodiments includes a top surface 52, a bottom surface 54, a first side surface 56, a second side surface 58, a leading surface 60 and a trailing surface 62. The plate portion 50-250 preferably contacts the trailing surface 32 of the spacer portion 20-220 and preferably does not extend beyond or does not increase greatly the vertical or lateral perimeter of the spacer portion 20-220. In this manner, the implant 10-200 has a low profile. Additionally, in this manner, the plate portion 50-250 is preferably entirely implanted within the intervertebral disc space D between the adjacent vertebral bodies V such that the plate portion 50-250 has little or no external profile (e.g., the plate portion 50-250 does not extend anterior beyond an edge of the disc space D). In this manner, little or no structure protrudes outside of the bounds of the disc space D or the profile of the vertebral bodies V, thereby limiting dysphasia and patient discomfort. In use, the plate portion 50-250 may be sized and configured so that the top and bottom surfaces 52, 54 of the plate portion 50-250 contact the endplates of the adjacent vertebral bodies V. Alternatively, the plate portion 50-250 may be sized and configured so that only the spacer portion 20-220 contacts the adjacent vertebral bodies V. For example, the height of the plate portion 50-250 may be small enough so that it does not contact the vertebral bodies V when connected to the spacer portion 20-220 in an implanted position.

The plate portion 50-250 may be coupled to the spacer portion 20-220 by any coupling mechanism now or hereafter known. For example, the spacer portion 20-220 may include one or more recesses 36 formed in the side or trailing surfaces for engaging one or more projections 64 extending from the plate portion 50-250. Preferably the spacer portion 20 includes a recess 36 formed in each of the side surfaces 26, 28 thereof for engaging projections 64 extending from the plate portion 50-250. The recesses 36 may extend completely from the top surface 22 to the bottom surface of the spacer portion 20 or may extend only partially from either the top or bottom surface 20, 22. Other coupling mechanisms for coupling the plate portion 50-250 to the spacer portion 20-220 are disclosed in International Application No. PCT/US2008/082473 filed on Nov. 5, 2008 and entitled, "Low Profile Intervertebral Implant", the contents of which are hereby incorporated by reference in their entirety.

The trailing surface 62 of the plate portion 50-250 preferably includes a tool engagement feature 80 for engaging one or more insertion tools. The tool engagement feature 80 may be in any form now or hereafter known for such purpose including one or more recesses formed in the trailing surface 62 of the plate portion 50-250, the recesses extending from top and bottom surfaces 52, 54, respectively, for engaging arms of the insertion tool. Alternatively, the tool engagement feature 80 may be a threaded bore (not shown) formed in the trailing surface 62 of the plate portion 50-250 for engaging a threaded stem extending from the insertion tool, etc.

The implant 10-200 preferably includes one or more bone fixation holes 40 for receiving one or more bone fixation elements 70, preferably bone screws so that, in use, after the implant 10-200 has been inserted into the intervertebral disc space D between adjacent vertebral bodies V, the implant 10-200 may be secured to the adjacent vertebral bodies V. The bone fixation elements 70 preferably include a threaded shaft 72 and a partially spherical head portion 74 that is generally smooth where it contacts the bone fixation hole 40. The threaded shaft 72 may be self-drilling, i.e. does not necessitate the drilling of pilot holes, but are not so limited. The bone fixation elements 70 are not limited to bone screws 70 and may be comprised of a helical nail, a distally expanding nail or screw, etc. The bone fixation holes 40 are preferably sized and configured so that the head portion 74 of the bone fixation elements 70 do not protrude proximally beyond the trailing surface 62 of the plate portion 50, when the bone fixation elements 70 have been fully implanted.

The bone fixation holes 40 preferably include a curved or frusta-spherical surface for contacting an underside of the generally smooth or frusta-spherical surface of the head portion 74 of the bone fixation elements 70 so that the bone fixation elements 70 can polyaxially rotate with respect to the plate portion 50-250 and a variety of trajectory angles can be chosen for the bone fixation elements 70 according to surgeons' preferences or needs as well as to enable the implant 10-200 to settle during healing.

The plate portion 50-250 preferably includes first and second bone fixation holes 40 for receiving first and second bone fixation elements 70 with the first bone fixation element 70 being angled upwardly for engaging the superior vertebral body V and the second bone fixation element 70 being angled downwardly for engaging the inferior vertebral body V. That is, the bone fixation holes 40 preferably have a longitudinal axis 41 that is oriented obliquely with respect to the implant 10-200 so that the bone fixation elements 70 form a fastener angle with respect to the top and bottom surfaces 22, 24 of the spacer portion 20 wherein bone fixation angle may be in the range between twenty degrees (20°) and sixty degrees (60°), and more preferably between thirty degrees (30°) and fifty degrees (50°). The bone fixation angle may be the same for all of the holes 40 or may be different for each of the holes 40. In addition, the bone fixation holes 40 may be directed inwardly toward the center of the implant 10-200 or outwardly away from the center of the implant 10-200, preferably at a lateral bone fixation angle α so that the bone fixation elements 70 extend laterally inward toward a center plane of the implant 10-200 or laterally outward away from the center plane of the implant 10-200. The lateral bone fixation angle α may be in the range between plus sixty degrees (60°) and minus sixty degrees (−60°), preferably between zero degrees (0°) and plus or minus thirty degrees (30°), and more preferably about plus or minus fifteen degrees (15°). The lateral bone fixation angle α may be the same for all holes 40 or may be different for each hole 40. However, as would be understood by one of ordinary skill in the art based upon a reading of this disclosure, a plurality of potential angles is possible since the bone fixation elements 70 are polyaxial, as will be described in greater detail below.

It should be understood however that the implant 10-200 may include three, four, five or more bone fixation holes 40 configured to receive a corresponding number of bone fixation elements 70 in any number of configurations. In addition, the number of bone fixation elements 70 extending from the top and bottom surfaces 22, 24 may be varied and the number of bone fixation elements 70 extending from the top surface 22 need not equal the number of bone fixation elements 70 extending from the bottom surface 24.

Exit openings for the bone fixation holes 40 preferably are formed at least partially in the top or bottom surfaces 52, 54 of the plate portion 50-250. The exit openings may also be formed at least partially or entirely in the top or bottom surfaces 22, 24 of the spacer portion 20-220. The bone fixation holes 40 may also include a partially spherical interior volume to accommodate the partially spherical geometry of the head portion 74 of the bone fixation elements 70 to enable a range of polyaxial orientations to be chosen for the bone fixation elements 70 with respect to the vertebral bodies V.

The implant 10-200 preferably also includes a retention mechanism for reducing the likelihood that the bone fixation elements 70 may postoperatively uncouple from the implant 10-200 and migrate from the disc space D. In use, the retention mechanism preferably covers at least a portion of the bone fixation holes 40 and hence the bone fixation elements 70 to prevent the bone fixation elements 70 from backing-out, as will be described in greater detail below.

The implant 10-200 including the spacer portion 20-220 and the plate portion 50-250 may be constructed of any suitable biocompatible material or combination of materials including, but not limited to one or more of the following metals such as titanium, titanium alloys, stainless steel, aluminum, aluminum alloy, magnesium, etc., polymers such as, PEEK, porous PEEK, carbon fiber PEEK, resorbable polymers, PLLA, etc., allograft, synthetic allograft substitute, ceramics in the form of bioglass, tantalum, Nitinol, or alternative bone growth material or some composite material or combination of these materials.

The spacer portion 20-220 may be formed of a different material than the plate portion 50-250. For example, the plate portion 50-250 may be formed of a metallic material such as, a titanium or a titanium alloy, and the spacer portion 20-220 may be formed of a non-metallic material such as, a polymer such as, PEEK, an allograft, a bioresorbable material, a ceramic, etc. Alternatively, the plate portion 50-250 and the spacer portion 20-220 may be formed from the same material. In addition, the plate portion 50-250 and spacer portion 20-220 may be integrally formed, pre-assembled or separately provided to a surgeon and assembled in the operating room.

As will be appreciated by one of ordinary skill in the art, the implant 10-200, or portions thereof, may also be coated with various compounds to increase bony on-growth or bony in-growth, to promote healing or to allow for revision of the implant 10-200, including hydroxyapatite, titanium-nickel, vapor plasma spray deposition of titanium, or plasma treatment to make the surface hydrophilic.

Referring to FIGS. 1A-2J, the intervertebral implant 10 of a first preferred embodiment includes the spacer portion 20, the plate portion 50, first and second bone fixation elements 70 and the retention mechanism. In the first preferred embodiment, the retention mechanism is in the form of a spring biased snapper element 110. More preferably, the plate portion 50 includes a borehole 112 in communication with each of the bone fixation holes 40 for receiving a spring 114 and a snapper element 116. The borehole 112 defines a longitudinal axis that intersects the longitudinal axis 41 of the bone fixation hole 40 and hence the bone fixation element 70. The intersection angle may be transverse, perpendicular or acute.

The snapper 116 preferably includes a first end 118 for contacting or interacting with the head portion 74 of the bone fixation element 70 and a second end 120 for receiving, contacting or interacting with the spring 114. The spring 114 is preferably sized and configured to bias the snapper 116 so that the snapper 116 protrudes into the bone fixation hole 40 and over the head portion 74 of the bone fixation element 70, once the bone fixation element 70 has been inserted into the bone fixation hole 40 to prevent back-out. The spring-biased snapper 116 is preferably secured within the borehole 112 via a pin or set screw 125. That is, the snapper 116 may include a groove or a recess 126 formed therein for mating with a pin or set screw 125, which is located within a borehole 125a. The interaction of the pin or set screw 125 and the groove or recess 126 preventing the snapper 116 from falling out of the borehole 112. For example, the snapper 116 preferably includes a rounded milled slot 126 and the pin or set screw 125 may be threaded and preferably includes a form fit so that the snapper 116 may be received and caught inside of the slot 126 formed in the snapper 116. Other mechanism for securing the spring-biased snapper 116 to the plate portion 50 may be used.

In the first preferred embodiment, the plate portion 50 also includes first and second stops 65, wherein the first stop 65 protrudes superiorly from the top surface 52 of the plate portion 50 for contacting the superior vertebral body V and the second stop 65 protrudes inferiorly from the bottom surface 54 of the plate portion 50 for contacting the inferior vertebral body V. Incorporation of more or less stops 65 is envisioned. Incorporation of the first and second stops 65 facilitates fully seating the implant 10 with respect to the adjacent vertebral bodies V regardless of the irregular anatomy of a patient's spine, which often characterizes the outer surface of the vertebral bodies V. The stops 65 are preferably integrally formed on the plate portion 50.

Figure 2C:
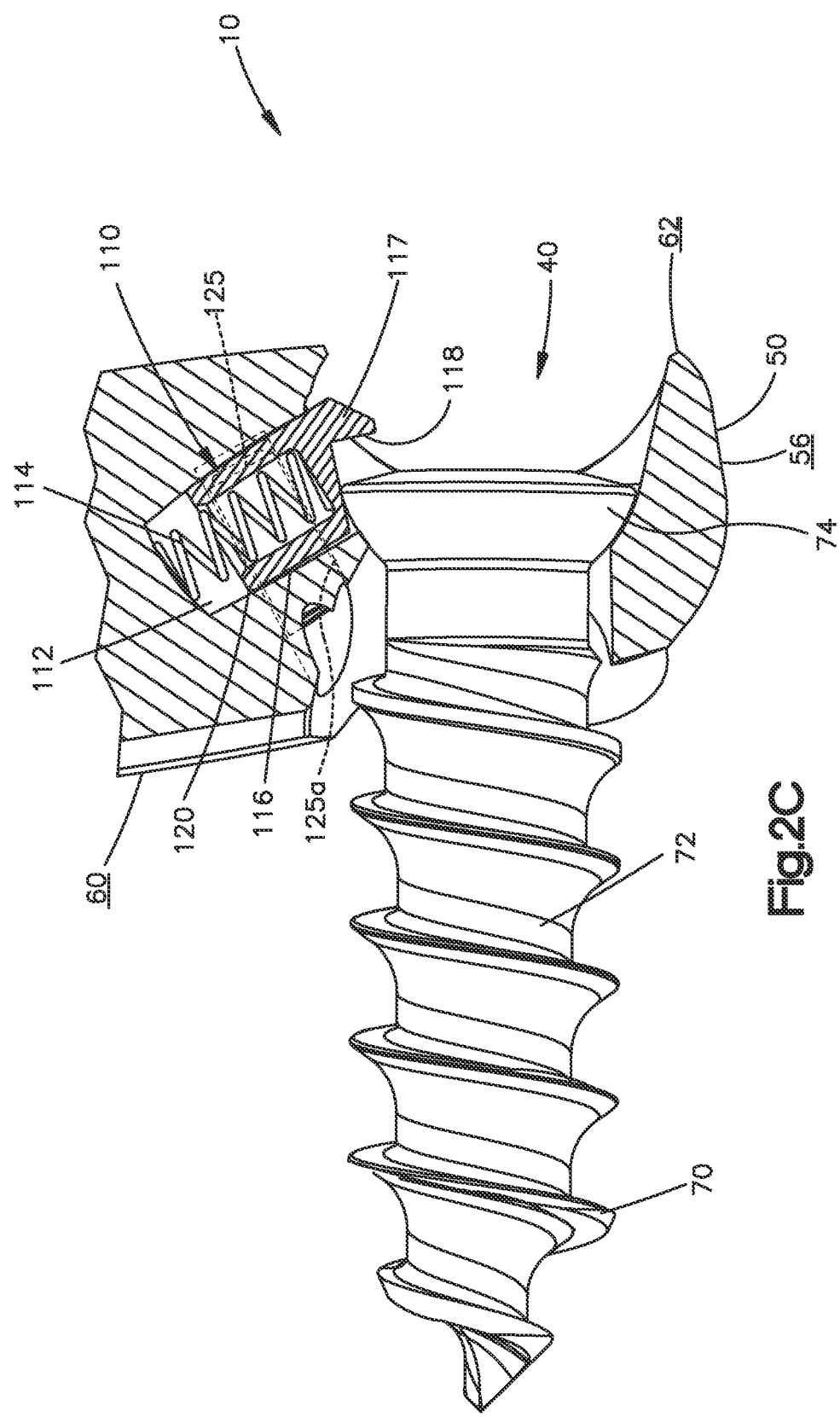
FIG. 2C illustrates a magnified, cross-sectional view of a retention mechanism used in connection with the implant of FIG. 1A.
Figure 2D:
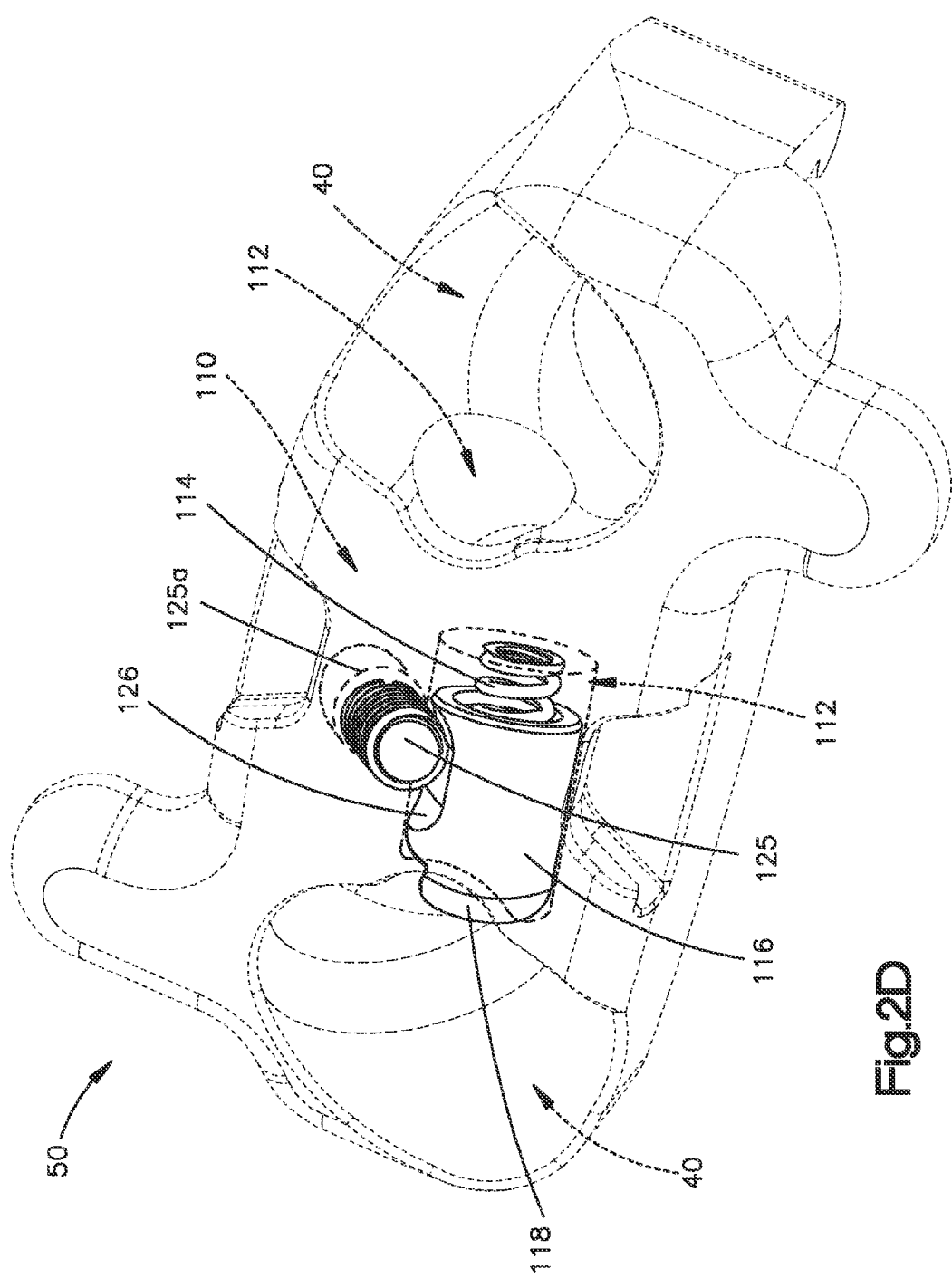
FIG. 2D illustrates a perspective view of the retention mechanism of FIG. 2C.
Figure 2G:
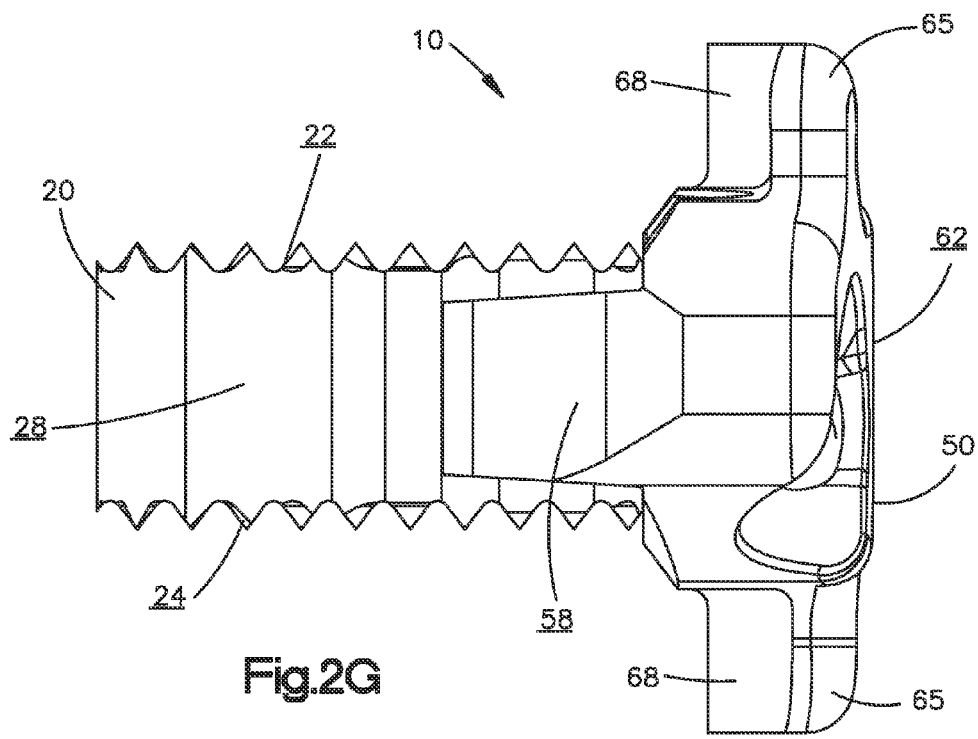
Figure 2H:
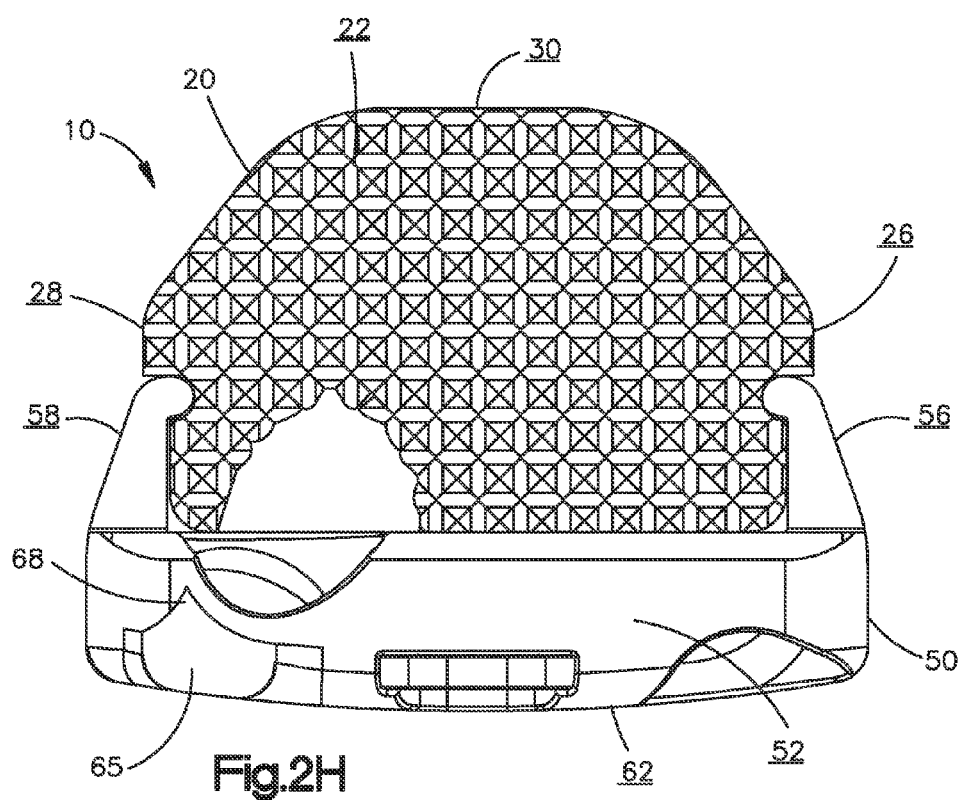
Figure 2I:
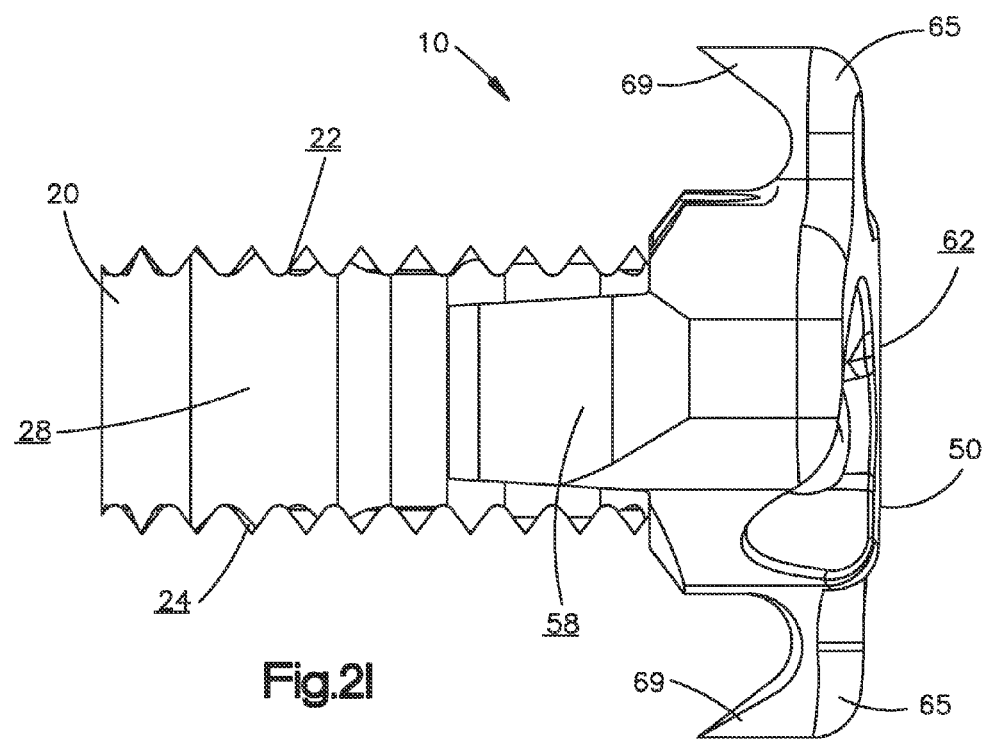
Figure 2J:
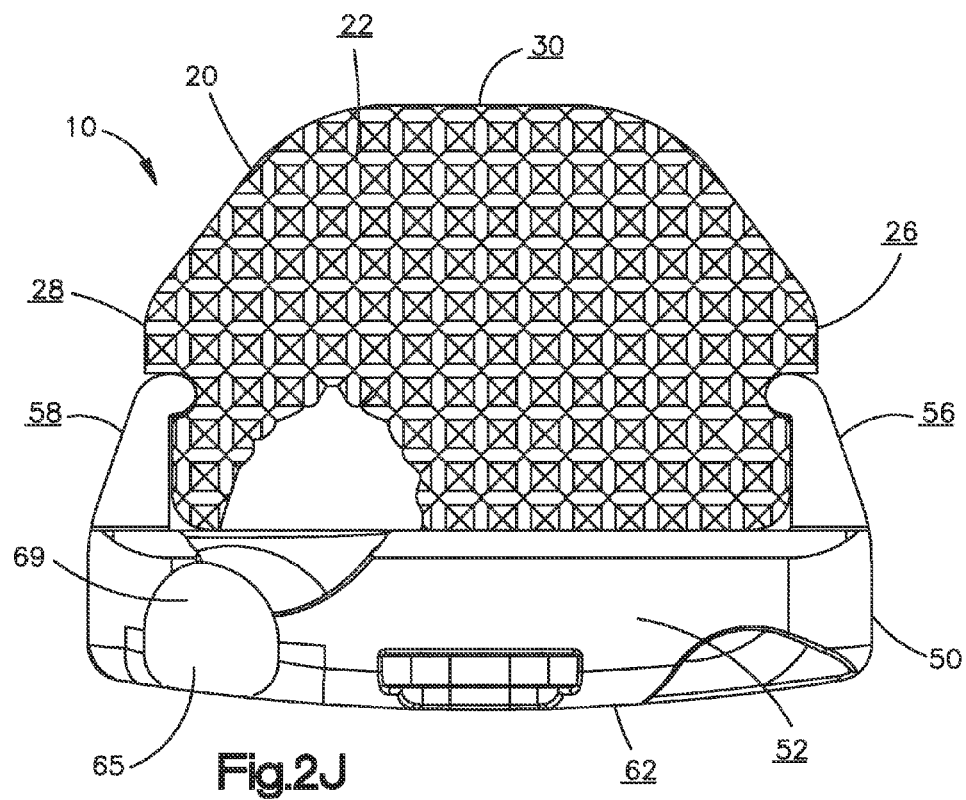

In use, the stops 65 are configured to abut the anterior aspects of the vertebral bodies V during implantation, although the stops 65 may abut the lateral or antero-lateral aspects of the vertebral bodies V depending upon the surgical procedure and insertion path being utilized. The stops 65 assist in preventing over-insertion of the implant 10 during implantation and assist in securing the position of the implant 10 during insertion of the bone fixation elements 70, as will be described in greater detail below. In part, due to the disposition of the stops 65, the implant 10 generally has a zero-profile external to the disc space D at least along a cranial-caudal midline, because the trailing surface 62 of the plate portion 50 can be designed to be convex to match the disc space D. Referring to FIGS. 2E-2J, a distal surface 65a of the stops 65 can be configured to embed at least partially into the vertebral bodies V during impaction to further reduce the profile of the plate portion 50 exterior to the disc space D, if so desired. For example, as shown in FIG. 2E, the distal surface 65a of the stops 65 may include a pyramid shaped projection or tooth 66 extending therefrom for embedding at least partially into the vertebral bodies V during impaction. Alternatively, the distal surface 65a of the stops 65 may include a plurality of projections or teeth 67 (as shown in FIG. 2F), a vertical blade type projection 68 (as shown in FIGS. 2G and 2H) or a transverse blade type projection 69 (as shown in FIGS. 2I and 2J) extending therefrom for embedding at least partially into the vertebral bodies V during impaction.

In operation, a surgeon prepares a pathway or channel to the disc space D, performs at least a partial discectomy, and inserts the implant 10 including the spacer portion 20 and the plate portion 50 into the disc space D until the stops 65 contact the adjacent vertebral bodes V. After the surgeon has chosen a desirable entry angle for the bone fixation elements 70, the surgeon advances the first and second bone fixation elements 70 into and through the bone fixation holes 40 at the selected angle, with or without the prior formation of pilot holes. Advancement of the bone fixation elements 70 into the bone fixation holes 40 causes the head portion 74 of the bone fixation elements 70 to contact the inner spherical portions of the bone fixation holes 40 and tends to draw the vertebral bodies V into alignment as opposed to resulting in the over-insertion of the implant 100 since the stops 65 guide the movement of the vertebral bodies V during bone fixation manipulation. That is, because the stops 65 contact the adjacent vertebral bodies V and prevents over-insertion of the implant 10 into the disc space D, advancement of the bone fixation elements 70 tends to pull and/or reposition the adjacent vertebral bodies V together to promote fusion. The bone fixation elements 70 are advanced until the vertebral bodies V are optimally aligned and the head portions 74 of the bone fixation elements 70 are advanced into the spherical portions of the bone fixation holes 70.

As the bone fixation elements 70 advance through the bone fixation holes 40, the underside of the head portion 74 of the bone fixation elements 70 contact the first end 118, preferably a tapered end portion 117, of the snapper elements 116 that protrude into the bone fixation holes 40, thereby urging the snapper elements 116 to recoil upon the spring 114 and retracting the snapper elements 116 from the bone fixation holes 40 so that the bone fixation elements 70 can be implanted. Once the head portions 74 of the bone fixation elements 70 advance past the tapered end portion 117 of the snapper elements 116, the spring 114 forces the snapper elements 116 back to their initial position in which the snapper elements 116 protrude at least partially into the bone fixation holes 40. In this position, the first end 118 of the snapper element 116 is designed to cover at least a portion, contact and/or interact with the top surface of the head portions 74 of the bone fixation elements 70 to block the head portions 74 of the bone fixation elements 70 and limit the bone fixation elements 70 from backing-out of the bone fixation holes 40. Specifically, the first end 118 of the snapper element 110 preferably extends into the bone fixation hole 40 such that the head portion 74 of the bone fixation element 70 is unable to move out of the bone fixation hole 40 without impacting the first end 118.

Figure 3B:
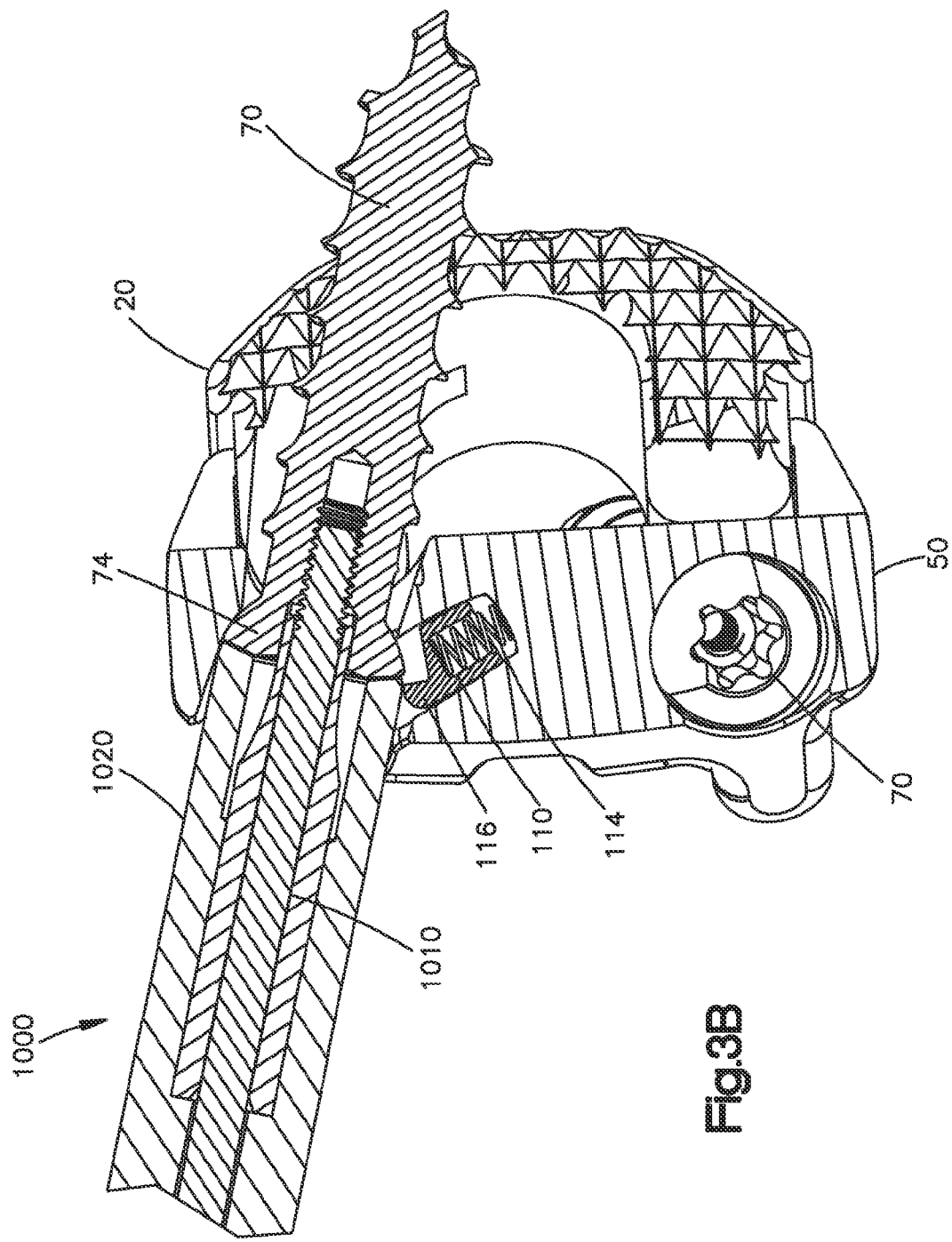
FIG. 3B illustrates a magnified, cross-sectional view of the removal instrument of FIG. 3A, taken along line 3B-3B of FIG. 3A.

Post implantation, the bone fixation elements 70 are preferably free to toggle to allow for settling during postoperative healing. Referring to FIGS. 3A and 3B, if a surgeon decides the placement of the implant 10 is not optimal, adjustments can be made by compressing the snapper elements 116 with a blunt instrument or a sleeve thereby allowing the bone fixation elements 70 to be removed. For example, a removal instrument 1000 may include an inner shaft 1010 for engaging the bone fixation element 70 and an outer shaft 1020 for contacting and recoiling the snapper element 116 so that the bone fixation element 70 may be removed from the plate portion 50.

Referring to FIGS. 4A-5B, the intervertebral implant 200 of a second preferred embodiment includes the interbody spacer portion 220, the plate portion 250, first and second bone fixation elements 70 and the retention mechanism. In the second preferred embodiment, the retention mechanism is in the form of a propeller 310 moveable, more preferably rotatable, between a first position (illustrated in FIGS. 4A, 4B and 5A) and a second position (illustrated in FIGS. 4C, 4D and 5B). In the first position, the propeller 310 does not interfere with first and second bone fixation holes 40 so that the first and second bone fixation elements 70 can be inserted into the adjacent vertebral bodies V. In the second position, the propeller 310 blocks or covers at least a portion of the bone fixation holes 40 and hence at least a portion of the implanted bone fixation elements 70 to prevent backing-out.

The propeller 310 is preferably preassembled or pre-attached to the plate portion 250. The propeller 310 may be attached to the plate portion 250 by any coupling mechanism now or hereafter known in the art including those described below. In the second preferred embodiment, the propeller 310 is preassembled to the plate portion 250 via a retaining screw 320 that interfaces with a threaded borehole (not shown) disposed between the bone fixation holes 40 formed in the plate portion 250. The retaining screw 320 may extend into and be threadably coupled to the spacer portion 220, but is not so limited. Alternatively, the retaining screw 320 may be securely coupled with respect to the plate portion 250 by a cross-pinned shaft, a rivet, a helical wedge attached to the shaft of the retaining screw 320, etc. The propeller 310 includes first and second ends 312, 314 defining a longitudinal axis that is generally transverse to the longitudinal axis of the retaining screw 320.

The propeller 310 and the retaining screw 320 are preferably rotatable through a range of about ninety degrees (90°) from the first position to the second position. In the first position, the longitudinal axis of the propeller 310 is oriented generally parallel to a longitudinal axis of the implant 200 and generally parallel to the cranial-caudal axis of the spine so that the propeller 310 does not interfere with the bone fixation holes 40 or bone fixation elements 70 to enable insertion of the bone fixation elements 70 into the adjacent vertebral bodies V. In the second position, the longitudinal axis of the propeller 310 is generally oriented perpendicular to the cranial-caudal axis of the spine so that the propeller 310 blocks or covers at least a portion of the bone fixation holes 40 and the bone fixation elements 70 to prevent backing-out. That is, in the second position, the propeller 310 covers at least a portion of the head portion 74 of the bone fixation elements 70 while in the first position, the propeller 310 permits insertion of the bone fixation elements 70 into the bone fixation holes 40 and into the adjacent vertebral bodies V.

The retaining screw 320 preferably includes an engagement feature 321 for engaging an insertion instrument 500, as will be described in greater detail below, to rotate the retaining screw 320 and the propeller 310 to and between the first and second positions. The retaining screw 320 and the propeller 310 are coupled to one another and preferably rotate together via a two point interference fit between the outer diameter of the retaining screw 320 and the diameter of a counterbore (not shown) through the propeller 310.

The plate portion 250 preferably includes a tapered recess 330 that forms a guide ramp so that in the second position, the propeller 310 preferably lies flush with the trailing surface 62 of the plate portion 250 (as best shown in FIG. 4D). Accordingly, in the first position (FIGS. 4A and 4B), the propeller 310 extends from the trailing surface 62 of the plate portion 250 and in the second position (FIGS. 4C and 4D), the anterior surface of the propeller 310 lies generally flush or somewhat recessed with respect to the trailing surface 62. Therefore, in an implanted configuration when the propeller 310 is in the second position, the entire implant 200, including the propeller 310, lies within the bounds of the patient's spine or posteriorly relative to the anterior aspect of the vertebrae V.

Figure 5A:
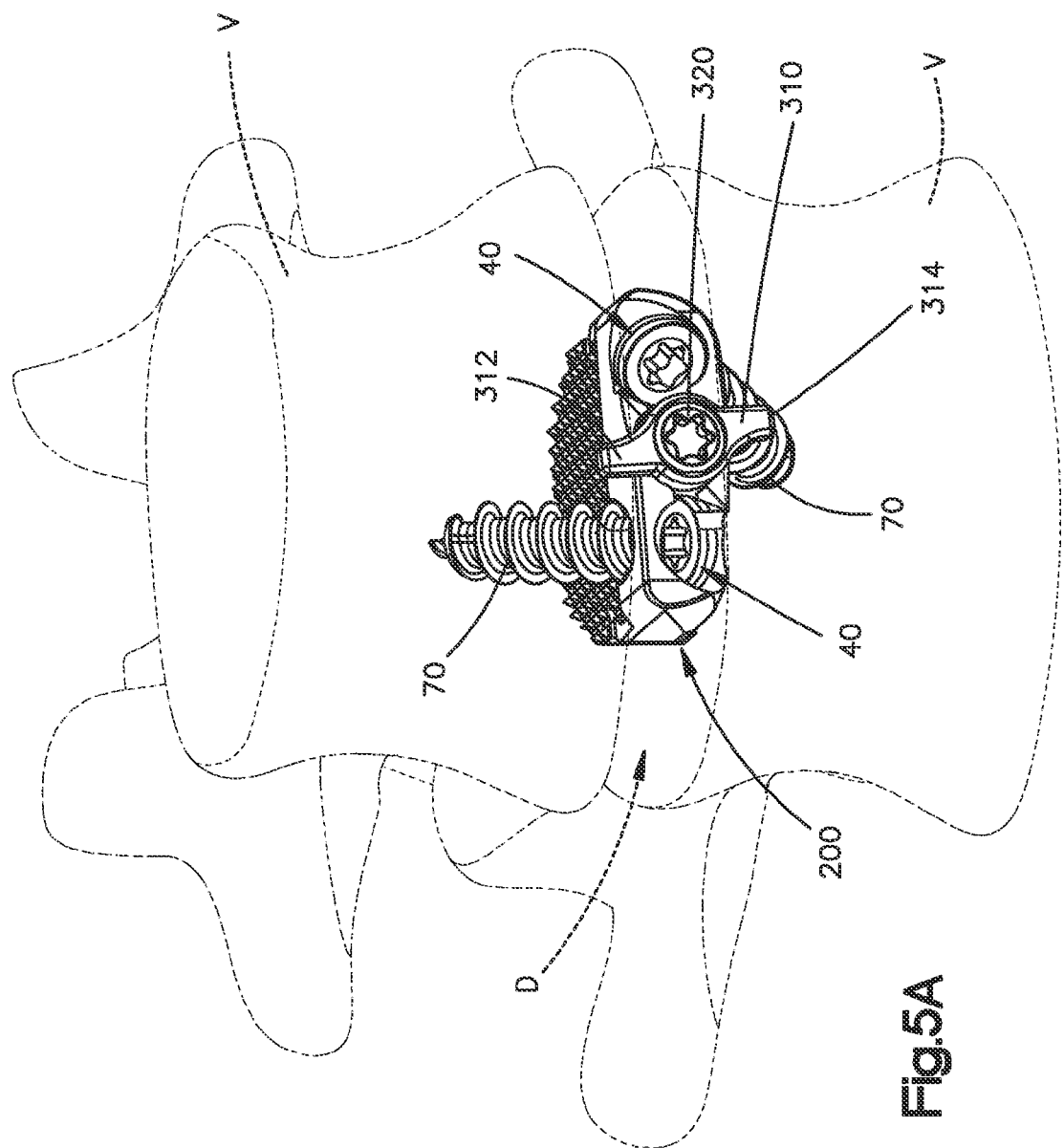
FIG. 5A illustrates an anterior perspective view of the implant shown in FIG. 4A inserted into an intervertebral disc space between adjacent vertebral bodies, the retention mechanism being in the first position wherein the retention mechanism acts as a stop preventing over-insertion of the implant into the disc space.
Figure 5B:
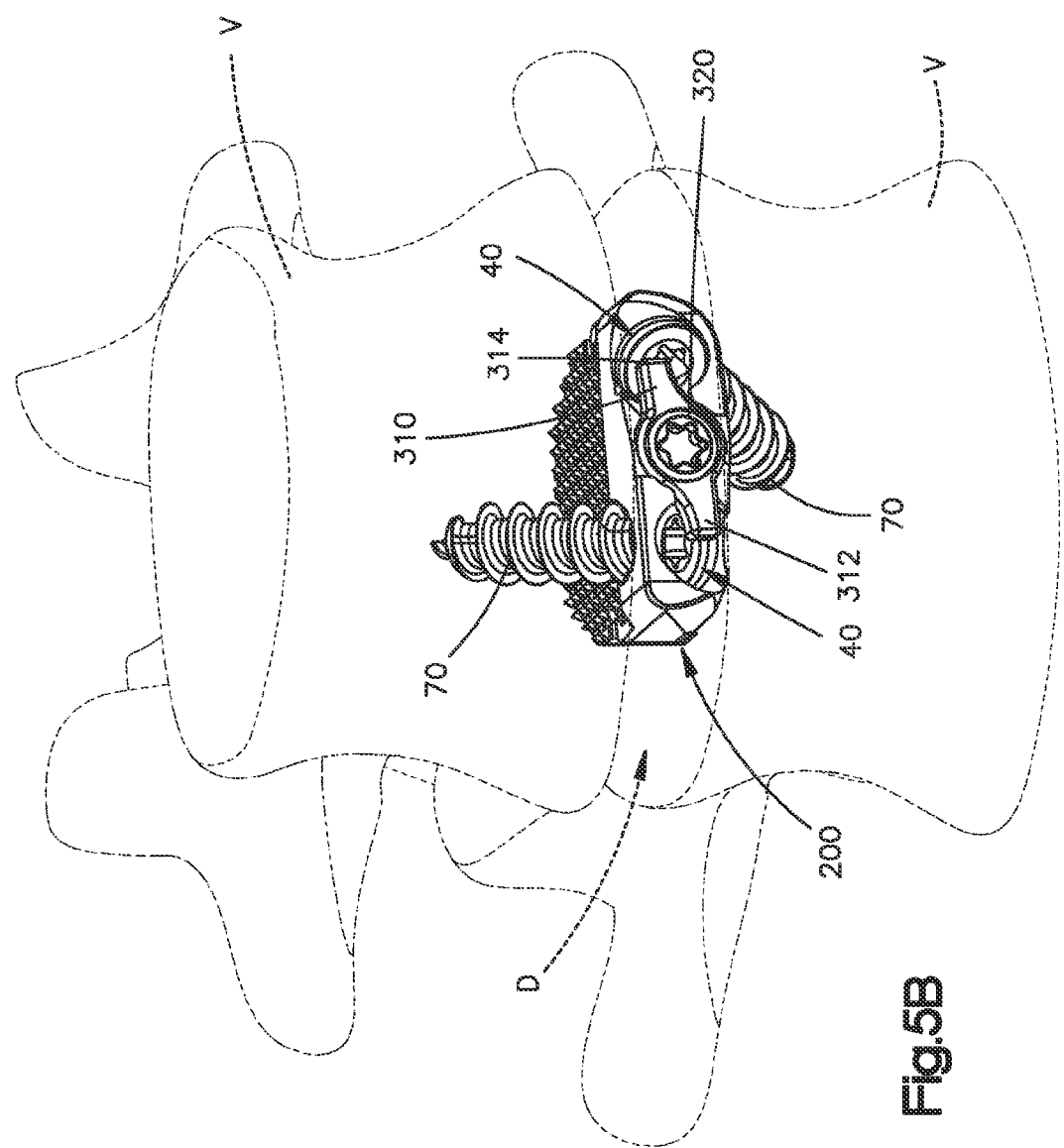
FIG. 5B illustrates an anterior perspective view of the implant shown in FIG. 4A inserted into an intervertebral disc space between adjacent vertebral bodies, the retention mechanism being in the second position.

In operation, a surgeon prepares a pathway or channel to the disc space D, performs at least a partial discectomy, and inserts the implant 200 including the spacer portion 220 and the plate portion 250 into the disc space D with the propeller 310 in the first position. In the first position, the propeller 310 is sized to act as a stop during implantation of the implant 200 to prevent over-insertion of the implant 200, as well as to secure the position of the implant 200 during the insertion of the bone fixation elements 70. Specifically, the ends 312, 314 of the propeller 310 contact and/or engage the adjacent vertebral bodies V to mechanically block further insertion of the implant 200 into the disc space D (as best shown in FIG. 5A).

After the surgeon has chosen a desirable entry angle for the bone fixation elements 70, the surgeon advances the first and second bone fixation elements 70 into and through the bone fixation holes 40 at the selected angle, with or without the prior formation of pilot holes. Advancement of the bone fixation elements 70 into the bone fixation holes 40 causes the head portion 74 of the bone fixation elements 70 to contact the inner spherical portions of the bone fixation holes 40 and tends to draw the vertebral bodies V into alignment as opposed to resulting in the over-insertion of the implant 200 since the propeller 310 preferably guides the movement of the vertebral bodies V during bone fixation manipulation. The bone fixation elements 70 are advanced until the vertebral bodies V are optimally aligned and the head portions 74 of the bone fixation elements 70 are advanced into the spherical portions of the bone fixation holes 70. The retaining screw 320 and the propeller 310 are then rotated ninety degrees (90°) from the first position to the second position, guided by the recesses 330 formed in the trailing surface 62 of the plate portion 250, by mating an insertion instrument to the instrument engagement feature 321 on the retaining screw 320. As the retaining screw 320 is rotated from the first position to the second position, the retaining screw 320 preferably advances distally, based on the pitch of the threading formed on its shaft, and the propeller 310 rotates down the guide ramp formed by the recesses 330 and comes to rest therein while overlying the head portions 74 of the bone fixation elements 70. The shape of the guide ramp formed by the recesses 330 preferably stops the propeller 310 from over rotating past the second position, such that the ends of the propeller 310 at least partially cover the head portions 74 of the bone fixation elements 70. As such, the bone fixation elements 70 are prevented from backing-out of the plate portion 250 and the spacer portion 220 by the propeller 310.

Post implantation, the bone fixation elements 70 are preferably free to toggle to allow for settling during postoperative healing. If a surgeon decides the placement of the implant 200 is not optimal, adjustments can be made by rotating the propeller 310 back to the first position, thereby unblocking the head portions 74 of the bone fixation elements 70 and allowing adjustments thereto.

Referring to FIGS. 6A and 6B, a second preferred embodiment of the plate portion 250' for use with implant 200 is illustrated. In the second preferred embodiment of the plate portion 250', the bone fixation holes 40 include a protruding thread blocking mechanism 350 that is sized and configured to permit the threaded advancement of the first and second bone fixation elements 70 with respect to the bone fixation holes 40 until the proximal most thread 73 formed on the shaft 72 of the bone fixation element 70 advances distally past the thread blocking mechanism 350, at which point the distal surface of the thread blocking mechanism 350 contacts a proximal side of the proximal most thread 73 to inhibit the first and second bone fixation elements 70 from backing-out of the bone fixation holes 40. The thread blocking mechanism 350 may assume the form of a raised ridge or interrupted ring of material or a variety of other protruding features configured to allow the proximal most thread 73 of the bone fixation element 70 to advance to a point from which retreat in the opposite direction is inhibited. Alternatively, the thread blocking mechanism 350 can be disposed within the bone fixation holes 40 to block the proximal surface of the head portions 74 of the bone fixation elements 70, as opposed to the proximal most threads 73. Alternatively, the thread blocking mechanism 350 can be configured to engage a corresponding indentation (not shown) formed on the sides of the head portions 74 of the bone fixation elements 70.

The bone fixation elements 70 may further include an undercut 75 between the proximal most thread 73 and the distal portion of the head portion 74 for enabling the bone fixation element 70 to generally rotate freely after being fully seated in the bone fixation hole 40 to thereby permit lagging of the vertebral bodies V with respect to the implant 200 during implantation.

In operation, the implant 200 is positioned between the adjacent vertebral bodies V and the bone fixation elements 70 are advanced into the bone fixation holes 40 until the proximal most thread 73 formed on the shaft portion 72 of the bone fixation elements 70 advance past the protruding thread blocking mechanism 350. The bone fixation elements 70 are fully seated with respect to the plate portion 250' in this position. The distal surface of the thread blocking mechanism 350 contacts the proximal side of the proximal most thread 73 formed on the shaft portions 72 of the bone fixation elements 70 to limit the bone fixation elements 70 from backing-out of the bone fixation holes 40. The bone fixation elements 70 are generally free to rotate after being fully seated due to the inclusion of the undercuts 75 between the proximal most thread 73 and the head portion 74 of each bone fixation elements 70 to permit lagging of the vertebral bodies V with respect to the implant 200 during implantation. The propeller 310 can then be utilized in conjunction with the thread blocking mechanism 350 to secure the position of the implant 200 during the insertion of the bone fixation elements 270, as well as to add additional back-out prevention. Alternatively, it is envisioned that the thread blocking mechanism 350 can be incorporated into the first preferred embodiment of the implant 10.

Referring to FIGS. 7A and 7B, a third preferred embodiment of the plate portion 250" for use with the implant 200 is illustrated. The third preferred embodiment of the plate portion 250" includes an alternate coupling mechanism for coupling the propeller 310" to the plate portion 250". In this embodiment, the propeller 310" includes a plurality of slots 317" extending from a distal end 316" of the propeller 310" so that the propeller 310" includes a plurality of spring-like fingers 315" oriented along an axis that extends distally, generally perpendicular to the longitudinal axis of the ends 312", 314" of the propeller 310". The spring fingers 315" preferably include an outwardly extending flange 318" at the distal end 316" thereof. The plate portion 250" preferably includes a non-threaded borehole 263" disposed between the bone fixation holes 40. The non-threaded borehole 263" preferably includes one or more ramps 263a" and one or more steps 263b" for interfacing with the spring fingers 315" for securing the propeller 310" to the plate portion 250".

An optional retaining clip 340", such as a wishbone clip formed of, for example, elgiloy, may be mounted in the borehole 263" to further assist in securing the propeller 310" to the plate portion 250" by allowing insertion of the propeller 310" into the borehole 263" while providing additional protection against the propeller 310" from backing-out of the borehole 263".

In operation, the propeller 310" is assembled to the plate portion 250" by inserting the spring fingers 315" into the borehole 263" until the propeller 310" snaps into the borehole 263", retaining the propeller 310" therein. That is, as the spring fingers 315" advance into the borehole 263", the tapered flanges 318" formed on the distal end 316" of the propeller 310" and the spring fingers 315" compress so that the fingers 315" pass through the optional retaining clip 340" after which the spring fingers 315" partially spring back outwardly. The retaining clip 340" may additionally flex slightly outwardly as the flange 318" passes therethrough, after which the retaining clip 340" springs back to its initial configuration. As the spring fingers 315" continue to advance into the borehole 263", the fingers 315" pass over the step 263b" and subsequently flex outwardly to their non-deflected configuration adjacent the ramp 263a". In this manner, the propeller 310" is prevented from backing-out through the borehole 263" via interaction between the flanges 318" and the step 263b".

Referring to FIG. 8, a fourth preferred embodiment of the plate portion 250'" for use with the implant 200 is illustrated. The fourth preferred embodiment of the plate portion 250'" includes a third alternate coupling mechanism for coupling the propeller 310'" to the plate portion 250'". In this embodiment, the non-threaded borehole 263'" includes a first ramp 263a'", a first step 263b'", a second preferred helical ramp 263c'", and a second step 263d'"" as one moves from the trailing surface 62 of the plate portion 250'. The configuration of the propeller 310'" is substantially identical to the propeller 310" of the second exemplary coupling mechanism described above.

In operation, the propeller 310' is assembled to the plate portion 250'" by inserting the spring fingers 315'" into the non-threaded borehole 263'" until the propeller 310' snaps into the borehole 263', which retains the propeller 310'" therein. As the spring fingers 315'" advance into the borehole 263'", the spring fingers 315' compress as the tapered flanges 318'" pass along the first ramp 263a'" and over the first step 263b'", at which point the spring fingers 315'" and the flanges 318'" partially spring outwardly thereby securing the propeller 310' to the plate portion 250'". The propeller 310'" is prevented from backing-out through the borehole 263'" via interaction between the flanges 318'" and the first step 263a'". In addition, as the propeller 310'" is moved from the first position to the second position, the spring fingers 315'" further advance into the borehole 263'", wherein the flange 318'" is guided by the preferred helically formed second ramp 263c'", until the flange 318'" passes over the second step 263d'". The spring fingers 315'" and the flanges 318'" flex outwardly into their non-deflected configuration to block the propeller 310'" from backing-out through the borehole 263'" via interaction between the flanges 318'" and the second step 263d'".

Figure 9A:
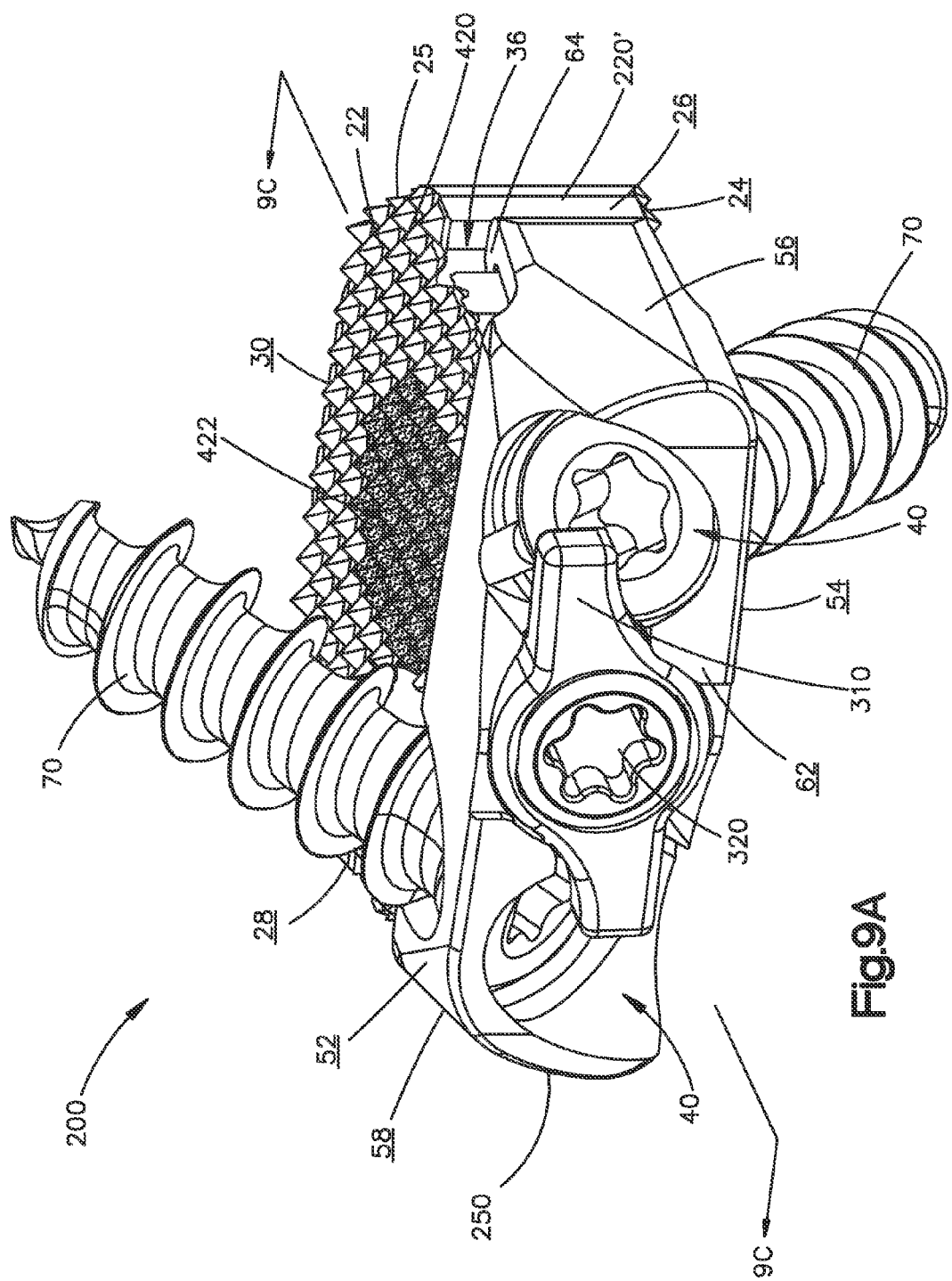
FIG. 9A illustrates an anterior perspective view of the implant shown in FIG. 4A, the implant incorporating a second exemplary spacer portion.
Figure 9C:
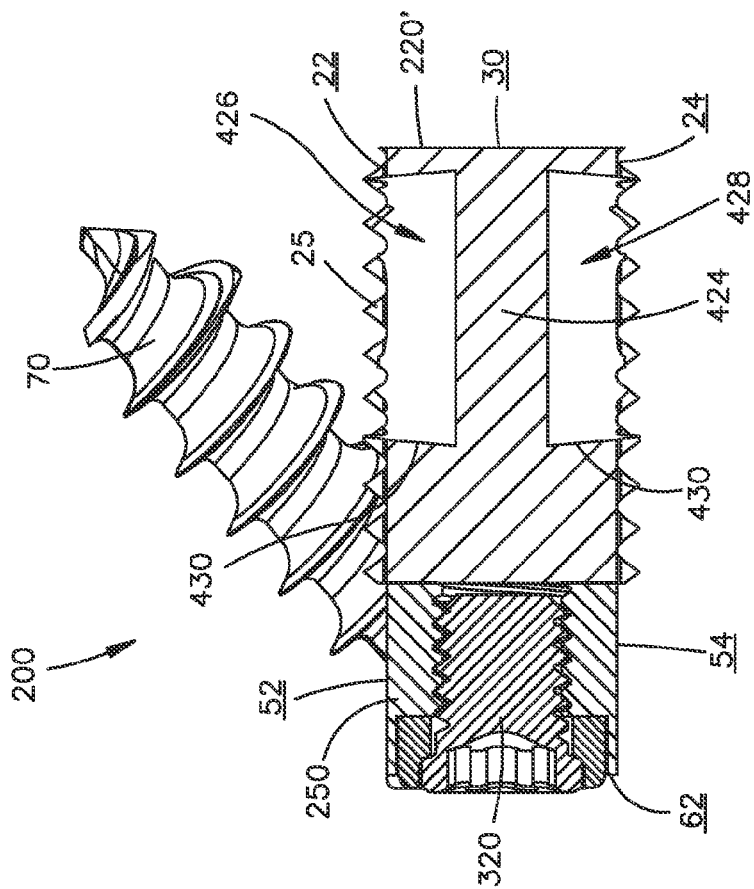
FIG. 9C illustrates a cross-sectional view of the implant shown in FIG. 9A, taken along line 9C-9C in FIG. 9A with the optional porous PEEK portion omitted.
Figure 9B:
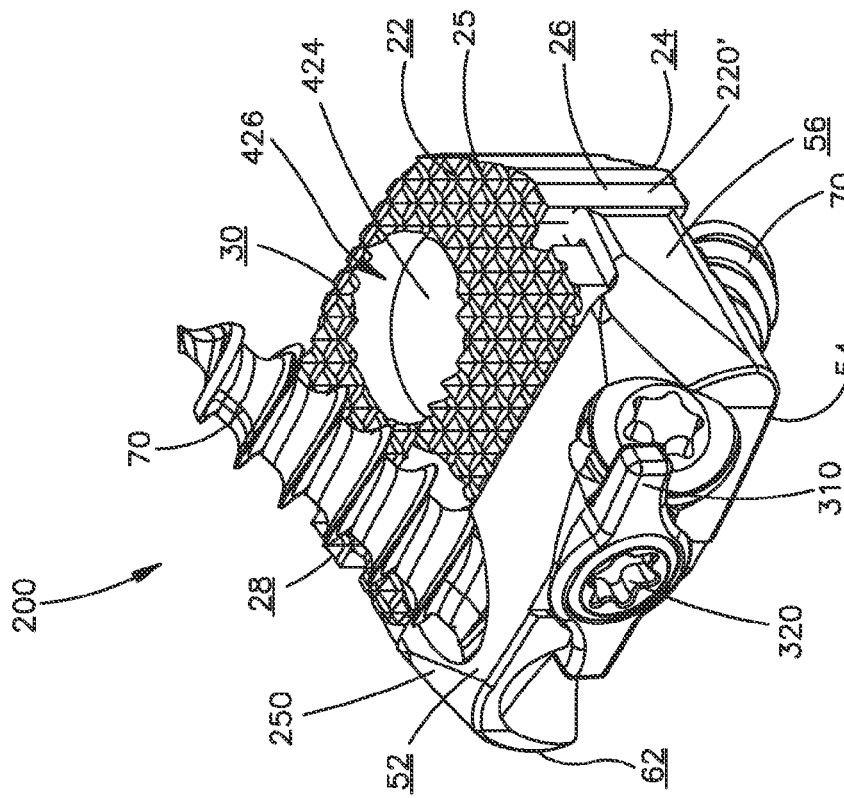
FIG. 9B illustrates a top perspective view of the implant shown in FIG. 9A with an optional porous PEEK portion omitted.
Figure 10D:
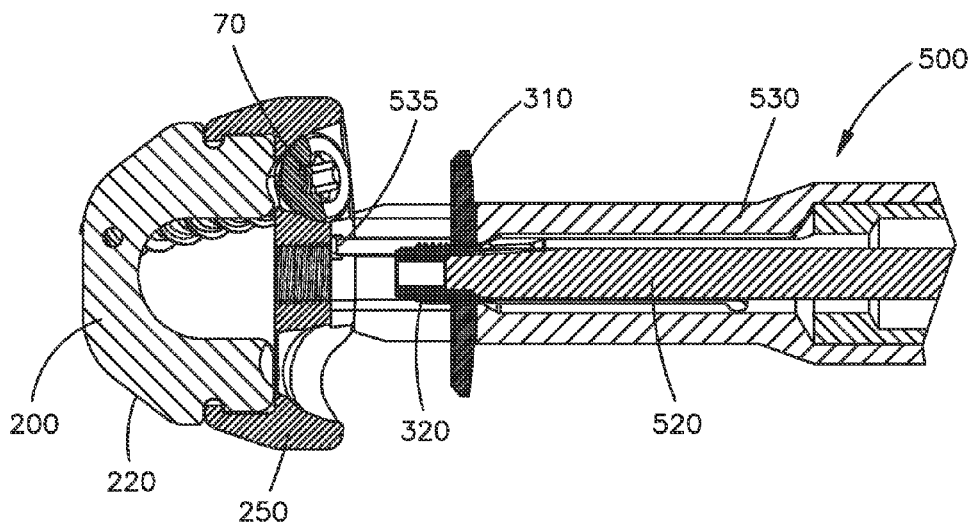
Figure 10E:
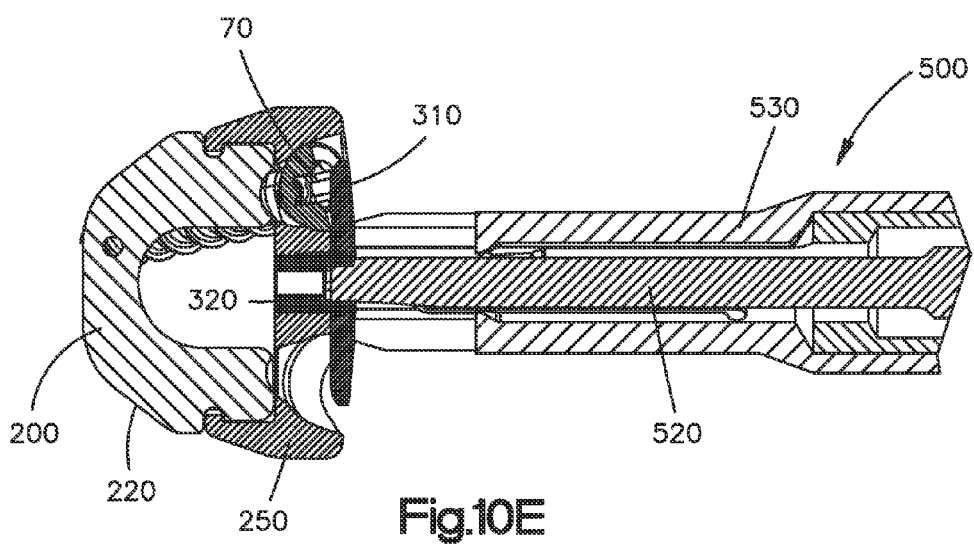

Referring to FIGS. 9A-9C, an alternate embodiment of the spacer portion 220' for use with the first and second preferred embodiments of the intervertebral implant 10-200 (second preferred embodiment illustrated) includes a centralized porous PEEK region 422 concentrically surrounded by a conventional PEEK portion 420.

In operation, the implant 200 is implanted and secured within the disc space D in a similar manner as previously described. The central porous PEEK portion 422 of the spacer portion 220' has a porosity that provides a suitable pathway through which blood is able to flow and bone is able to grow to assist in promoting fusion with and between the adjacent vertebral bodies V. The porous PEEK portion 422 may extend from the top surface 22 to the bottom surface 24 of the spacer portion 220'. Alternatively, the spacer portion 220' may include a bridge 424. When the spacer portion 220' includes the bridge 424, first and second blind boreholes 426, 428 preferably extend from the top and bottom surfaces 22, 24, respectively, to the bridge 424. The blind boreholes 426, 428 may include tapered sidewalls 430 such that a diameter of the blind boreholes 426, 428 increases toward the center of the spacer portion 220'. The bridge 424 may be formed of the same material as the rest of the spacer portion 220', but is preferably constructed of porous PEEK. Alternately, the bridge 424 may be removable, e.g., capable of being popped out of the spacer portion 220' to provide an axial throughbore. In operation, the blind boreholes 426, 428 are preferably filled with bone graft or other fusion promoting material and the implant 200' is implanted into the disc space D between the adjacent vertebral bodies V. The optional tapered sidewalls 430 of the blind bores 426, 428 facilitate securing the position of the implant 200' within the disc space D as fusion occurs into the blind boreholes 426, 428.

Referring to FIGS. 10A-10E, an exemplary insertion instrument 500 and method for inserting the implant 200 will now be described. In connection with the exemplary method, the propeller 310 will be described and illustrated as unattached to the plate portion 250. However the exemplary method can be easily adapted to operate with the propeller 310 pre-attached to the plate portion 250 or adapted to operate with the first preferred embodiment of the implant 10, as would be apparent to one having ordinary skill in the art based upon a review of the present application.

The insertion instrument 500 is configured to couple to the propeller 310, to couple to the plate portion 250, to insert the implant 200 at least partially into the disc space D, to permit insertion of the bone fixation elements 70 into the bone fixation holes 40, to secure the propeller 310 to the plate portion 250, if necessary, and to rotate the propeller 310 from the first position to the second position, if necessary.

The insertion instrument 500 preferably includes an inner shaft 520 and an outer tubular member 530. The inner shaft 520 preferably includes a distal engagement feature 525, such as a star drive, for interfacing with the engagement feature 321 formed on the retaining screw 320. The outer tubular member 530 preferably includes a distal engagement feature 535 for interfacing with a corresponding engagement feature (not shown) formed on the plate portion 250. Accordingly, the instrument 500 retains the propeller 310 by securing the engagement feature 525 formed on the inner shaft 520 of the instrument 500 to the propeller 310. The instrument 500 retains the implant 200 by grasping the plate portion 250 with the engagement feature 535 formed on the outer tubular member 530.

The inner shaft 520 is configured to translate within the outer tubular member 530 along a longitudinal axis 501 of the instrument 500. Accordingly, the inner shaft 520, and hence the propeller 310, may be translated proximally with respect to the outer tubular member 530, and hence with respect to the implant 200. For embodiments where the propeller 310 is unattached to the plate portion 250 and where the plate portion 250 does not include one or more stops, the instrument 500 may also include one or more stops (not shown) to prevent over-insertion of the implant 200 into the disc space D as well as to secure the position of the implant 200 with respect to the disc space D during the implantation of the bone fixation elements 70.

In operation, the surgeon inserts the implant 200 into the disc space D by using the instrument 500 to advance the implant 200 into the disc space D between the adjacent vertebral bodies V until one or more stops (not shown) abut the anterior (or lateral or antero-lateral) aspects of the vertebral bodies V. The bone fixation elements 70 are then inserted through the bone fixation holes 40 and into the vertebral bodies V while lagging of the implant 200 is limited by the interaction of the stops with the vertebral bodies V.

If unattached, the propeller 310 and the retaining screw 320 may then be advanced into a corresponding borehole 263 formed in the plate portion 250 by translating the inner shaft 520 distally with respect to the outer tubular member 530. The inner shaft 250 is then rotated so that the propeller 310 moves from its first position to its second position to prevent back-out of the implanted bone fixation elements 70. The instrument 500 is then decoupled from the propeller 310 and the retaining screw 320.

Figure 11A:
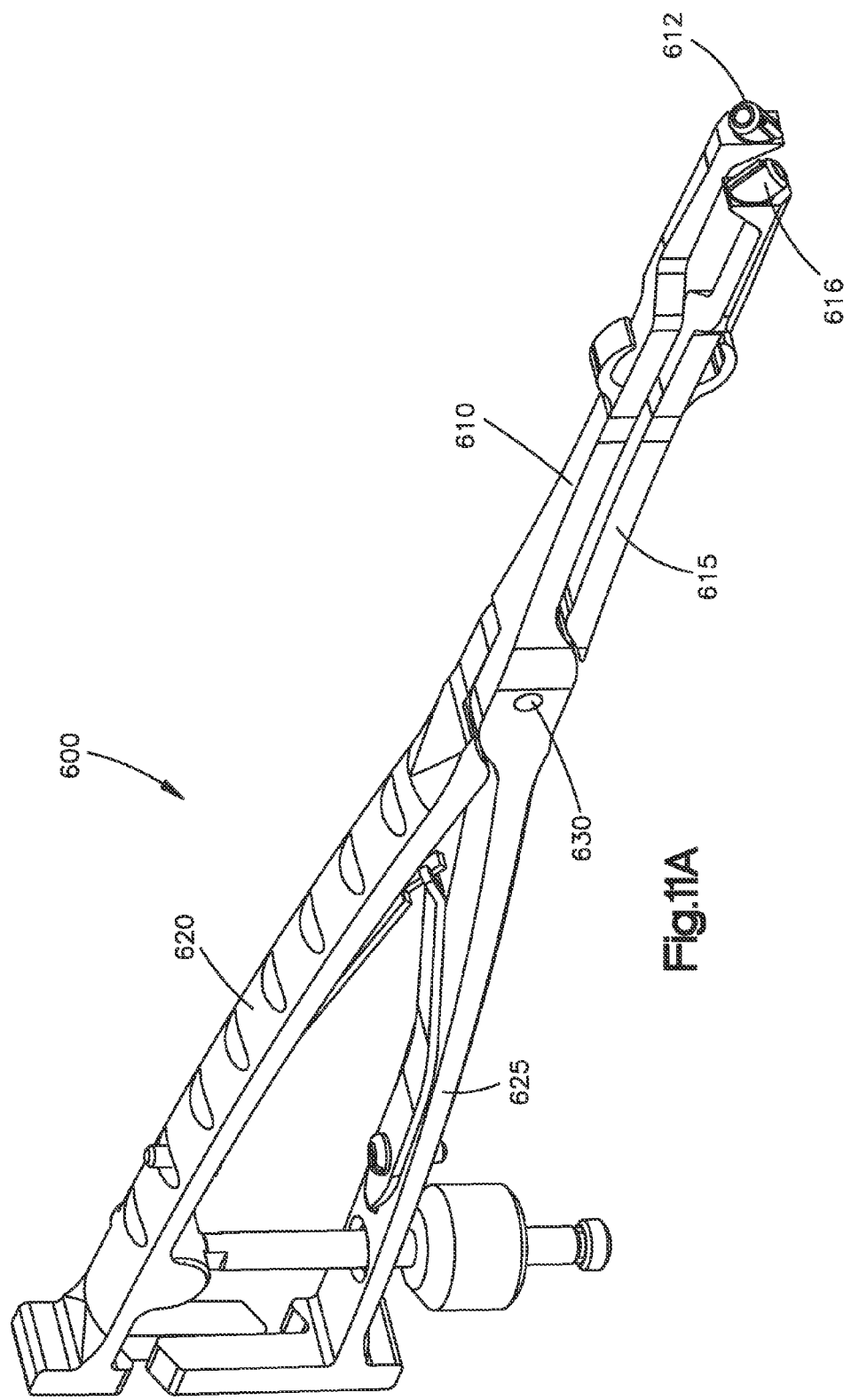

Referring to FIGS. 11A-11C, an optional inserter and drill guide instrument 600 can be utilized to insert any of the previously described implants 10-200 and to align the trajectory of an awl, drill, driver instrument, etc. for pilot hole formation and/or bone fixation element insertion. The inserter and drill guide instrument 600 includes a pair of arms 610, 615 extending from a pair of handles 620, 625 that are coupled at a pivot point 630. The arms 610, 615 include aiming barrels 612, 616 at their distal ends, respectively, for aligning the trajectory of the awl, drill, bone fixation elements, etc. The barrels 612, 616 include guide ribs 613, 617, respectively, disposed on their outer surface for interfacing with a key 625 formed in the bone fixation holes 40 of the implant 200. The interfacing guide ribs 613, 617 and keys 625 are configured to limit rotation of the implant 10-200 relative to the instrument 600, a feature that is especially preferred for implants 10-200 having only two bone fixation holes 40.

In operation, the arms 610, 615 of the inserter and drill guide instrument 600 are opened by squeezing the handles 620, 625 together and the barrels 612, 616 are inserted into the bone fixation holes 40 formed in the plate portion 250 such that the guide ribs 613, 617 interface with the keys 625. Upon secure grasping of the implant 10-200, the arms 610, 615 are locked into place and the instrument 600 may be used to insert the implant 10-200 into an at least partially cleared out disc space D between the vertebral bodies V. The barrels 612, 616 can then be used to align the trajectory of an awl, drill, etc. to form pilot holes for the bone fixation elements 70 or may align the trajectory of the bone fixation elements 70 in the case where self-drilling bone fixation elements 70 are utilized. Subsequent to the implantation of the bone fixation elements 70, the arms 610, 615 are unlocked and the inserter and drill guide instrument 600 is decoupled from the implant assembly.

While the foregoing description and drawings represent the preferred embodiments of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

We claim:

1. An implant for insertion into an intervertebral disc space between superior and inferior vertebral bodies, the implant comprising:

a spacer portion including a top surface configured to face the superior vertebral body, and a bottom surface configured to face the inferior vertebral body;

a plate portion coupled to the spacer portion, the plate portion including a top surface, and a bottom surface, the plate portion further including a first bone fixation hole configured to receive a first bone fixation element along a first insertion direction, the plate portion further including a first borehole intersecting with the first bone fixation hole; and a first spring biased snapper element disposed at least partially in the first borehole, the first spring biased snapper element configured to prevent the first bone fixation element from backing-out of the first bone fixation hole along a first back-out direction that is opposite the first insertion direction when the first bone fixation element is inserted into the first bone fixation hole, the first spring biased snapper element including a first end that defines a tapered top surface and a flat bottom surface;

wherein the first spring biased snapper element is moveable to a position such that at least a portion of the first end protrudes into the first bone fixation hole so that when the first bone fixation element is inserted into the first bone fixation hole the flat bottom surface of the first spring biased snapper element at least partially is aligned with the first bone fixation element along the first back-out direction.

2. The implant of claim 1, wherein a height of the plate portion is substantially equal to a height of the spacer portion and a width of the plate portion is substantially equal to a width of the spacer portion.

3. The implant of claim 1, wherein the spacer portion includes a first side surface, a second side surface, a first recess formed in the first side surface and a second recess formed in the second side surface, the first and second recesses configured to engage first and second projections, respectively, extending from the plate portion.

4. The implant of claim 1, wherein the spacer portion further includes a centralized region comprising a first material concentrically surrounded by a portion comprising a second material that is different from the first material.

5. The implant of claim 4, wherein the centralized region extends from the top surface to the bottom surface.

6. The implant of claim 4, wherein the first material is more porous than the second material.

7. The implant of claim 1, wherein the first bone fixation hole is angled such that when the first bone fixation element is received within the first bone fixation hole the first fixation element engages the superior vertebral body.

8. The implant of claim 1, wherein the first spring biased snapper element is biased to the position.

9. The implant of claim 1, wherein:
the plate portion further includes a second bone fixation hole configured to receive a second bone fixation element along a second insertion direction, the plate portion further including a second borehole intersecting with the second bone fixation hole; and
a second spring biased snapper element disposed at least partially within the second bore hole, the second spring biased snapper element configured to prevent the second bone fixation element from backing-out of the second bone fixation hole along a second back-out direction that is opposite the second insertion direction, when the second bone fixation element is inserted into the second bone fixation hole, the second spring biased snapper element including a first end that includes a tapered top surface and a flat bottom surface;
wherein the second spring biased snapper element is moveable to a position such that at least a portion of the first end of the second spring biased snapper element protrudes into the second bone fixation hole so that when the second bone fixation element is inserted into the second bone fixation hole the flat bottom surface of the second spring biased snapper element at least partially covers the second bone fixation element with respect to the second back-out direction.

10. The implant of claim 9, wherein each of the first and second spring biased snapper elements includes a spring and a snapper element, the snapper element including the first end that protrudes into the first and second bone fixation holes, and a second end configured to interact with the spring.

11. The implant of claim 10, wherein the first and second spring biased snapper elements are secured within the first and second boreholes, respectively, via first and second pins, respectively.

12. The implant of claim 9, wherein the position of the first and second spring biased snapper elements is a first position, and insertion of the first and second bone fixation elements causes the first and second spring biased snapper elements to move from their respective first positions to respective second positions in which the first and second spring biased snapper elements are removed from the first and second bone fixation holes.

13. The implant of claim 9, wherein the position of the first and second spring biased snapper elements is a first position, and insertion of the first and second bone fixation elements causes a head portion of the first and second bone fixation elements to contact the first and second spring biased snapper elements, respectively, to cause the first and second spring biased snapper elements to recoil from their first positions to respective second positions.

14. The implant of claim 13, wherein further insertion of the first and second bone fixation elements causes the head portions of the first and second bone fixation elements to move distally of the first and second spring biased snapper elements resulting in the first and second snapper elements automatically moving from their second position to their first positions.

15. The implant of claim 9, further comprising first and second stops configured to prevent over-insertion of the implant during implantation and configured to assist in securing a position of the implant during insertion of the first and second bone fixation elements, the first stop extending superiorly of the top surface of the plate portion such that the first stop is configured to contact the superior vertebral body, the second stop extending inferiorly of the bottom surface of the plate portion such that the second stop is configured to contact the inferior vertebral body.

16. The implant of claim 15, wherein the first and second stops are integrally formed with the plate portion.

17. The implant of claim 15, wherein the first and second stops each include a distal surface that is configured to at least partially embed into the respective superior or inferior vertebral body.

18. The implant of claim 17, wherein the distal surface of each of the first and second stops includes a pyramid shaped projection or tooth configured to at least partially embed into the respective superior or inferior vertebral body.

19. The implant of claim 17, wherein the distal surface of each of the first and second stops includes a plurality of projections or teeth configured to at least partially embed into the respective superior or inferior vertebral body.

20. The implant of claim 17, wherein the distal surface of each of the first and second stops includes a vertical blade type projection configured to at least partially embed into the respective superior or inferior vertebral body.

21. The implant of claim 17, wherein the distal surface of each of the first and second stops includes transverse blade type projection configured to at least partially embed into the respective superior or inferior vertebral body.

22. The implant of claim 9, wherein the plate portion further includes a thread blocking mechanism that is configured to permit the advancement of the respective first or second bone fixation element into the respective first or second bone fixation hole to a desired depth, and once the respective first or second bone fixation element has reached the desired depth the thread blocking mechanism inhibits the respective first or second bone fixation element from backing out of the respective first or second bone fixation hole.

23. The implant of claim 22, wherein the desired depth is the point at which a distal surface of the thread blocking mechanism contacts a proximal side of the proximal most thread.

24. The implant of claim 22, wherein the thread blocking mechanism comprises a raised ridge.

25. The implant of claim 22, wherein the thread blocking mechanism comprises an interrupted ring.

26. The implant of claim 6, wherein the first material comprises porous PEEK and the second material comprises conventional PEEK.

27. The implant of claim 9, wherein the second bone fixation hole is angled such that when the second bone fixation element is received within the second bone fixation hole the second bone fixation element engages the inferior vertebral body.

28. The implant of claim 9, further comprising a mechanism configured to be actuated from a first configuration to a second configuration, such that when the mechanism is in the first configuration the mechanism is located at least partially within the first or second borehole to secure the respective first or second snapper element within the first or second borehole, and when the mechanism is in the second configuration the first or second snapper element is capable of being inserted into or removed from the respective first or second borehole.

29. The implant of claim 9, wherein the first and second spring biased snapper elements are biased to their respective positions.

30. An implant for insertion into an intervertebral disc space between superior and inferior vertebral bodies, the implant comprising:
  a spacer portion including a top surface configured to face the superior vertebral body, and a bottom surface configured to face the inferior vertebral body;
  a plate portion coupled to the spacer portion, the plate portion including a top surface, and a bottom surface, the plate portion further including a first bone fixation hole, a first borehole, and a second borehole, the first bone fixation hole configured to receive a first bone fixation element, the first borehole intersecting with the first bone fixation hole, and the second borehole being offset and open to the first borehole, the plate portion further including a second bone fixation hole, a third borehole, and a fourth borehole, the second bone fixation hole configured to receive a second bone fixation element, the third borehole intersecting with the second bone fixation hole, and the fourth borehole being offset and open to the third borehole;
  a first spring biased snapper element positioned in the first borehole such that the first spring biased snapper element is moveable from a first position wherein a portion of the first spring biased snapper element protrudes into the first bone fixation hole to prevent the first bone fixation element from backing out of the first bone fixation hole, to a second position wherein the portion of the first spring biased snapper element is removed from the first bone fixation hole;
  a second spring biased snapper element positioned in the third borehole such that the second spring biased snapper element is moveable from a first position wherein a portion of second the spring biased snapper element protrudes into the second bone fixation hole to prevent the second bone fixation element from backing out of the second bone fixation hole, to a second position wherein the portion of the second spring biased snapper element is removed from the second bone fixation hole;
  a first mechanism that is located at least partially within the second borehole, the first mechanism moveable with respect to the first spring biased snapper element and configured to be positioned at least partially within the first borehole such that the first mechanism: 1) permits movement of the first spring biased snapper element between the first and second positions; and 2) prevents the first spring biased snapper element from exiting the first borehole entirely; and
  a second mechanism that is located at least partially within the fourth borehole, the second mechanism moveable with respect to the second spring biased snapper element and configured to be positioned at least partially within the third borehole such that the second mechanism: 1) permits movement of the second spring biased snapper element between the first and second positions; and 2) prevents the second spring biased snapper element from exiting the third borehole entirely;
  wherein the first and second spring biased snapper elements each include a first end that has a tapered top surface and a flat bottom surface such that when the first and second spring biased snapper elements are in their respective first positions and the first and second bone fixation elements are inserted into the first and second bone fixation holes, respectively, 1) the flat bottom surface of the first spring biased snapper element faces a head of the first bone fixation element such that back out of the first bone fixation element is prevented, and 2) the flat bottom surface of the second spring biased snapper element faces a head of the second bone fixation element such that back out of the second bone fixation element is prevented.

31. An implant for insertion into an intervertebral disc space between superior and inferior vertebral bodies, the implant comprising:
  a spacer portion including a top surface configured to face the superior vertebral body, and a bottom surface configured to face the inferior vertebral body;
  a plate portion coupled to the spacer portion, the plate portion including a top surface, and a bottom surface, the plate portion further including a first bone fixation hole, a first borehole, and a second borehole, the first bone fixation hole configured to receive a first bone fixation element, the first borehole intersecting with the first bone fixation hole, and the second borehole being offset and open to the first borehole, the plate portion further including a second bone fixation hole, a third borehole, and a fourth borehole, the second bone fixation hole configured to receive a second bone fixation element, the third borehole intersecting with the second bone fixation hole, and the fourth borehole being offset and open to the third borehole;
  a first spring biased snapper element positioned in the first borehole such that the first spring biased snapper element is moveable from a first position wherein a portion of the first spring biased snapper element protrudes into the first bone fixation hole to prevent the first bone fixation element from backing out of the first bone fixation hole, to a second position wherein the portion of the first spring biased snapper element is removed from the first bone fixation hole;
  a second spring biased snapper element positioned in the third borehole such that the second spring biased snapper element is moveable from a first position wherein a portion of second the spring biased snapper element protrudes into the second bone fixation hole to prevent the second bone fixation element from backing out of the second bone fixation hole, to a second position wherein the portion of the second spring biased snapper element is removed from the second bone fixation hole;

a first mechanism comprising a spring or a set screw, the first mechanism located at least partially within the second borehole, the first mechanism moveable with respect to the first spring biased snapper element and configured to be positioned at least partially within the first borehole such that the first mechanism: 1) permits movement of the first spring biased snapper element between the first and second positions; and 2) prevents the first spring biased snapper element from exiting the first borehole entirely; and a second mechanism comprising a spring or a set screw, the second mechanism located at least partially within the fourth borehole, the second mechanism moveable with respect to the second spring biased snapper element and configured to be positioned at least partially within the third borehole such that the second mechanism: 1) permits movement of the second spring biased snapper element between the first and second positions; and 2) prevents the second spring biased snapper element from exiting the third borehole entirely.

\* \* \* \* \*